(12) United States Patent
Folkman et al.

(10) Patent No.: US 7,645,735 B2
(45) Date of Patent: *Jan. 12, 2010

(54) ANTI-ANGIOGENIC PEPTIDES FOR TREATING OR PREVENTING ENDOMETRIOSIS

(75) Inventors: Judah Folkman, Brookline, MA (US); Kashi Javaherian, Lexington, MA (US); Christian Becker, Oxford (GB); Robert D'Amato, Lexington, MA (US)

(73) Assignee: Children's Medical Center Corporation, Boston, MA (US)

( * ) Notice: Subject to any disclaimer, the term of this patent is extended or adjusted under 35 U.S.C. 154(b) by 69 days.

This patent is subject to a terminal disclaimer.

(21) Appl. No.: 11/364,887

(22) Filed: Feb. 28, 2006

(65) Prior Publication Data

US 2006/0258583 A1    Nov. 16, 2006

Related U.S. Application Data

(63) Continuation-in-part of application No. PCT/US2004/028476, filed on Aug. 30, 2004.

(60) Provisional application No. 60/499,264, filed on Aug. 29, 2003, provisional application No. 60/539,213, filed on Jan. 26, 2004.

(51) Int. Cl.
  A61K 38/04    (2006.01)
  A61K 38/16    (2006.01)
(52) U.S. Cl. ........................................ 514/2
(58) Field of Classification Search .............. None
  See application file for complete search history.

(56) References Cited

U.S. PATENT DOCUMENTS

| | | | |
|---|---|---|---|
| 5,854,205 | A | 12/1998 | O'Reilly et al. |
| 6,017,949 | A | 1/2000 | D'Amato et al. |
| 6,306,819 | B1 * | 10/2001 | Rupnick et al. .............. 514/2 |
| 6,653,098 | B1 | 11/2003 | Violand et al. |
| 2002/0103129 | A1 * | 8/2002 | Ge et al. .................. 514/13 |
| 2004/0073007 | A1 | 4/2004 | Chillemi et al. |
| 2006/0122374 | A1 * | 6/2006 | Mertins et al. .............. 530/362 |
| 2006/0251699 | A1 * | 11/2006 | Folkman et al. ............. 424/423 |

FOREIGN PATENT DOCUMENTS

| | | |
|---|---|---|
| WO | WO-97/15666 | 5/1997 |
| WO | WO-99/29855 | 6/1999 |
| WO | WO-99/39702 | 8/1999 |
| WO | WO-99/48924 | 9/1999 |
| WO | WO-99/62944 | 12/1999 |
| WO | WO-00/11033 | 3/2000 |
| WO | WO-00/26368 | 5/2000 |
| WO | WO-00/60945 | 10/2000 |
| WO | WO-00/63249 | 10/2000 |
| WO | WO-00/67771 | 11/2000 |
| WO | WO-02/30982 | 4/2002 |
| WO | WO-02/068457 | 9/2002 |
| WO | WO-2005/021756 | 3/2005 |
| WO | WO-2005/042566 | 5/2005 |

OTHER PUBLICATIONS

Dhanabal et al. "Cloning, expression, and in vitro activity of human endostatin," Biochem. Biophys. Res. Comm., 1999, 258, 345-52.*
Boehm et al. "Zinc binding of endostatin is essential for its angiogenic activity," Biochem. Biophys., Res. Comm., 1998, 252, 190-4.*
MedlinePlus entry for endometriosis http://www.nlm.nih.gov/medlineplus/ency/article/000915.htm.*
AAF69009, http://www.ncbi.nlm.nih.gov/entrez/viewer.fcgi?db=protein&val=7739777.
Boehm et al. "Zinc-Binding of Endostatin Is Essential for Its Antiangiogenic Activity," Biochemical and Biophysical Research Communications, 252:190-194 (1998).
Cattaneo et al., "Human Endostatin-derived synthetic peptides possess potent antiangiogenic properties in vitro and in vivo," Experimental Cell Research, 283:230-236 (2003).
Chillemi et al., "Studies on the Structure—Activity Relationship of Endostation: Synthesis of Human Endostatin Peptides Exhibiting Potent Antiangiogenic Activities," J. Med. Chem. 46:4165-4172 (2003).
Cho et al., "N-/C-terminal deleted mutant of human endostatin efficiently acts as an anti-angiogenic and anti-tumorigenic agent," Oncology Reports, 11:191-195 (2004).
Hull et al., "Antiangiogenic Agents Are Effective Inhibitors of Endometriosis," The J. of Clinical Endocrinology & Metabolism, 88(6):2889-2899 (2003).
Kerbel et al., "Clinical Translation of Angiogenesis Inhibitors," Nature Reviews/Cancer, 2:727-739 (2002).
Morbidelli, et al., "Angiosuppressive and Angiostimulatory Effects Exerted by Synthetic Partial Sequences of Endostation," Clinical Cancer Research, 9:5358-5369 (2003).
Sjin, et al., "A 27-Amino-Acid Synthetic Peptide Corresponding to the NH2-Terminal Zinc-Binding Domain of Endostatin Is Responsible for Its Antitumor Activity," Cancer Res, 65(9):3656-3663 (2005).
Wickstrom et al., An Endostatin-derived Peptide Interacts with Integrins and Regulates Actin Cytoskeleton and Migration of Endothelial Cells, The Journal of Biological Chemistry, 279(19):20178-20185 (2004).
Jia et al., "Anticancer treatment of endostation gene therapy by targeting tumore neovasculature in c57/BL mice," Clin. Hemorheol, Microcirc., 23(2,3,4):251-257 (2000).
Office Action of U.S. Appl. No. 11/354,855 having a mail date of Feb. 20, 2007, including PTO Form 892.
Office Action of U.S. Appl. No. 11/354,855 having a mail date of Jul. 6, 2007, including PTO Form SB 08 initialed by Examiner.
Notice of Allowance for U.S. Appl. No. 11/354,855 having a mail date of Jan. 23, 2008, including PTO Form 892.

* cited by examiner

Primary Examiner—Cecilia Tsang
Assistant Examiner—Christina Bradley
(74) Attorney, Agent, or Firm—Foley Hoag LLP

(57) ABSTRACT

Provided herein are peptides from the N-terminal of endostatin proteins, including the first histidine of the protein, nucleic acids encoding the peptides, pharmaceutical compositions comprising the nucleic acids and proteins and methods for using the pharmaceutical compositions to treat or prevent endometriosis in a subject.

32 Claims, 14 Drawing Sheets

Figure 14

SEQ ID NO: 152 (AF184060 minus first atg):
```
  1     cacagcc accgcgactt ccagccggtg ctccacctgg ttgcgctcaa cagcccctg
 58     tcaggcggca tgcggggcat ccgcggggcc gacttccagt gcttccagca ggcgcgggcc
118     gtggggctgg cgggcacctt ccgcgccttc ctgtcctcgc gcctgcagga cctgtacagc
178     atcgtgcgcc gtgccgaccg cgcagccgtg cccatcgtca acctcaagga cgagctgctg
238     tttcccagct gggaggctct gttctcaggc tctgagggtc cgctgaagcc cggggcacgc
398     atcttctcct taacggcaa ggacgtcctg acccacccca cctggcccca gaagagcgtg
358     tggcatggct cggaccccaa cgggcgcagg ctgaccgaga gctactgtga cgtggcgg
418     acggaggctc cctcggccac gggccaggcc tactcgctgc tgggggggcag gctcctgggg
478     cagagtgccg cgagctgcca tcacgcctac atcgtgctat gcattgagaa cagcttcatg
538     actgcctcca agtag
```

SEQ ID NO: 153 (AAF01310 minus first M):
```
  1     hshrdfqpv lhlvalnspl sggmrgirga dfqcfqqara vglagtfraf lssrlqdlys
 60     ivrradraav pivnlkdell fpswealfsg segplkpgar ifsfngkdvl thptwpqksv
120     whgsdpngrr ltesycetwr teapsatgqa ysllggrllg qsaaschhay ivlciensfm
180     task
```

SEQ ID NO: 154 (AF257775):
```
  1     catactcatc aggactttca gccagtgctc cacctggtgg cactgaacac cccctgtct
 61     ggaggcatgc gtggtatccg tggagcagat ttccagtgct tccagcaagc ccgagccgtg
121     gggctgtcgg gcaccttccg ggctttcctg tcctctaggc tgcaggatct ctatagcatc
181     gtgcgccgtg ctgaccgggg gtctgtgccc atcgtcaacc tgaaggacga ggtgctatct
241     cccagctggg actccctgtt ttctggctcc agggtcaac tgcaacccgg ggcccgcatc
301     ttttcttttg acggcagaga tgtcctgaga cacccagcct ggccgcagaa gagcgtatgg
361     cacggctcgg accccagtgg gcggaggctg atggagagtt actgtgagac atggcgaact
421     gaaactactg ggctacagg tcaggcctcc tccctgctgt caggcaggct cctgaacag
481     aaagctgcga gctgccacaa cagctacatc gtcctgtgca ttgagaatag cttcatgacc
541     tctttctcca aa
```

SEQ ID NO: 155 (AAF69009):
```
  1     hthqdfqpvl hlvalntpls ggmrgirgad fqcfqqarav glsgtfrafl ssrlqdlysi
 61     vrradrgsvp ivnlkdevls pswdslfsgs qgqlqpgari fsfdgrdvlr hpawpqksvw
121     hgsdpsgrrl mesycetwrt ettgatgqas sllsgrlleq kaaschnsyi vlciensfmt
181     sfsk
```

ANTI-ANGIOGENIC PEPTIDES FOR TREATING OR PREVENTING ENDOMETRIOSIS

CROSS REFERENCE TO RELATED APPLICATIONS

This application is a continuation-in-part of PCT/US04/028476, which was filed on Aug. 30, 2004, which claims the benefit of U.S. Provisional Applications 60/499,264, filed on Aug. 29, 2003 and 60/539,213, filed on Jan. 26, 2004; the contents of each application is hereby incorporated by reference in its entirety.

STATEMENT OF RIGHTS

This invention was made with government support under Grant R01 CA064481 awarded by the National Institutes of Health. The government has certain rights in the invention.

BACKGROUND

Endometriosis is one of the most common gynecological disorders, affecting up to 15% of women of reproductive age. It is associated with severe pelvic pain, infertility, dysmenorrhea, dyspareunia, and several other symptoms such as intraperitoneal bleeding, back pain, constipation and/or diarrhea. It is a major threat to physical, psychological and social integrity of the patients.

Endometriosis is characterized by the implantation and growth of endometrial cells (which normally constitute the lining of the uterus) in extra-uterine sites such as the peritoneal cavity. Although the etiology and pathogenesis of endometriosis remain mainly unclear, the theory of retrograde menstruation is the most widely accepted to explain the presence of ectopic endometrial cells in the peritoneal cavity. However, this phenomenon occurs in most women and, thus, several other factors must be invoked to explain the implantation of endometrial cells and the subsequent development of endometriotic lesions. It is generally believed that initiation of endometriosis implies a complex cascade of events requiring several essential features. Retrogradely seeded endometrial cells must remain viable, be capable of adhering to the mesothelium and of proliferating. Local degradation of the extracellular matrix, as well as extensive vascularization, are also believed to play an essential role in promoting the invasion of the peritoneal cavity by endometrial cells. Furthermore, once implanted, ectopic endometrial cells must have the capacity to counteract the cytolytic action of the immune system. Indeed, this is supported by the observation of several immunological abnormalities in patients with endometriosis.

At present, direct visualization of the endometriotic lesions under surgical procedures (laparascopy or laparotomy) is the golden standard and the only reliable method available to diagnose endometriosis. However, this method is highly invasive (i.e. surgery under general anesthesia), costly (i.e. direct cost and indirect cost due to convalescence) and requires a well-trained surgeon who has the ability to identify endometriotic lesions with a variety of appearances. The type of lesions, their size and their localization will determine the stage of the disease (stage I minimal, stage II mild, stage III moderate, stage IV severe). However, there is still no clear consensus on how these parameters correlate with the stage of the disease and the prognostic of endometriosis. In addition, early or minimal endometriosis (which can involve microlesions) can be hardly diagnosed by surgical methods, as they are unlikely to be detected by direct visualization. Indeed, several studies have reported microscopic endometriotic lesions that were not detected laparoscopically. Because the diagnosis of endometriosis by surgical procedures is difficult, costly and invasive, in some cases, several physicians and patients tend to avoid it or at least seriously delay it. Hence, the length of time between the onset of symptoms and the diagnosis can be as long as 8 to 12 years. The possibility to diagnose endometriosis at an early stage would certainly improve the efficacy of the treatments, and reduce dramatically the number of years during which patients endure acute or chronic pain.

Effective methods to treat or prevent endometriosis are lacking, and thus, there is a need for new therapeutics.

SUMMARY OF THE INVENTION

The instant disclosure is based on the surprising finding that the N-terminal region of endostatin is responsible for its anti-angiogenic activity. Based on these findings, the disclosure features peptides comprising at least about 12 amino acids of SEQ ID Nos. 2 or 4. Other peptides comprise at least about 13, 14, 15, 16, 17, 18, 19, 20, 21, 22, 23, 24 or 25 amino acids of SEQ ID Nos. 2 or 4. Exemplary peptides are selected from the group consisting of SEQ ID Nos. 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124-131.

Also featured are pharmaceutical compositions comprising a pharmaceutically acceptable carrier and an effective amount of a peptide disclosed herein. Certain pharmaceutical compositions additionally comprise a second peptide that, for example, further stabilizes or provides other desirable characteristics. Other pharmaceutical compositions additionally comprise an effective amount of zinc. Devices, such as syringes and stents which comprise a peptide disclosed herein, are also described.

Further disclosed are nucleic acids encoding peptides, which comprise at least about 12 amino acids of SEQ ID Nos. 2 or 4, as well as pharmaceutical compositions comprising a disclosed nucleic acid in a suitable vector for expression of an effective amount of a peptide to a subject. Preferred nucleic acids comprise at least about 36, 54 or 60 nucleotides of SEQ ID Nos. 1, 3 or 5. Other preferred nucleic acids are selected from the group consisting of SEQ ID Nos.: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121 and 123.

Also provided are methods for using the disclosed therapeutics for treating or preventing endometriosis.

Other features and advantages of the disclosed anti-angiogenic peptides will become apparent based on an understanding of the following detailed description and claims.

BRIEF DESCRIPTION OF THE DRAWINGS

FIG. 2A is a graph showing treatment of LLC with murine Fc-endostatin and murine peptides P1, P2, P5, and P6 (mP1, mP2, mP5 and mP6, respectively); FIG. 2B are images of LLC sections showing CD31 staining; FIG. 2C is a graph showing the determination of vessel density (*p<0.015 vs.

PBS (control))

FIG. 3A is a schematic diagram of mP1 and mP1-H1/3A; FIG. 3B is a graph showing zinc binding to mP1 (SEQ ID NO: 4) and mP1-H1/3A (SEQ ID NO: 150); FIG. 3C is a graph showing treatment of LLC with mP1 and mP1-H1/3A; FIG. 3D shows images of LLC tumor sections stained with CD3 1; and FIG. 3E is a graph showing the determination of vessel density.

FIG. 6A is a graph showing quantification of Evan's blue dye extracted from the skin by incubation with formamide for 5 days at room temperature as measured at 620 nm.

FIG. 14 shows the nucleic acid and amino acid sequence of human and murine endostatin proteins.

DETAILED DESCRIPTION

Definitions

Figure 1:
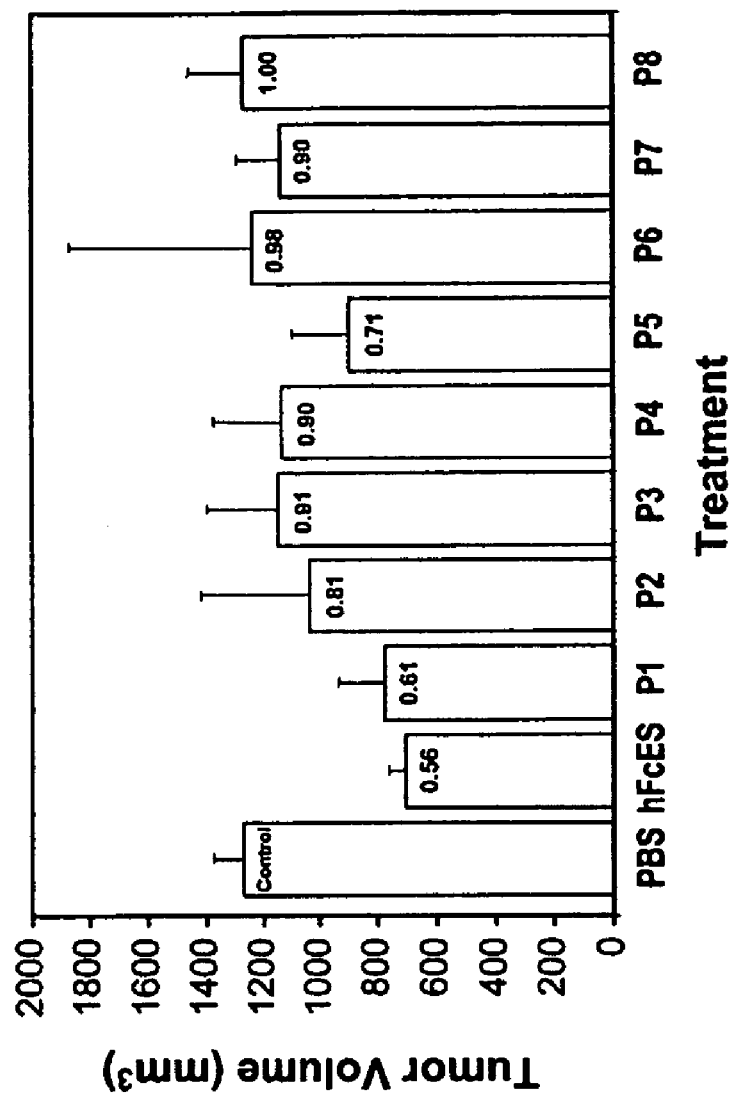
FIG. 1 is a graph showing treatment of human pancreatic carcinoma (BxPC3) with human endostatin peptides.

As used herein, the following terms and phrases shall have the meanings set forth below. Unless defined otherwise, all technical and scientific terms used herein have the same meaning as commonly understood to one of ordinary skill in the art.

The singular forms "a," "an," and "the" include plural reference unless the context clearly dictates otherwise.

The term "bioavailable" when referring to a compound is art-recognized and refers to a form of a compound that allows for it, or a portion of the amount of compound administered, to be absorbed by, incorporated to, or otherwise physiologically available to a subject or patient to whom it is administered.

As used herein, the term "composition" is intended to encompass a product comprising specified ingredients in specific amounts, as well as any product which results, directly or indirectly, from combination of the specific ingredients in the specified amounts.

"Conservative substitutions" are changes between amino acids of broadly similar molecular properties. For example, interchanges within the aliphatic group alanine, valine, leucine and isoleucine can be considered as conservative. Sometimes substitution of glycine for one of these can also be considered conservative. Other conservative interchanges include those within the aliphatic group aspartate and glutamate; within the amide group asparagine and glutamine; within the hydroxyl group serine and threonine; within the aromatic group phenylalanine, tyrosine and tryptophan; within the basic group lysine, arginine and histidine; and within the sulfur-containing group methionine and cysteine. Sometimes substitution within the group methionine and leucine can also be considered conservative. Preferred conservative substitution groups are aspartate-glutamate; asparagine-glutamine; valine-leucine-isoleucine; alanine-valine; phenylalanine-tyrosine; and lysine-arginine.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, and intrasternal injection and infusion.

A "patient," "subject" or "host" to be treated by the subject method may mean either a human or non-human animal.

The terms "polynucleotide", and "nucleic acid" are used interchangeably. They refer to a polymeric form of nucleotides of any length, either deoxyribonucleotides or ribonucleotides, or analogs thereof. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term "recombinant" polynucleotide means a polynucleotide of genomic, cDNA, semisynthetic, or synthetic origin which either does not occur in nature or is linked to another polynucleotide in a nonnatural arrangement. An "oligonucleotide" refers to a single stranded polynucleotide having less than about 100 nucleotides, less than about, e.g., 75, 50, 25, or 10 nucleotides.

The terms "polypeptide", "peptide" and "protein" (if single chain) are used interchangeably herein to refer to polymers of amino acids. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

The term "percent identical" refers to sequence identity between two amino acid sequences or between two nucleotide sequences. Identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Preferably, an alignment program that permits gaps in the sequence is utilized to align the sequences. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases. Databases with individual sequences are described in Methods in Enzymology, ed. Doolittle, supra. Databases include Genbank, EMBL, and DNA Database of Japan (DDBJ).

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof from one organ, or portion of the body, to another organ, or portion of the body. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "prophylactic" or "therapeutic" treatment is art-recognized and refers to administration of a drug to a host. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

The term "synthetic" is art-recognized and refers to production by in vitro chemical or enzymatic synthesis.

The terms "systemic administration," "administered systemically," "peripheral administration" and "administered peripherally" are art-recognized and refer to the administration of a subject composition, therapeutic or other material other than directly into the central nervous system, such that it enters the patient's system and, thus, is subject to metabolism and other like processes.

The term "therapeutic agent" is art-recognized and refers to any chemical moiety that is a biologically, physiologically, or pharmacologically active substance that acts locally or systemically in a subject. The term thus means any substance intended for use in the diagnosis, cure, mitigation, treatment or prevention of disease or in the enhancement of desirable physical or mental development and/or conditions in an animal or human.

The term "therapeutic effect" is art-recognized and refers to a local or systemic effect in animals, particularly mammals, and more particularly humans caused by a pharmacologically active substance. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compositions described herein may be administered in a sufficient amount to produce a at a reasonable benefit/risk ratio applicable to such treatment.

The term "treating" is art-recognized and refers to curing as well as ameliorating at least one symptom of any condition or disease or preventing a condition or disease from worsening.

The term "vector" refers to a nucleic acid capable of transporting another nucleic acid to which it has been linked. One type of vector which may be used in accord with the invention is an episome, i.e., a nucleic acid capable of extra-chromosomal replication. Other vectors include those capable of autonomous replication and expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double stranded DNA molecules which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

Exemplary Compositions

Peptides

Provided herein are peptides or polypeptides and variants thereof that inhibit, e.g., angiogenesis and thereby inhibit tumor growth and/or formation. Peptides may comprise an N-terminal amino acid sequence of an endostatin protein. The endostatin protein may be a mammalian protein, such as from a human, a non-human primate, a canine, a feline, an equine, a bovine, an ovine, a sheep, or a rodent (e.g., mouse or rat). A nucleotide sequence encoding human endostatin is set forth in SEQ ID NO: 152 and the protein encoded thereby is set forth as SEQ ID NO: 153 and is identical to GenBank Accession number AAF01310 except that it is lacking the initiator methionine of AAF01310. A nucleotide sequence encoding mouse endostatin is set forth in SEQ ID NO: 154 and the protein encoded thereby is set forth as SEQ ID NO: 155 and is identical to GenBank Accession number AAF69009. The nucleotide and amino acid sequences of other species are also publicly available.

In one embodiment, the peptide comprises about 5 to about 40 amino acids of the N-terminal region of an endostatin protein. The peptide may comprise from about 10 to about 30 or 35 amino acids or from about 20 to about 30 or 35 amino acids of the N-terminal region of an endostatin protein. For example, a peptide may comprise about amino acids 1 to about amino acids 35, 30, 25, 20, 15, or 10 of an endostatin protein, such as a protein having SEQ ID NO: 2 or 4. The amino acid sequences of these human and mouse peptides are HSHRDFQPVLHLVALNSPLSGGMRGIR (SEQ ID NO: 2) and HTHQDFQPVLHLVALNTPLSGGMRGIR (mP1; SEQ ID NO: 4), respectively. SEQ ID NO:2 is encoded by the following nucleic acid sequence:

```
cacagccaccgcgacttccagccggtgctccacctgg  (SEQ ID NO:1)
ttgcgctcaacagccccctgtcaggcggcatgcgggg
catccgc.

SEQ ID NO:4 is encoded by the following nucleic
acid sequence:
catactcatcaggactttcagccagtgctccacctgg  (SEQ ID NO:3)
tggcactgaacaccccctgtctggaggcatgcgtgg
tatccgt.
```

Peptides related to SEQ ID NO: 1 may also be used. One such peptide has the amino acid sequence HSHRDFQPVLHLVALNSPLSGGMRG (hP1; SEQ ID NO: 6), which is encoded by the nucleic acid sequence: catactcatcaggactttcagccagtgctccacctggtggcactgaacaccccctgtctggaggcatgcgtggt (SEQ ID NO: 5). SEQ ID NO: 6 does not contain the two most C-terminal amino acid residues in SEQ ID NO: 2. Further peptides of the invention may also lack one or more amino acids at the N- or C-terminus. For example, peptides may comprise an amino acid sequence starting at about amino acid 2, 3, 4, 5, 6, 7, 8, 9, or 10 of an endostatin protein or ending at about amino acids 20, 21, 22, 23, 24, 25 or 26. Illustrative peptides may comprise about amino acids 2 to 27; 3 to 27 or 1 to 20; 1 to 21; 1 to 22 of an endostatin protein, such as the following peptides derived from SEQ ID NO: 2:

| Sequence | |
|---|---|
| SHRDFQPVLHLVALNSPLSGGMRGIR; | (SEQ ID NO:8) |
| HRDFQPVLHLVALNSPLSGGMRGIR; | (SEQ ID NO:10) |
| RDFQPVLHLVALNSPLSGGMRGIR; | (SEQ ID NO:12) |
| DFQPVLHLVALNSPLSGGMRGIR; | (SEQ ID NO:14) |
| FQPVLHLVALNSPLSGGMRGIR; | (SEQ ID NO:16) |
| QPVLHLVALNSPLSGGMRGIR; | (SEQ ID NO:18) |
| PVLHLVALNSPLSGGMRGIR; | (SEQ ID NO:20) |
| VLHLVALNSPLSGGMRGIR; | (SEQ ID NO:22) |
| LHLVALNSPLSGGMRGIR; | (SEQ ID NO:24) |
| HLVALNSPLSGGMRGIR; | (SEQ ID NO:26) |
| VALNSPLSGGMRGIR; | (SEQ ID NO:30) |
| ALNSPLSGGMRGIR; | (SEQ ID NO:32) |
| LNSPLSGGMRGIR; | (SEQ ID NO:34) |
| NSPLSGGMRGIR; | (SEQ ID NO:36) |
| HSHRDFQPVLHLVALNSPLSGGMRGI; | (SEQ ID NO:38) |
| HSHRDFQPVLHLVALNSPLSGGMR; | (SEQ ID NO:40) |
| HSHRDFQPVLHLVALNSPLSGGM; | (SEQ ID NO:42) |
| HSHRDFQPVLHLVALNSPLSGG; | (SEQ ID NO:44) |
| HSHRDFQPVLHLVALNSPLSG; | (SEQ ID NO:46) |
| HSHRDFQPVLHLVALNSPLS; | (SEQ ID NO:48) |
| HSHRDFQPVLHLVALNSPL; | (SEQ ID NO:50) |
| HSHRDFQPVLHLVALNSP; | (SEQ ID NO:52) |
| HSHRDFQPVLHLVALNS; | (SEQ ID NO:54) |
| HSHRDFQPVLHLVALN; | (SEQ ID NO:56) |
| HSHRDFQPVLHLVAL; | (SEQ ID NO:58) |
| HSHRDFQPVLHLVA; | (SEQ ID NO:60) |
| HSHRDFQPVLHLV; | (SEQ ID NO:62) |
| HSHRDFQPVLHL; | (SEQ ID NO:64) |
| THQDFQPVLHLVALNTPLSGGMRGIR; | (SEQ ID NO:66) |
| HQDFQPVLHLVALNTPLSGGMRGIR; | (SEQ ID NO:68) |
| QDFQPVLHLVALNTPLSGGMRGIR; | (SEQ ID NO:70) |
| DFQPVLHLVALNTPLSGGMRGIR; | (SEQ ID NO:72) |
| FQPVLHLVALNTPLSGGMRGIR; | (SEQ ID NO:74) |
| QPVLHLVALNTPLSGGMRGIR; | (SEQ ID NO:76) |
| PVLHLVALNTPLSGGMRGIR; | (SEQ ID NO:78) |
| VLHLVALNTPLSGGMRGIR; | (SEQ ID NO:80) |
| LHLVALNTPLSGGMRGIR; | (SEQ ID NO:82) |
| HLVALNTPLSGGMRGIR; | (SEQ ID NO:84) |
| LVALNTPLSGGMRGIR; | (SEQ ID NO:86) |

-continued

| | |
|---|---|
| VALNTPLSGGMRGIR; | (SEQ ID NO:88) |
| ALNTPLSGGMRGIR; | (SEQ ID NO:90) |
| LNTPLSGGMRGIR; | (SEQ ID NO:92) |
| NTPLSGGMRGIR; | (SEQ ID NO:94) |
| HTHQDFQPVLHLVALNTPLSGGMRGI; | (SEQ ID NO:96) |
| HTHQDFQPVLHLVALNTPLSGGMRG; | (SEQ ID NO:98) |
| HTHQDFQPVLHLVALNTPLSGGMR; | (SEQ ID NO:100) |
| HTHQDFQPVLHLVALNTPLSGGM; | (SEQ ID NO:102) |
| HTHQDFQPVLHLVALNTPLSGG; | (SEQ ID NO:104) |
| HTHQDFQPVLHLVALNTPLSG; | (SEQ ID NO:106) |
| HTHQDFQPVLHLVALNTPLS; | (mP1-20; SEQ ID NO:108) |
| HTHQDFQPVLHLVALNTPL; | (SEQ ID NO:110) |
| HTHQDFQPVLHLVALNTP; | (SEQ ID NO:112) |
| HTHQDFQPVLHLVALNT; | (SEQ ID NO:114) |
| HTHQDFQPVLHLVALN; | (SEQ ID NO:116) |
| HTHQDFQPVLHLVAL; | (mP1-15; SEQ ID NO:118) |
| HTHQDFQPVLHLVA; | (SEQ ID NO:120) |
| HTHQDFQPVLHLV; | (SEQ ID NO:122) |
| HTHQDFQPVLHL; | (SEQ ID NO:124) |
| HSHRDFVALNSPLSGGMRGIR; | (SEQ ID NO:125) |
| HSHRDFQPVLHLLSGGMRGIR; | (SEQ ID NO:126) |
| QPVLHLVALNTPLSGGMRGIR; | (SEQ ID NO:127) |
| HTHQDFVALNTPLSGGMRGIR; and | (SEQ ID NO:128) |
| HTHQDFQPVLHLLSGGMRGLR. | (SEQ ID NO:129) |

Peptides having an amino acid sequence falling within the following degenerate sequences can be used: HXaaHXaaDFQPVLHLVALNXaaPLSGGMRGIR (SEQ ID NO: 130); and HXaaHXaaDFQPVLHLVALNXaaPLSG (SEQ ID NO: 131), wherein Xaa is any amino acid.

Preferred peptides comprise His 1 and 3. Other preferred peptides comprise His 1, 3 and 11. Peptides may be linked to $Zn^{2+}$ (see below).

Peptides may also comprise, consist of or consist essentially of any of the amino acid sequences described herein. Yet other peptides comprise, consist of or consist essentially of an amino acid sequence that has at least about 70%, 80%, 90%, 95%, 98% or 99% identity or homology with an N-terminal endostatin peptide. For example, peptides that differ from a sequence in a naturally occurring endostatin protein in about 1, 2, 3, 4, 5 or more amino acids are also contemplated. The differences may be substitutions, e.g., conservative substitutions, deletions or additions. The differences are preferably in regions that are not significantly conserved among different species. Such regions can be identified by aligning the amino acid sequences of endostatin proteins from various animal species. For example, amino acids 2, 4, and 17 of an endostatin protein or peptide having, e.g., SEQ ID NO: 2, 4, or 6, and the highlighted amino acids in e.g. SEQ ID NOs: 8, 10, 12, 30, 32, or 34 can be substituted, since these amino acids differ in the human and mouse sequences. These amino acids can be substituted, e.g., with those found in another species. Amino acid 9 can also be substituted, since that one is different in the *Gallus gallus* species. Other amino acids that may be substituted, inserted or deleted at these or other locations can be identified by mutagenesis studies coupled with biological assays. Preferably the histidines at positions 1, 3 and optionally 11 are not substituted.

Also encompassed herein are anti-endometriosis peptides that are fused to a heterologous peptide, such as a peptide that can be used for detecting; purifying; stabilizing; or solubilizing the endostatin peptide.

A peptide may by linked to an immunoglobulin (Ig) constant heavy or light chain domain or portion thereof. For example, a peptide may be linked to a CH1, CH2 and/or CH3 domain of a heavy chain. If the constant region is from a light chain, it may be from a kappa or lambda light chain. If the constant region is from a heavy chain, it may be from an antibody of any one of the following classes of antibodies: IgG, IgA, IgE, IgD, and IgM. IgG may be IgG1, IgG2, IgG3 or IgG4. The constant domain may be an Fc fragment. The constant domain may be from a mammalian antibody, e.g., a human antibody. Soluble receptor-IgG fusion proteins are common immunological reagents and methods for their construction are known in the art (see e.g., U.S. Pat. Nos. 5,225, 538, 5,726,044; 5,707,632; 750,375, 5,925,351, 6,406,697 and Bergers et al. *Science* 1999 284: 808-12). Preferred as immunoglobulin is the constant part of the heavy chain of human IgG, particularly IgG1, where dimerization between two heavy chains takes place at the hinge region. It is recognized that inclusion of the CH2 and CH3 domains of the Fc region as part of the fusion polypeptide increases the in vivo circulation half-life of the polypeptide comprising the Fc region, and that of the oligomer or dimer comprising the polypeptide.

An Fc portion of human IgG1 which includes the hinge region, and domains CH2 and CH3 has the nucleotide sequence 5' gag ccc aaa tct tgt gac aaa act cac aca tgc cca ccg tgc cca gca cct gaa ctc ctg ggg gga ccg tca gtc ttc ctc ttc ccc cca aaa ccc aag gac acc ctc atg atc tcc cgg acc cct gag gtc aca tgc gtg gtg gtg gac gtg agc cac gaa gac cct gag gtc aag ttc aac tgg tac gtg gac ggc gtg gag gtg cat aat gcc aag aca aag ccg cgg gag gag cag tac aac agc acg tac cgt gtg gtc agc gtc ctc acc gtc ctg cac cag gac tgg ctg aat ggc aag gag tac aag tgc aag gtc tcc aac aaa gcc ctc cca gcc ccc atc gag aaa acc atc tcc aaa gcc aaa ggg cag ccc cga gaa cca cag gtg tac acc ctg ccc cca tcc cgg gat gag ctg acc aag aac cag gtc agc ctg acc tgc ctg gtc aaa ggc ttc tat ccc agc gac atc gcc gtg gag tgg gag agc aat ggg cag ccg gag aac aac tac aag acc acg cct ccc gtg ctg gac tcc gac ggc tcc ttc ttc ctc tac agc aag ctc acc gtg gac aag agc agg tgg cag cag ggg aac gtc ttc tca tgc tcc gtg atg cat gag gct ctg cac aac cac tac acg cag aag agc ctc tcc ctg tct ccg ggt aaa tga 3' (SEQ ID NO: 132), which encodes a peptide having the amino acid sequence: Glu Pro Lys Ser Cys Asp Lys Thr His Thr Cys Pro Pro Cys Pro Ala Pro Glu Leu Leu Gly Gly Pro Ser Val Phe Leu Phe Pro Pro Lys Pro Lys Asp Thr Leu Met Ile Ser Arg Thr Pro Glu Val Thr Cys Val Val Val Asp Val Ser His Glu Asp Pro Glu Val Lys Phe Asn Trp Tyr Val Asp Gly Val Glu Val His Asn Ala Lys Thr Lys Pro Arg Glu Glu Gln Tyr Asn Ser Thr Tyr Arg Val Val Ser Val Leu Thr Val Leu His Gln Asp Trp Leu Asn Gly Lys Glu Tyr Lys Cys Lys Val Ser Asn Lys Ala Leu Pro Ala Pro Ile Glu Lys Thr Ile Ser Lys Ala Lys Gly Gln Pro Arg Glu Pro Gln Val Tyr Thr Leu Pro Pro Ser Arg Asp Glu Leu Thr Lys Asn Gln Val Ser Leu Thr Cys Leu Val Lys Gly Phe Tyr Pro Ser Asp Ile Ala Val Glu Trp Glu Ser Asn Gly Gln Pro Glu Asn Asn Tyr Lys Thr Thr Pro Pro Val Leu Asp Ser Asp Gly Ser Phe Phe Leu Tyr Ser Lys Leu Thr Val Asp Lys Ser Arg Trp Gln Gln Gly Asn Val Phe Ser Cys Ser Val Met His Glu Ala Leu His Asn His Tyr Thr Gln Lys Ser Leu Ser Leu Ser Pro Gly Lys (SEQ ID NO: 133).

Constant Ig domains may also contain one or more mutations that reduce or eliminate one or more effector function, e.g., binding to Fc receptors and complement activation (see, e.g., S. Morrison, Annu. Rev. Immunol., 10, pp. 239-65 (1992); Duncan and Winter (1988) Nature 332: 738-740; and Xu et al. (1994) J Biol. Chem. 269: 3469-3474). For example, mutations of amino acids corresponding to Leu 235 and Pro 331 of human IgGI to Glu and Ser, respectively, are provided. Such constructs are further described in U.S. Pat. No. 6,656,728.

The constant Ig domain may be linked to the N-terminus or C-terminus of a peptide.

The peptide may also be linked to a linker sequence with a thrombin cleavage site, such as between the peptide and an immunoglobulin domain. An exemplary nucleotide sequence encoding such a site has the following nucleotide sequence: 5' tct aga ggt ggt cta gtg ccg cgc ggc agc ggt tcc ccc ggg ttg cag 3' (SEQ ID NO: 134), which encodes a peptide having the amino acid sequence: Ser Arg Gly Gly Leu Val Pro Arg Gly Ser Gly Ser Pro Gly Leu Gln (SEQ ID NO: 135).

A peptide may also be fused to a signal sequence. For example, when prepared recombinantly, a nucleic acid encoding the peptide may be linked at its 5' end to a signal sequence, such that the peptide is secreted from the cell.

Peptides may be used as a substantially pure preparation, e.g., wherein at least about 90% of the peptides in the preparation are the desired peptide. Compositions comprising at least about 50%, 60%, 70%, or 80% of the desired peptide may also be used.

Peptides may be denatured or non-denatured and may be aggregated or non-aggregated as a result thereof. Peptides can be denatured according to methods known in the art.

Peptides may be conjugated to zinc. Thus, peptides may be in a composition comprising $Zn^{2+}$, e.g., in sufficient quantities that most of the peptides are conjugated to one or more $Zn^{2+}$ molecule. Binding of $Zn^{2+}$ to a peptide can be demonstrated by the following assay. Zinc and peptide solutions are mixed, optionally incubated together, and then dialyzed to remove the zinc that is not bound to the peptides. Detection of zinc in the peptide solution can then be performed by atomic absorption.

Yet other peptides that are encompassed herein are those that comprise modified amino acids. Exemplary peptides are derivative peptides that may be one modified by glycosylation, pegylation, phosphorylation or any similar process that retains at least one biological function of the peptide from which it was derived.

Peptides may also comprise one or more non-naturally occurring amino acids. For example, nonclassical amino acids or chemical amino acid analogs can be introduced as a substitution or addition into peptides. Non-classical amino acids include, but are not limited to, the D-isomers of the common amino acids, 2,4-diaminobutyric acid, alpha-amino isobutyric acid, 4-aminobutyric acid, Abu, 2-amino butyric acid, gamma-Abu, epsilon-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, beta-alanine, fluoro-amino acids, designer amino acids such as beta-methyl amino acids, Calpha-methyl amino acids, Nalpha-methyl amino acids, and amino acid analogs in general. Furthermore, the amino acid can be D (dextrorotary) or L (levorotary).

In other specific embodiments, branched versions of the peptides listed herein are provided, e.g., by substituting one or more amino acids within the sequence with an amino acid or amino acid analog with a free side chain capable of forming a peptide bond with one or more amino acids (and thus capable of forming a "branch"). Cyclical peptides are also contemplated.

Also included are peptide derivatives which are differentially modified during or after synthesis, e.g., by benzylation, glycosylation, acetylation, phosphorylation, amidation, pegylation, derivatization by known protecting/blocking groups, proteolytic cleavage, linkage to an antibody molecule or other cellular ligand, etc. In specific embodiments, the peptides are acetylated at the N-terminus and/or amidated at the C-terminus.

Also provided are derivatives of endostatin peptides, such as chemically modified peptides and peptidomimetics. Peptidomimetics are compounds based on, or derived from, peptides and proteins. Peptidomimetics can be obtained by structural modification of known peptide sequences using unnatural amino acids, conformational restraints, isosteric replacement, and the like. The subject peptidomimetics constitute the continuum of structural space between peptides and non-peptide synthetic structures; peptidomimetics may be useful, therefore, in delineating pharmacophores and in helping to translate peptides into nonpeptide compounds with the activity of the parent peptides.

Moreover, mimetopes of the subject peptides can be provided. Such peptidomimetics can have such attributes as being non-hydrolyzable (e.g., increased stability against proteases or other physiological conditions which degrade the corresponding peptide), increased specificity and/or potency for stimulating cell differentiation. For illustrative purposes, peptide analogs can be generated using, for example, benzodiazepines (e.g., see Freidinger et al. in Peptides: Chemistry and Biology, G. R. Marshall ed., ESCOM Publisher: Leiden, Netherlands, 1988), substituted gama lactam rings (Garvey et al. in *Peptides: Chemistry and Biology*, G. R. Marshall ed., ESCOM Publisher: Leiden, Netherlands, 1988, p123), C-7 mimics (Huffman et al. in *Peptides: Chemistry and Biologyy*, G. R. Marshall ed., ESCOM Publisher: Leiden, Netherlands, 1988, p. 105), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:1231), β-aminoalcohols (Gordon et al. (1985) *Biochem Biophys Res Commun* 126:419; and Dann et al. (1986) *Biochem Biophys Res Commun* 134:71), diaminoketones (Natarajan et al. (1984) *Biochem Biophys Res Commun* 124:141), and methyleneamino-modifed (Roark et al. in *Peptides: Chemistry and Biology*, G. R. Marshall ed., ESCOM Publisher: Leiden, Netherlands, 1988, p134). Also, see generally, Session III: Analytic and synthetic methods, in in *Peptides: Chemistry and Biology*, G. R. Marshall ed., ESCOM Publisher: Leiden, Netherlands, 1988).

In addition to a variety of sidechain replacements which can be carried out to generate peptidomimetics, the description specifically contemplates the use of conformationally restrained mimics of peptide secondary structure. Numerous surrogates have been developed for the amide bond of peptides. Frequently exploited surrogates for the amide bond include the following groups (i) trans-olefins, (ii) fluoroalkene, (iii) methyleneamino, (iv) phosphonamides, and (v) sulfonamides.

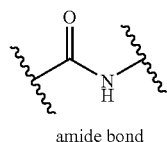

amide bond

Examples of Surrogates:

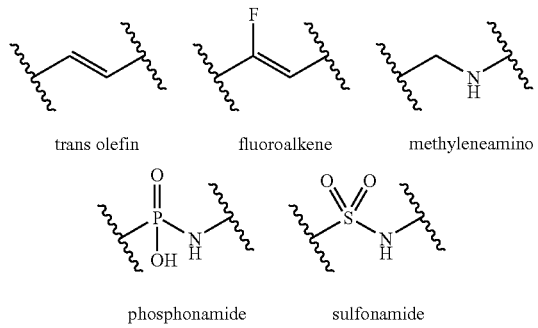

trans olefin    fluoroalkene    methyleneamino phosphonamide    sulfonamide

Additionally, peptidomimietics based on more substantial modifications of the backbone of a peptide can be used. Peptidomimetics which fall in this category include (i) retro-inverso analogs, and (ii) N-alkyl glycine analogs (so-called peptoids).

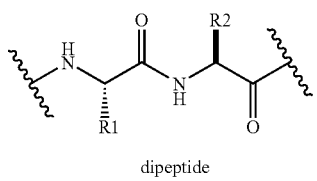

dipeptide

Examples of Analogs:

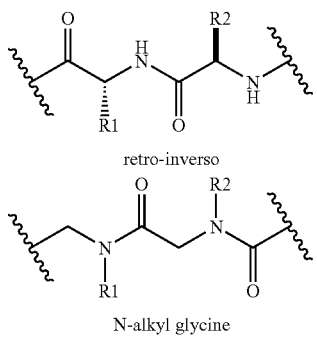

retro-inverso

N-alkyl glycine

Furthermore, the methods of combinatorial chemistry are being brought to bear, on the development of new peptidomimetics. For example, one embodiment of a so-called "peptide morphing" strategy focuses on the random generation of a library of peptide analogs that comprise a wide range of peptide bond substitutes.

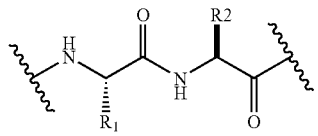

dipeptide peptide morphing new backbone element

In an exemplary embodiment, the peptidomimetic can be derived as a retro-inverso analog of the peptide. Such retro-inverso analogs can be made according to the methods known in the art, such as that described by the Sisto et al. U.S. Pat. No. 4,522,752. A retro-inverso analog can be generated as described, e.g., in WO 00/01720. It will be understood that a mixed peptide, e.g. including some normal peptide linkages, may be generated. As a general guide, sites which are most susceptible to proteolysis are typically altered, with less susceptible amide linkages being optional for mimetic switching. The final product, or intermediates thereof, can be purified by HPLC.

Peptides may comprise at least one amino acid or every amino acid that is a D stereoisomer. Other peptides may comprise at least one amino acid that is reversed. The amino acid that is reversed may be a D stereoisomer. Every amino acid of a peptide may be reversed and/or every amino acid may be a D stereoisomer.

In another illustrative embodiment, a peptidomimetic can be derived as a retro-enantio analog of a peptide. Retro-enantio analogs such as this can be synthesized with commercially available D-amino acids (or analogs thereof) and standard solid- or solution-phase peptide-synthesis techniques, as described, e.g., in WO 00/01720. The final product may be purified by HPLC to yield the pure retro-enantio analog.

In still another illustrative embodiment, trans-olefin derivatives can be made for the subject peptide. Trans-olefin analogs can be synthesized according to the method of Y. K. Shue et al. (1987) *Tetrahedron Letters* 28:3225 and as described in WO 00/01720. It is further possible to couple pseudodipeptides synthesized by the above method to other pseudodipeptides, to make peptide analogs with several olefinic functionalities in place of amide functionalities.

Still another class of peptidomimetic derivatives include the phosphonate derivatives. The synthesis of such phosphonate derivatives can be adapted from known synthesis schemes. See, for example, Loots et al. in *Peptides: Chemistry and Biology*, (Escom Science Publishers, Leiden, 1988, p. 118); Petrillo et al. in *Peptides: Structure and Function* (Proceedings of the 9th American Peptide Symposium, Pierce Chemical Co. Rockland, Ill., 1985).

Many other peptidomimetic structures are known in the art and can be readily adapted for use in the subject peptidomimetics. To illustrate, a peptidomimetic may incorporate the 1-azabicyclo[4.3.0]nonane surrogate (see Kim et al. (1997) *J. Org. Chem.* 62:2847), or an N-acyl piperazic acid (see Xi et al. (1998) *J. Am. Chem. Soc.* 120:80), or a 2-substituted piperazine moiety as a constrained amino acid analogue (see Williams et al. (1996) *J. Med. Chem.* 39:1345-1348). In still other embodiments, certain amino acid residues can be replaced with aryl and bi-aryl moieties, e.g., monocyclic or bicyclic aromatic or heteroaromatic nucleus, or a biaromatic, aromatic-heteroaromatic, or biheteroaromatic nucleus.

The subject peptidomimetics can be optimized by, e.g., combinatorial synthesis techniques combined with high throughput screening.

Moreover, other examples of mimetopes include, but are not limited to, protein-based compounds, carbohydrate-based compounds, lipid-based compounds, nucleic acid-based compounds, natural organic compounds, synthetically derived organic compounds, anti-idiotypic antibodies and/or catalytic antibodies, or fragments thereof. A mimetope can be obtained by, for example, screening libraries of natural and synthetic compounds for compounds capable of inhibiting angiogenesis and/or tumor growth. A mimetope can also be obtained, for example, from libraries of natural and synthetic compounds, in particular, chemical or combinatorial libraries (i.e., libraries of compounds that differ in sequence or size but that have the same building blocks). A mimetope can also be obtained by, for example, rational drug design. In a rational drug design procedure, the three-dimensional structure of a compound of the present invention can be analyzed by, for example, nuclear magnetic resonance (NMR) or x-ray crystallography. The three-dimensional structure can then be used to predict structures of potential mimetopes by, for example, computer modelling. The predicted mimetope structures can then be produced by, for example, chemical synthesis, recombinant DNA technology, or by isolating a mimetope from a natural source (e.g., plants, animals, bacteria and fungi).

"Peptides, variants and derivatives thereof" or "peptides and analogs thereof" are included in "peptide therapeutics" and is intended to include any of the peptides or modified forms thereof, e.g., peptidomimetics, described herein. Preferred peptide therapeutics have anti-angiogenic activity. For example, they may reduce or inhibit angiogenesis by a factor of at least about 50%, 2 fold, 5 fold, 10 fold, 30 fold or 100 fold, as determined, e.g., in an assay described herein.

Nucleic Acids

Also disclosed are nucleic acids encoding the peptides described above. Preferred nucleic acids are as follows:

```
cacagccaccgcgacttccagccggtgctccacc    (SEQ ID NO:1)
tggttgcgctcaacagcccctgtcaggcggcat
gcggggcatccgc;

catactcatcaggactttcagccagtgctccacc    (SEQ ID NO:3)
tggtggcactgaacaccccctgtctggaggcat
gcgtggtatccgt;

catactcatcaggactttcagccagtgctccacc    (SEQ ID NO:5)
tggtggcactgaacaccccctgtctggaggcat
gcgtggt;

agccaccgcgacttccagccggtgctccacctgg    (SEQ ID NO:7)
ttgcgctcaacagcccctgtcaggcggcatgcg
gggcatccgc;

caccgcgacttccagccggtgctccacctggttg    (SEQ ID NO:9)
cgctcaacagcccctgtcaggcggcatgcgggg
catccgc;

cgcgacttccagccggtgctccacctggttgcgc    (SEQ ID NO:11)
tcaacagcccctgtcaggcggcatgcggggcat
ccgc;

gacttccagccggtgctccacctggttgcgctca    (SEQ ID NO:13)
acagcccctgtcaggcggcatgcggggcatccg
c;

ttccagccggtgctccacctggttgcgctcaaca    (SEQ ID NO:15)
gcccctgtcaggcggcatgcggggcatccgc;

cagccggtgctccacctggttgcgctcaacagcc    (SEQ ID NO:17)
ccctgtcaggcggcatgcggggcatccgc;

ccggtgctccacctggttgcgctcaacagcccc    (SEQ ID NO:19)
tgtcaggcggcatgcggggcatccgc;

gtgctccacctggttgcgctcaacagcccctgt    (SEQ ID NO:21)
caggcggcatgcggggcatccgc;

ctccacctggttgcgctcaacagcccctgtcag    (SEQ ID NO:23)
gcggcatgcggggcatccgc;

cacctggttgcgctcaacagcccctgtcaggcg    (SEQ ID NO:25)
gcatgcggggcatccgc;

ctggttgcgctcaacagcccctgtcaggcggca    (SEQ ID NO:27)
tgcggggcatccgc;

gttgcgctcaacagcccctgtcaggcggcatgc    (SEQ ID NO:29)
ggggcatccgc;

gcgctcaacagcccctgtcaggcggcatgcggg    (SEQ ID NO:31)
gcatccgc;

ctcaacagcccctgtcaggcggcatgcggggca    (SEQ ID NO:33)
tccgc;

aacagcccctgtcaggcggcatgcggggcatcc    (SEQ ID NO:35)
gc;

cacagccaccgcgacttccagccggtgctccacc    (SEQ ID NO:37)
tggttgcgctcaacagcccctgtcaggcggcat
gcggggcatc;

cacagccaccgcgacttccagccggtgctccacc    (SEQ ID NO:39)
tggttgcgctcaacagcccctgtcaggcggcat
gcgg;

cacagccaccgcgacttccagccggtgctccacc    (SEQ ID NO:41)
tggttgcgctcaacagcccctgtcaggcggcat
g;

cacagccaccgcgacttccagccggtgctccacc    (SEQ ID NO:43)
tggttgcgctcaacagcccctgtcaggcggc;

cacagccaccgcgacttccagccggtgctccacc    (SEQ ID NO:45)
tggttgcgctcaacagcccctgtcaggc;

cacagccaccgcgacttccagccggtgctccacc    (SEQ ID NO:47)
tggttgcgctcaacagcccctgtca;

cacagccaccgcgacttccagccggtgctccacc    (SEQ ID NO:49)
tggttgcgctcaacagcccctg;

cacagccaccgcgacttccagccggtgctccacc    (SEQ ID NO:51)
tggttgcgctcaacagcccc;

cacagccaccgcgacttccagccggtgctccacc    (SEQ ID NO:53)
tggttgcgctcaacagc;

cacagccaccgcgacttccagccggtgctccacc    (SEQ ID NO:55)
tggttgcgctcaac;

cacagccaccgcgacttccagccggtgctccacc    (SEQ ID NO:57)
tggttgcgctc;

cacagccaccgcgacttccagccggtgctccacc    (SEQ ID NO:59)
tggttgcg;

cacagccaccgcgacttccagccggtgctccacc    (SEQ ID NO:61)
tggtt;
```

-continued

```
cacagccaccgcgacttccagccggtgctccacc    (SEQ ID NO:63)
tg;

actcatcaggactttcagccagtgctccacctgg    (SEQ ID NO:65)
tggcactgaacacccccctgtctggaggcatgcg
tggtatccgt;

catcaggactttcagccagtgctccacctggtgg    (SEQ ID NO:67)
cactgaacacccccctgtctggaggcatgcgtgg
tatccgt;

caggactttcagccagtgctccacctggtggcac    (SEQ ID NO:69)
tgaacacccccctgtctggaggcatgcgtggtat
ccgt;

gactttcagccagtgctccacctggtggcactga    (SEQ ID NO:71)
acacccccctgtctggaggcatgcgtggtatccg
t;

tttcagccagtgctccacctggtggcactgaaca    (SEQ ID NO:73)
cccccctgtctggaggcatgcgtggtatccgt;

cagccagtgctccacctggtggcactgaacaccc    (SEQ ID NO:75)
ccctgtctggaggcatgcgtggtatccgt;

ccagtgctccacctggtggcactgaacaccccc    (SEQ ID NO:77)
tgtctggaggcatgcgtggtatccgt;

gtgctccacctggtggcactgaacacccccctgt    (SEQ ID NO:79)
ctggaggcatgcgtggtatccgt;

ctccacctggtggcactgaacacccccctgtctg    (SEQ ID NO:81)
gaggcatgcgtggtatccgt;

cacctggtggcactgaacacccccctgtctggag    (SEQ ID NO:83)
gcatgcgtggtatccgt;

ctggtggcactgaacacccccctgtctggaggca    (SEQ ID NO:85)
tgcgtggtatccgt;

gtggcactgaacacccccctgtctggaggcatgc    (SEQ ID NO:87)
gtggtatccgt;

gcactgaacacccccctgtctggaggcatgcgtg    (SEQ ID NO:89)
gtatccgt;

ctgaacacccccctgtctggaggcatgcgtggta    (SEQ ID NO:91)
tccgt;

aacacccccctgtctggaggcatgcgtggtatcc    (SEQ ID NO:93)
gt;

catactcatcaggactttcagccagtgctccacc    (SEQ ID NO:95)
tggtggcactgaacacccccctgtctggaggcat
gcgtggtatc;

caractcatcaggactttcagccagtgctccacc    (SEQ ID NO:97)
tggtggcactgaacacccccctgtctggaggcat
gcgtggt;

catactcatcaggactttcagccagtgctccacc    (SEQ ID NO:99)
tggtggcactgaacacccccctgtctggaggcat
gcgt;

catactcatcaggactttcagccagtgctccacc    (SEQ ID NO:101)
tggtggcactgaacacccccctgtctggaggcat
g;

catactcatcaggacutcagccagtgctccacct    (SEQ ID NO:103)
ggtggcactgaacacccccctgtctggaggc;

catactcatcaggactttcagccagtgctccacc    (SEQ ID NO:105)
tggtggcactgaacacccccctgtctgga;

catactcatcaggactttcagccagtgctccacc    (SEQ ID NO:107)
tggtggcactgaacacccccctgtct;

catactcatcaggactttcagccagtgctccacc    (SEQ ID NO:109)
tggtggcactgaacacccccctg;

catactcatcaggactttcagccagtgctccacc    (SEQ ID NO:111)
```

-continued

```
tggtggcactgaacacccccc;

catactcatcaggactttcagccagtgctccacc    (SEQ ID NO:113)
tggtggcactgaacacacc;

catactcatcaggactttcagccagtgctccacc    (SEQ ID NO:115)
tggtggcactgaac;

catactcatcaggactttcagccagtgctccacc    (SEQ ID NO:117)
tggtggcactg;

catactcatcaggactttcagccagtgctccacc    (SEQ ID NO:119)
tggtggca;

catactcatcaggactttcagccagtgctccacc    (SEQ ID NO:121)
tggtg;
and catactcatcaggactttcagccagtgctccacc    (SEQ ID NO:123)
tg.
```

Nucleic acids include vectors, such as expression vectors for producing a peptide, e.g., viral vectors. Also encompassed herein are cells comprising a nucleic acid encoding a peptide described herein and methods for producing peptides comprising culturing these cells to produce a peptide. These methods can be used of producing recombinant peptides or for expression of a petpide in a cell, e.g., in a cell of a subject.

Appropriate vectors may be introduced into host cells using well known techniques such as infection, transduction, transfection, transvection, electroporation and transformation. The vector may be, for example, a phage, plasmid, viral or retroviral vector. Retroviral vectors may be replication competent or replication defective. In the latter case, viral propagation generally will occur only in complementing host cells.

The vector may contain a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

Preferred vectors comprise cis-acting control regions to the polynucleotide of interest. Appropriate trans-acting factors may be supplied by the host, supplied by a complementing vector or supplied by the vector itself upon introduction into the host.

In certain embodiments, the vectors provide for specific expression, which may be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating site at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline, kanamycin, or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells; insect cells such as *Drosophila* S2 and Sf9 cells; animal cells such as CHO, COS and Bowes melanoma cells; and plant cells. Appropriate culture mediums and conditions for the above-described host cells are known in the art.

Among vectors preferred for use in bacteria include pQE70, pQE60 and pQE9, pQE10 available from Qiagen; pBS vectors, Phagescript vectors, Bluescript vectors, pNH8A, pNH16a, pNH18A, pNH46A available from Stratagene; pET series of vectors available from Novagen; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Among known bacterial promoters suitable for use in the present invention include the *E. coli* lacI and lacZ promoters, the T3, T5 and T7 promoters, the gpt promoter, the lambda PR and PL promoters, the trp promoter and the xyl/tet chimeric promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals (for example, Davis, et al., *Basic Methods In Molecular Biology* (1986)).

Transcription of DNA encoding the polypeptides of the present invention by higher eukaryotes may be increased by inserting an enhancer sequence into the vector. Enhancers are cis-acting elements of DNA, usually about from 10 to 300 nucleotides that act to increase transcriptional activity of a promoter in a given host cell-type. Examples of enhancers include the SV40 enhancer, which is located on the late side of the replication origin at nucleotides 100 to 270, the cytomegalovirus early promoter enhancer, the polyoma enhancer on the late side of the replication origin, and adenovirus enhancers.

A recombinant soluble form of a polypeptide of the present invention may also be produced, e.g., by deleting at least a portion of the transmembrane domain, such that the protein is not capable to localize itself to a cell membrane. Also within the scope of the invention are nucleic acids encoding splice variants or nucleic acids representing transcripts synthesized from an alternative transcriptional initiation site, such as those whose transcription was initiated from a site in an intron. Such homologues can be cloned by hybridization or PCR using standard methods known in the art.

The polynucleotide sequence may also encode for a leader sequence, e.g., the natural leader sequence or a heterologous leader sequence. Alternatively, the nucleic acid can be engineered such that the natural leader sequence is deleted and a heterologous leader sequence inserted in its place. The term "leader sequence" is used interchangeably herein with the term "signal peptide". For example, the desired DNA sequence may be fused in the same reading frame to a DNA sequence which aids in expression and secretion of the polypeptide from the host cell, for example, a leader sequence which functions as a secretory sequence for controlling transport of the polypeptide from the cell. The protein having a leader sequence is a preprotein and may have the leader sequence cleaved by the host cell to form the mature form of the protein.

For secretion of the translated polypeptide into the lumen of the endoplasmic reticulum, into the periplasmic space or into the extracellular environment, appropriate secretion signals may be incorporated into the expressed polypeptide, for example, the amino acid sequence KDEL (SEQ ID NO: 151). The signals may be endogenous to the polypeptide or they may be heterologous signals.

The polypeptides may be expressed in a modified form, such as a fusion protein, and may include not only secretion signals, but also additional heterologous functional regions. For instance, a region of additional amino acids, particularly charged amino acids, may be added to the N-terminus or C-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. An example of such a fusion protein may comprise a heterologous region from immunoglobulin that is useful to solubilize proteins.

Therapeutic Compositions and Methods for Treating or Preventing Endometriosis

Peptides may be provided in pharmaceutical compositions and administered to a subject to treat or prevent the development of endometriosis in the subject.

Appropriate subjects may be mammals, such as humans, non-human primates, canines, felines, equines, porcines, ovines, bovines, sheep, mice and rat. Appropriate therapeutics can be administered to a subject in a "endometriosis inhibitory amount," i.e., an amount of the peptide that is therapeutically effective to inhibit or decrease the development or growth of endometriotic lesions. The therapeutics may be administered alone or, in combination with pharmaceutically acceptable carriers, excipients or diluents, in a pharmaceutical composition, according to standard pharmaceutical practice. Therapeutics may be administered directly into endometrial tissue, orally or parenterally, including intravenously, intramuscularly, intraperitoneally, subcutaneously, rectally and topically. Therapeutic peptides may be co-administered with zinc. For example a therapeutic composition may be administered in a therapeutically effective dose (see below) together with a therapeutically effective dose of $Zn^{2+}$ (see below). The peptide may be combined with the zinc solution prior to administration or at the time of administration to allow zinc to interact with the peptide. Alternatively, the peptide or variant or derivative thereof can be administered separately from the zinc, either before or after administration of the zinc, provided that both are present in the circulation at least during a common period. For example, a solution of zinc may be administered about a few minutes to a few hours before or after administration of the peptide. In yet other embodiments, no zinc is administered to a subject to whom a peptide is administered. Peptides that are administered may, however, still bind zinc when the subject has zinc in his blood circulation.

Toxicity and therapeutic efficacy of the therapeutics can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Reagents which exhibit large therapeutic indices are preferred. While reagents that exhibit toxic side effects may be used, care should be taken to design a delivery system that targets such reagents to the site of affected tissue in order to, e.g., minimize potential damage to normal cells and, thereby, reduce side effects.

The data obtained from cell culture assays and animal studies can be used in formulating a range of dosage for use in humans. The dosage of such therapeutics lies preferably within a range of circulating concentrations that include the $ED_{50}$ with little or no toxicity. The dosage may vary within this range depending upon the dosage form employed and the route of administration utilized. For any therapeutic used, the therapeutically effective dose can be estimated initially from cell culture assays. A dose may be formulated in animal models to achieve a circulating plasma concentration range that includes the $IC_{50}$ (i.e., the concentration of the test therapeutic which achieves a half-maximal inhibition of symptoms) as determined in cell culture. Such information can be used to more accurately determine useful doses in humans.

The dosage of the therapeutic will depend on the disease state or condition being treated and other clinical factors such as weight and condition of the human or animal and the route of administration of the compound. For treating humans or animals, between approximately 0.5 mg/kilogram to 500 mg/kilogram of the therapeutic can be administered. A more preferable range is about 1 mg/kilogram to about 100 mg/kilogram or from about 2 mg/kilogram to about 50 mg/kilogram with the most preferable range being from about 2 mg/kilogram to about 10 mg/kilogram. Depending upon the half-life of the therapeutic in the particular animal or human, the therapeutic can be administered between several times per day to once a week. It is to be understood that the methods have application for both human and veterinary use. The methods of the present invention contemplate single as well as multiple administrations, given either simultaneously or over an extended period of time.

Zinc may be co-administered with a therapeutic peptide in a concentration of about 0.1 to about 100 mg/kg/day; about 1 to about 10 mg/kg/day; or about 2-5 mg/kg/day. Zinc may be administered in the form of $Zn^{2+}$ or a salt thereof. The amount of zinc may vary depending on the amount of zinc in a subject's circulation (e.g., blood) and on the amount of peptide administered to the subject. The amount of zinc that may be necessary can be determined, e.g., by taking a blood sample of a subject having received a particular dose of peptide alone or with zinc and determining the amount of peptide to which zinc is complexed, e.g., as described above.

Pharmaceutical compositions containing a therapeutic may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain the active ingredient (i.e., therapeutic) in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions may contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

Pharmaceutical compositions may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solution. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's bloodstream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump. For example, one could generate blood levels of therapeutic peptides in the range of about 100 to 500 ng/ml, or about 200 to 400 ng/ml or about 250-300 ng/ml.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

In certain embodiments, it may be preferable to administer a therapeutic locally, such as by local injection.

In one embodiment, a therapeutic peptide is incorporated into a topical formulation containing, e.g., a topical carrier that is generally suited to topical drug administration and comprising any such material known in the art. The topical carrier may be selected so as to provide the composition in the desired form, e.g., as an ointment, lotion, cream, microemulsion, gel, oil, solution, or the like, and may be comprised of a material of either naturally occurring or synthetic origin. It is preferable that the selected carrier not adversely affect the active agent or other components of the topical formulation. Examples of suitable topical carriers for use herein include water, alcohols and other nontoxic organic solvents, glycerin, mineral oil, silicone, petroleum jelly, lanolin, fatty acids, vegetable oils, parabens, waxes, and the like. Formulations may be colorless, odorless ointments, lotions, creams, microemulsions and gels.

Various additives, known to those skilled in the art, may be included in formulations.

Other active agents may also be included in formulations, e.g., other anti-inflammatory agents, analgesics, antimicrobial agents, antifungal agents and other antibiotics.

Therapeutics may also be administered in the form of a suppository for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

Therapeutics may be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

The therapeutic peptides may be administered on a dose-schedule that maintains a constant concentration in the circulation. They may also be administered on a dose-schedule in which therapy is periodically discontinued, e.g., a once daily bolus injection.

If formulated as a fixed dose, such combination products employ the combinations described herein within the dosage range described herein and the other pharmaceutically active agent(s) within its approved dosage range. Combinations of the instant invention may also be used sequentially with known pharmaceutically acceptable agent(s) when a multiple combination formulation is inappropriate.

Exemplary Kits

Also provided herein are kits, e.g., therapeutic kits. A kit may comprise a therapeutic peptide described herein and optionally a device for administration of the the therapeutic peptide. A kit may also comprise a therapeutic peptide in a lyophilized form and a solution or buffer to solubilize the therapeutic peptide. A kit may also comprise instructions for use.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, $2^{nd}$ Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No: 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

Exemplification

The invention now being more generally described, it will now be more readily understood by reference to the following examples, which are included merely for purposes of illustration of certain aspects and embodiments of the present invention, and are not intended to limit the invention.

EXAMPLE 1

Identification of a 27 Amino Acid Endostatin Peptide that is Responsible for Anti-Tumor Activity Overlapping peptides with 24-27 amino acids derived from both mouse endostatin and human endostatin were synthesized (Table 1).

TABLE 1

Overlapping mouse and human endostatin peptides

| Name | Sequence |
| --- | --- |
| Mouse Peptides | |
| mP1: | HTHQDFQPVLHLVALNTPLSGGMRGIR; (SEQ ID NO:4) |
| mP2: | MRGIRGA DFQAFQQARA VGLSGTFR; (SEQ ID NO:136) |
| mP3: | TFRAFLSSRLQDLYSIVRRADRGSV; (SEQ ID NO:137) |
| mP4: | GSVPIVNLKDEVLSPSWDSLFSGSQ; (SEQ ID NO:138) |
| mP5: | GSQGQVQPGARIFSFDGRDVLRHPA; (SEQ ID NO:139) |
| mP6: | HPAWPQKSVWHGSDPSGRRLMESY; (SEQ ID NO:140) |
| mP7: | ETWRTETTGATGQASSLLSGRLLEQ; (SEQ ID NO:141) |
| mP8: | KAASAHNSYIVLAIENSFMTSFSKKK. (SEQ ID NO:142) |
| Human Peptides | |
| hP1 | 1 HSHRDFQPVLHLVALNSPLSGGMRG 25 (SEQ ID NO:6) |
| hP2 | 23 MRGIRGADFQ*A*FQQARAVGLAGTFR 47 (SEQ ID NO:143) |
| hP3 | 45 TFRAFLSSRLQDLYSIVRRADRAAV 69 (SEQ ID NO:144) |
| hP4 | 67 AAVPIVNLKDELLFPSWEALFSGSE 91 (SEQ ID NO:145) |
| hP5 | 89 GSEGPLKPGARIFSFDGKDVLRHPT 113 (SEQ ID NO:146) |
| hP6 | 111 HPTWPQKSVWHGSDPNGRRLTESY 134 (SEQ ID NO:147) |
| hP7 | 136 ETWRTEAPSATGQASSLLGGRLLGQ 160 (SEQ ID NO:148) |
| hP8 | 158 LGQSAAS*A*HHAYIVL*A*IENSFMTASK<u>KK</u> 183 (SEQ ID NO:149) |

Peptides were approximately ⅐th-⅛th the size of full length endostatin. Three cysteines, 33,165,173, were replaced by alanines (underlined in Table 1), and cysteine 135 was omitted, to prevent the formation of disulfide bonds. Two additional lysines were added at the C-terminal of hP8 to increase its solubility (double underlined). Most peptides were water soluble, except for hP2 at high concentrations (>2.5 mg/ml). Also, all peptides were approximately 70% pure. However, no difference in tumor inhibition was observed when peptides of more than 95% purity were used.

These peptides were initially tested for anti-tumor activity employing the human pancreatic tumor cells BxPC-3 cells, which were implanted in the s.c. dorsa of SCID mice. For systemic treatment, human endostatin peptides, P1-P8, were administered subcutaneously (s.c.) twice a day at 7 mg/kg/d due to the high clearance rate from the mouse circulation. Full-length Fc-Endostatin, hFcES was administered subcutaneously only once per day at a dose of 20 mg/kg/d. PBS was used as a control. Tumors were measured every three days and the final measurements at 28 days are shown in FIG. 1 (T/C is indicated in each bar and the group sizes had an n equal to 3.

The N-terminal hP1 peptide of endostatin inhibited BxPC-3 by 39% (p=0.077) and full-length endostatin by 44% (p=0.0057) (FIG. 1). Two other peptides, hP2 and hP5, also showed some small anti-tumor activity, where hP2 inhibited BxPC-3 by 19% (p=0.48) and hP5 by 29% (p=0.15). Other peptides had no effect (FIG. 1). Thus, most of the anti-tumor activity was associated with the N-terminal hP1 peptide compared to full-length endostatin. Although tumor inhibition by hP1, hP2 and hP5 was not statistically significant due to the small number of mice per group (n=3), the trends suggesting tumor inhibition by these peptides prompted further study of such peptides on tumor inhibition in the murine LLC model. Moreover, peptides and full-length endostatin were not at equimolar concentrations. However, this data suggests that the anti-tumor property of endostatin may be located within its N-terminal domain.

The N-terminal 27 Amino Acid Peptide of Endostatin is Responsible for its Anti-Tumor Property The murine LLC tumor model (O'Reilly et al. (1994) Cell, 79: 315-328) was used to further characterize these peptides because this tumor grows more rapidly than BxPC-3 cells, allowing for shorter treatment periods. Murine analogs of the endostatin peptides were synthesized. The only difference between the human and murine peptides was that murine P1 peptide contained 27 amino acids instead of 25 amino acids for human P1. We tested only those peptides that showed any anti-tumor activity in the previous experiment (see FIG. 1).

Figure 2:
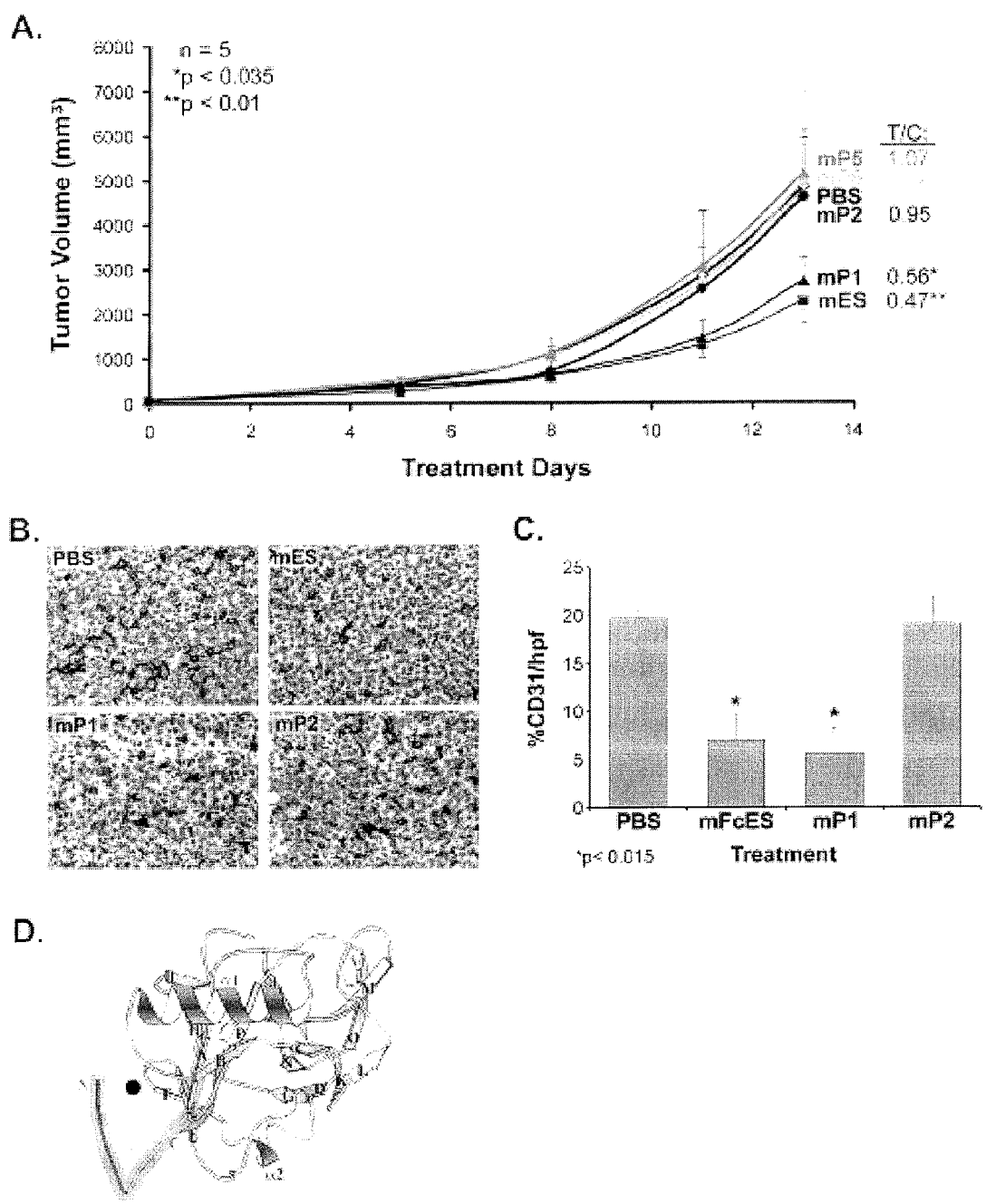
FIG. 2A-C are graphs showing that the N-terminal domain of endostatin is responsible for its anti-tumor properties.
FIG. 2D is a schematic diagram showing the crystal structure of endostatin.

Unlike the BxPC-3 treatment, LLC tumors were treated at equimolar concentrations of murine endostatin and murine peptides (mP1, mP2, mP5, and mP6). mP6 was used as a representative control peptide, because it showed no anti-tumor activity (see FIG. 1). Control mice were treated with PBS. In these experiments, LLC cells were implanted into the s.c. dorsa of C57B1/6J mice, and systemically treated. Peptides (mP1, mP2, mP5, and mP6) were injected (s.c.) twice a day at a dose of 2.8 mg/kg/d, whereas endostatin and PBS were administered once a day at a dose of 20 mg/kg/d. The N-terminal mP1 endostatin peptide inhibited LLC by 44% (p<0.035), which is comparable to the inhibition by full-length endostatin (53%, p<0.01) (FIG. 2A; T/C is indicated in the figure). No or insignificant activity was detected employing mP2, mP5 and mP6 at the same concentration as the mP1 peptide (FIG. 2A). Thus, this result suggests that the 27 amino acids mP1 peptide contains all of the anti-tumor activity associated with endostatin.

To determine the effect on angiogenesis after mP1 treatment, LLC tumors treated with mP1, mP2, and endostatin at equimolar concentration were analyzed for vessel density (CD31). FIG. 2B shows CD31 staining of LLC sections from mice treated with PBS (control), Fc-Endostatin (20 mg/kg/d), mP1 (2.8 mg/kg/d), and mP2 (2.8 mg/kg/d). In each case, peptides were administered twice a day s.c. and LLC tumor sections from day 13 were formalin-fixed paraffin-embedded and then stained with CD31 (PECAM). FIG. 2C show the determination of vessel density and the Y axis is expressed as %CD31/high power field (hpf). Treatment of LLC with mP1 and endostatin reduced vessel density significantly (approximately 65%, p<0.015), while mP2 and PBS had no effect. Treatment with mP5 and mP6 showed similar results as mP2 treatment. These results suggest that mP1 can inhibit LLC tumor growth by reducing vessel density in similar manner to full length endostatin.

Histidines at Position 1 and 3 of Endostatin are Critical for Zinc Binding

The crystal structure of endostatin reveals a highly folded molecule (FIG. 2D). However, the N-terminal region resembles a random coil structure consistent with our analysis that a synthetic peptide corresponding to this domain can mimic the native molecule (FIG. 2D). Because the endostatin N-terminal domain is responsible for its anti-tumor activity, we wanted to investigate the mP1 peptide further. There is an atom of Zinc (Zn) associated with each molecule of endostatin (Ding et al. (1998) Proc Natl Acad Sci USA, 95: 10443-10448). Based on our crystal structure analysis, three histidines at positions 1, 3, and 11 plus, aspartic at position 76, form the four coordinates for this Zn atom (Ding et al. (1998) Proc Natl Acad Sci USA, 95: 10443-10448). mP1 contains the three histidines mentioned above. This raises the possibility that this peptide is capable of binding Zn, by having a molecule of water occupying the fourth coordinate (FIG. 3A, left panel). It has been shown previously that mutations of histidines 1 and 3 disrupt Zn binding of endostatin (Boehm et al. (1998) Biochem Biophys Res Commun, 252: 190-194). Therefore, a mutant of peptide mP1 was synthesized where the histidines at position 1 and 3 were mutated to alanines. This mutant peptide was called mP1-H1/3A (also referred to mP1-H) and has the following amino acid sequence: ATAQD-FQPVLHLVALNTPLSGGMRGIR (SEQ ID NO: 150). The sequences of mP1 and mP1-H1/3A are also indicated in FIG. 3A.

To determine the Zn binding capacity of mP1 and mP1-H1/3A flame atomic absorption was performed. Each peptide was dissolved in 20 mM Tris, pH 8.0 at a concentration of 0.5 mg/ml, mixed with excess Zn chloride (1 mM), and extensively dialyzed against the above buffer for 72 hours with three changes in dialysis solution (molecular weight cut off (MWCO)=1000 kDa; the molecular weight of the peptides was taken to be 3000 kDa). Atomic absorption readings of the final zinc concentrations (μg/ml) were determined to be 9.63 and 1.05 for mP1 and mP1-H1/3A, respectively. These data yielded zinc ratios of 0.1 per molecule of mP1-H1/3A and 0.9 for mP1 (FIG. 3B). Therefore, mutating the histidines at position 1 and 3 to alanines abolished Zn binding (FIG. 3A, right panel).

The Zinc Binding Domain of Endostatin is Important for its Anti-Tumor Activity

To determine if Zn binding is also important for the anti-tumor property of endostatin, mP1 and mP1-H1/3A were tested using the LLC tumor model. Peptides were administered twice a day (s.c.) at a dose of 2.8 mg/kg/d. Peptide mP1 inhibited LLC by 42% (p=0.031), whereas mP1-H1/3A had no effect (FIG. 3C). To determine if there was a difference in angiogenesis, vessel density (CD31) of LLC tumors was analyzed after mP1 and mP1-H1/3A treatment. There was a considerable decrease in vessel density after mP1 treatment (67% reduction, p<0.01), whereas mP1-H1/3A was similar to PBS (FIG. 3D and 3E). These data suggest that Zn binding is important for the anti-tumor property of endostatin. The unpaired Student t test was used for statistical analysis.

Figure 3:
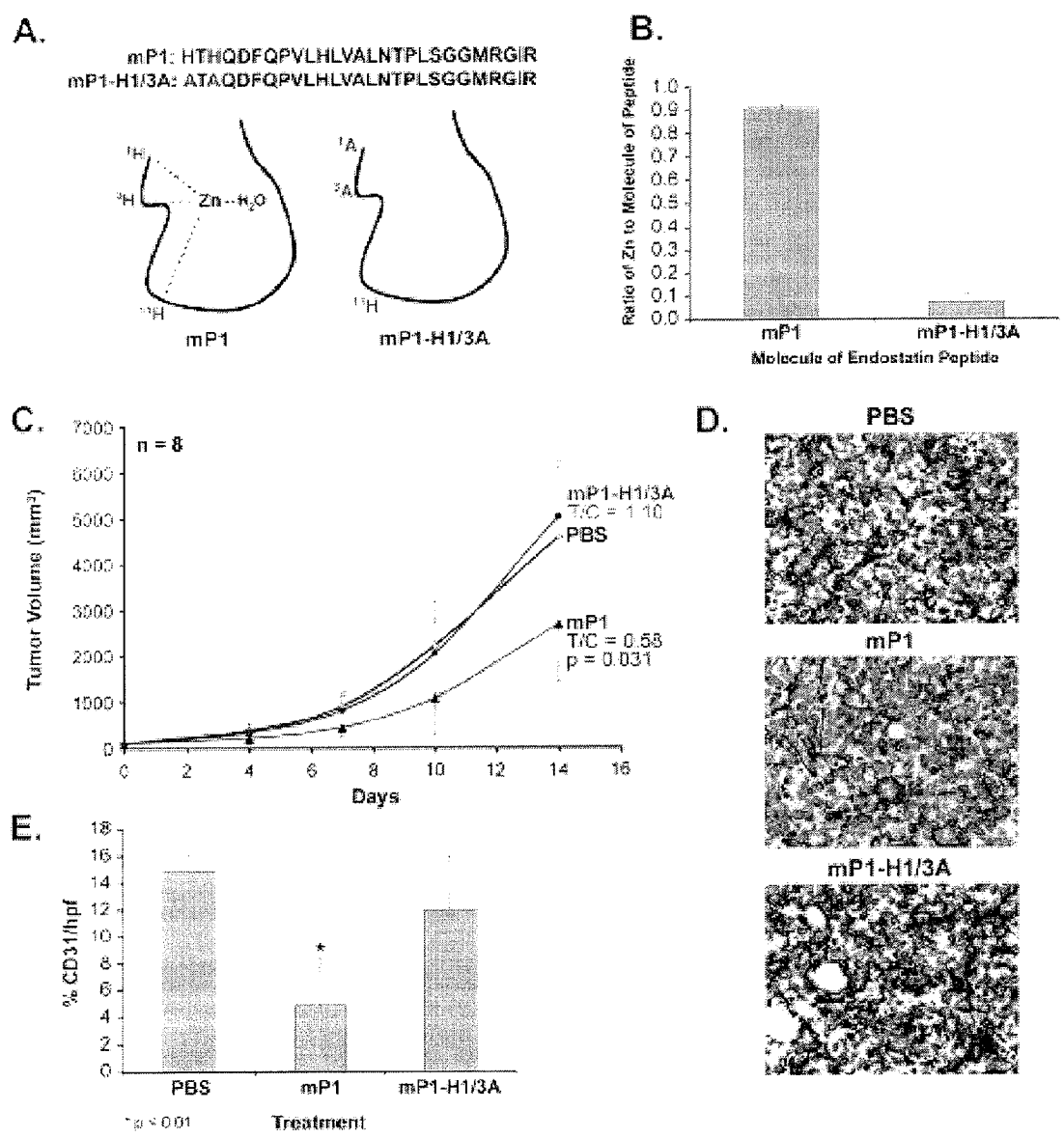
FIG. 3A-E are graphs showing that the zinc binding site of endostatin is important for anti-tumor activity.
Figure 4:
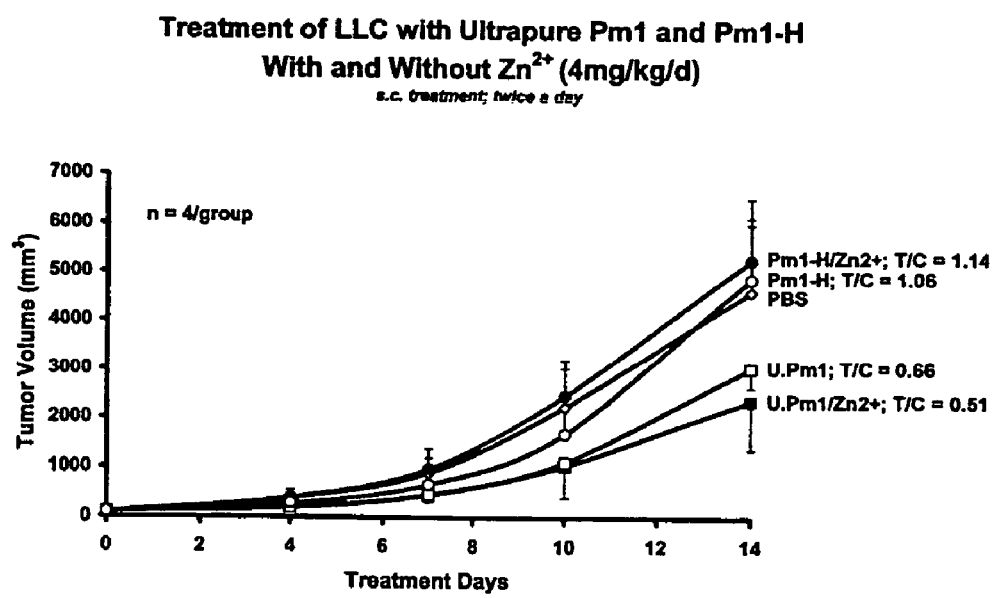
FIG. 4 is a graph showing the tumor volume of mice having LLC treated twice daily with mP1 or mP1-H with or without zinc on days 4, 7, 10 and 14.

Additional treatments included subcutaneously injection the mP1-H peptide together with 1 mM of $Zn^{2+}$; subcutaneously injecting the mP1 peptide alone or with 1 mM of $Zn^{2+}$; or subcutaneously injecting PBS (FIG. 4). The results, which are shown in FIGS. 3 and 4, indicated that tumor volume was essentially not affected by the administration of the mP1-H1/3A peptide, in which histidines 1 and 3 are changed to alanines, since the tumor mass was similar to that obtained when injecting PBS (the negative control).

Thus, these results indicate that the histidines at positions 1 and 3 in N-terminal endostatin peptides cannot be replaced by alanines and that their substitution with another amino acid would likely also reduce or eliminate the anti-tumor effect of the peptides. The results further indicate that it may be beneficial to include zinc in the composition comprising the peptide, unless there zinc is already present in the circulation.

Figure 5:
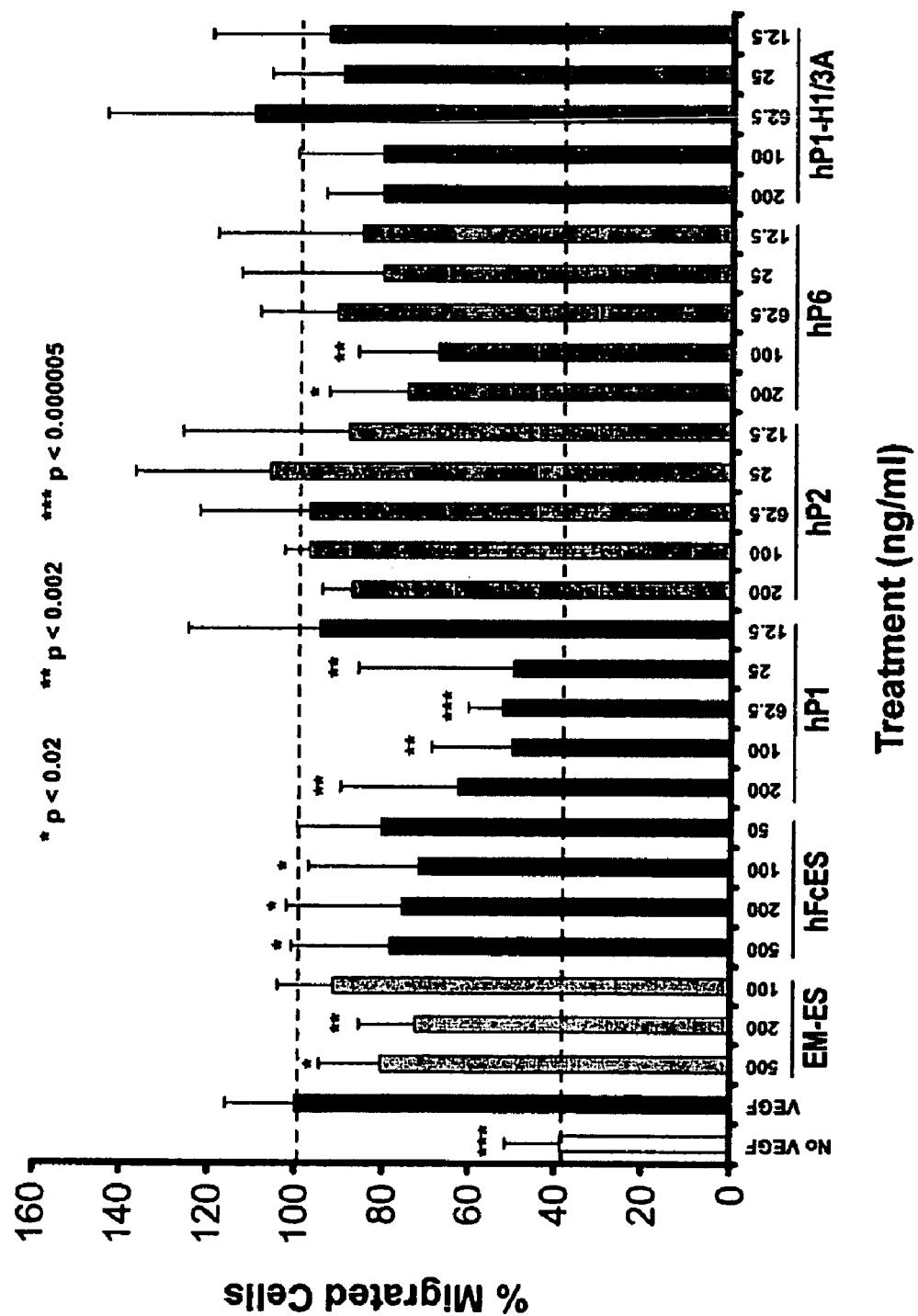
FIG. 5 is a graph showing inhibition of endothelial cell migration by endostatin peptides.

The N-Terminal Fragment of Endostatin Retains its Capacity to Inhibit Endothelial Cell Migration Endostatin peptides were tested for anti-endothelial cell migration activity. Inhibition of VEGF-induced migration of human microvascular endothelial cells (HMVECs) was determined using several doses of endostatin peptides (FIG. 5). Human peptides were used because the cells were of human origin and the migration response of the HMVECs was assayed using a modified Boyden chamber. VEGF (5 ng/ml) was used a chemotactic agent and cells were challenged with human endostatin (Entremed; EM-ES), human Fc-Endostatin (nFcES), human P1 (hP1), human P2 (hP2), human P6 (hP6), and human P1-H1/3A (hP1-H1/3A). Total migration per membrane was quantified from the capture images using Scion Image Software (National Institutes of Health) and the unpaired Student T test was used for statistical analysis. Human recombinant endostatin (Entremed) inhibited EC migration at 500 and 200 ng/ml (30%) but not at 100 ng/ml, whereas human Fc-Endostatin inhibited equally well between 500 and 100 ng/ml (25-30%) (FIG. 5). Interestingly, slightly better inhibition of EC migration was observed at 100 ng/ml for Fc-Endostatin and 200 ng/ml for endostatin (EntreMed) than higher concentrations, which suggested a U-shaped endostatin response. The best inhibition for hP1 was at 100, 62.5, and 25 ng/ml. No significant differences in inhibition between these concentrations were observed. At higher and lower concentrations less or no inhibition was observed. At 500 ng/ml of hP1 no inhibition was observed. Thus, similar to full-length endostatin, there is a U-shaped response to hP1 inhibition of EC migration. Endostatin hP2 peptide had no effect at all even at higher concentrations. However, hP6 inhibited EC migration but at higher concentrations than hP1 and no inhibition was observed for concentrations lower than 100 ng/ml.

To determine if the Zn binding site is important for anti-endothelial cell migration activity, hP1-H1/3A was also tested. This mutant peptide did show some small inhibition at 200 and 100 ng/ml. However, this inhibition was statistically not significant. Thus, peptide hP1 could inhibit VEGF-induced EC migration at equimolar concentrations (25 ng/ml) to full-length endostatin or human endostatin (EntreMed) (200 ng/ml), whereas hP6 only inhibited at doses of 100 and 200 ng/ml. Interestingly, hP1 was more potent in inhibiting EC migration than full-length endostatin. These results show that the N-terminal P1 peptide of endostatin maintains the ability to inhibit VEGF-induced EC migration and that the Zn binding site is critical for this activity.

Anti-Permeability Activities of Endostatin Peptides

Figure 6:
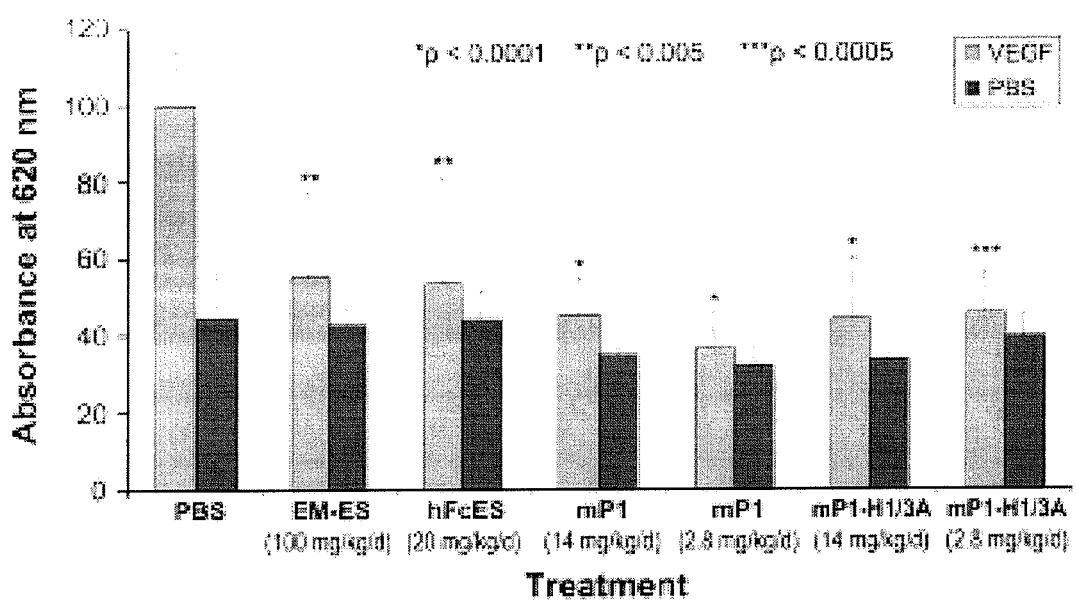
FIGS. 6A and B show inhibition of VEGF-induced permeability by endostatin peptides.
FIG. 6B shows representative pictures of a Miles assay (V is VEGF, P is PBS).
Figure 6:
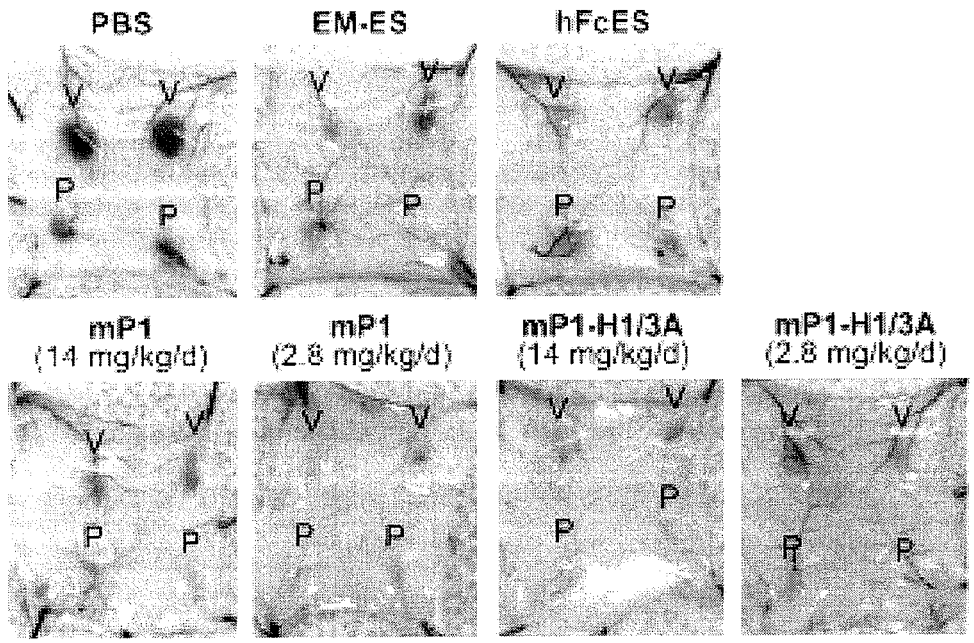

The ability of endostatin peptides to inhibit VEGF-induced permeability was also tested using the Miles assay (Miles and Miles (1952) J Physiol, 118: 228-257). Previously, endostatin has been shown to inhibit VEGF-induced permeability using the Miles assay. Immunocompromised SCID mice were treated 5 days before performing the Miles assay. Specifically, SCID mice were injected subcutaneously (s.c.; twice a day) with human endostatin (EntreMed; EM-ES) at a dose of 100 mg/kg/d; murine Fc-Endostatin at a dose of 20 mg/kg/d; murine endostatin peptides, mP1 and mP1-H1/3A, at a dose of 2.8 mg/kg/d or 14 mg/kg/d; or with PBS (n=3) for 5 days. At the high dose (14 mg/kg/d), both mP1 and mP1-H1/3A inhibited VEGF-induced permeability as well as human endostatin (EntreMed) and murine Fc-Endostatin (FIG. 6). However, similar results were obtained when equimolar concentrations (2.8 mg/kg/d) were used (FIG. 6). Because mP1-H1/3A showed the same inhibition as mP1, even at equimolar concentration, this suggests that there is a separation of activity between anti-tumor and antipermeability.

Figure 7:
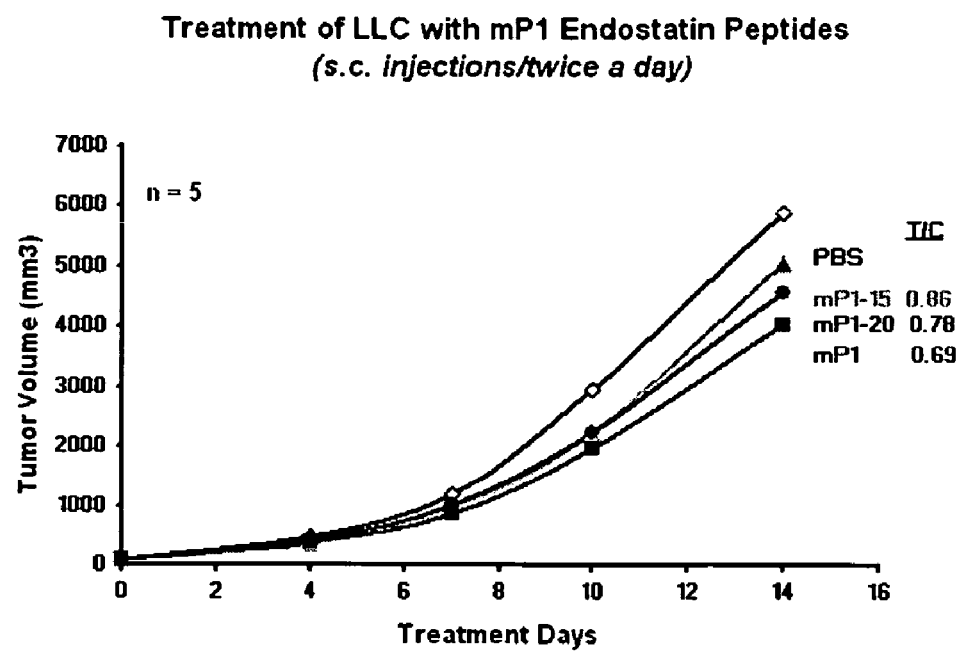
FIG. 7 is a graph showing the tumor volume in mice to which mP1 endostatin peptides mP1, mP1-15, mP1-20 or PBS was administered as a function of days following the beginning of the treatment.

Smaller peptides derived from mP1 were also shown to inhibit tumor growth. Two peptides, mP1-15 (SEQ ID NO: 118) and mP1-20 (SEQ ID NO: 108), were tested for anti-tumor activity using the LLC tumor model. Peptides were administered s.c. twice a day at dose of 2.8 mg/kg/day on days 4, 7, 10 and 14. PBS was used as a control. FIG. 7 shows that both mP1-15 and mp1-20 inhibit tumor volume. (T/C is indicated and the group size has an n equal to 5).

Thus, we have shown that a synthetic peptide, corresponding to the N-terminus of endostatin, is responsible for its anti-tumor, anti-migration, and anti-permeability activities. Zinc binding is required for the anti-tumor and anti-migration activities, because substitution of the two histidines at amino acid positions 1 and 3 in the peptide completely blocks its properties. However, Zn binding was not required for anti-permeability property.

The zinc binding requirement of endostatin for inhibiting tumor formation has been controversial, with conflicting results reported from different groups (Boehm et al. (1998) Biochem Biophys Res Commun, 252: 190-194; Yamaguchi et al. (1999) Embo J, 18: 4414-4423; Sim et al. (1999) Angiogenesis, 3: 41-51). Whereas, the earliest report showed that the replacement of histidines 1 and 3 by alanines blocked the inhibitory effect of endostatin in LLC (Boehm et al. (1998) Biochem Biophys Res Commun, 252: 190-194), two later publications challenged this finding (Yamaguchi et al. (1999) Embo J, 18: 4414-4423; Sim et al. (1999) Angiogenesis, 3: 41-51). In one of these reports, a mutant endostatin was prepared by deleting 5 amino acids in both C- and N-termini (Yamaguchi et al. (1999) Embo J, 18: 4414-4423). This construct elicited anti-tumor activity, similar to full-length endostatin. However, in the employed renal Rc-9 carcinoma tumor model, the administration of endostatin was initiated when the tumor size was 300 mm$^3$, and lasted for only 4 days, when the tumor size reached 500 mm$^3$. The injection sites were at the periphery of the tumor, and the injection dosage was 10 µg/kg/d. In contrast, in our experiments we initiated treatment when LLC tumors reached a size of ~100 mm$^3$ and continued until tumors were ~6000-7000 mm$^3$. Furthermore, we treated systemically and did not inject into the periphery of the tumor.

Another publication which dealt with the relevance of zinc binding to anti-tumor activity of endostatin, demonstrated that the removal of 4 amino acids "HSHR" from N-terminus of human endostatin did not affect its anti-tumor activity (Sim et al. (1999) Angiogenesis, 3:41-51). Measurements of zinc binding revealed that this mutant bound 2 atoms of zinc per molecule of endostatin, whereas the wild type bound 10 atoms of zinc per endostatin molecule. However, in our crystal structure studies of endostatin, we have demonstrated that the endostatin employed for crystallization studies, contains 1 atom of zinc/endostatin molecule and the removal of the 4 amino acids "HSHR" from N-terminus lacks zinc binding (Ding et al. (1998) Proc Natl Acad Sci USA, 95: 10443-10448).

Endostatin is generated by proteolytic cleavage of collagen 18 (O'Reilly et al. (1997) Cell, 88: 277-285; Wen et al. (1999) Cancer Res, 59: 6052-6056; Felbor et al. (2000) Embo J, 19: 1187-1194). The first amino acid at the N-terminus of endostatin is a histidine. The presence of histidine is important for conferring Zn binding to endostatin. Consequently, we are led to conclude that the processing of collagen 18 to endostatin may be highly regulated.

Several groups have shown that peptides derived from endostatin have antiangiogenic effects (Wickstrom et al. (2004) J Biol Chem, 279: 20178-20185; Cattaneo et al. (2003) Exp Cell Res, 283: 230-236; Chillemi et al. (2003) J Med Chem, 46: 4165-4172; Morbidelli et al. (2003) Clin Cancer Res, 9: 5358-5369; Cho et al. (2004) Oncol Rep, 11: 191-195). An N-terminal peptide comprising amino acids 6-49 (lacking the zinc binding histidines) has inhibited endothelial cell proliferation and migration (Cattaneo et al. (2003) Exp Cell Res, 283: 230-236; Chillemi et al. (2003) J Med Chem, 46: 4165-4172). A Matrigel assay, employing this peptide has resulted in the inhibition of angiogenesis in vivo. However, no antitumor data was presented. In another study, a C-terminal peptide (amino acids 135-184) retaining the Cys135-Cys165 disulfide bond, has demonstrated anti-tumor activity (Morbidelli et al. (2003) Clin Cancer Res, 9: 5358-5369). However, the peptide was administered at the tumor periphery and not systemically. Cho et al. have shown that N-terminus, which includes the Zn binding site, and the C-terminus of endostatin are not required for anti-tumor activity (Cho et al. (2004) Oncol Rep, 11: 191-195). However, this peptide and full-length endostatin were not tested at equimolar concentrations. Our results differ from these groups in that the P1 peptide could inhibit tumor formation, migration, and permeability at equimolar concentrations to full length endostatin. Furthermore, at higher concentrations (14 mg/kg/d) mP2 could inhibit LLC tumor formation as well as mP1 at 2.8 mg/kg/d. However, mP1 at 14 mg/kg/d inhibited LLC tumor formation less than at 2.8 mg/kg/d. Thus, a U-shaped curve seems to be associated with anti-tumor activity of endostatin as a function of the protein concentration. Similar results were observed for full-length endostatin using the pancreatic BxPC-3 and ASPC-1 tumor models. Therefore, determination of optimum endostatin concentration may be an important factor. In vitro assays have demonstrated a similar biphasic characteristic by endostatin such as seen in migration assays (see FIG. 5).

The fact that full-length endostatin is not required for its anti-tumor activity explains the initial inconsistencies of endostatin activity. Endostatin has two disulfide bonds. Aggregation of endostatin in *E. coli* preparations is caused by random inter-molecular disulfides after PBS dialysis. Whereas, endostatin demonstrates a single protein molecule under reducing conditions, most of the protein in an identical sample does not enter the polyacrylamide gel under nonreducing condition. It is probably the degree of nonspecific aggregation that is responsible for the lack of activity in some of the preparations. Endostatin is most likely released from the aggregate in animals over a period of time, resulting in a denatured protein or partial fragments, which are capable of demonstrating anti-tumor properties due to their N-terminal peptide. Presumably, some of the preparations yield larger aggregates, which make such a release inefficient and give rise to a product that is incapable of eliciting antiangiogenic response in mice.

What is the basis of endostatin's anti-tumor activity? A large number of mechanisms have been proposed. One which has been studied in more detail is the endostatin binding to integrin $\alpha5\beta1$ (Wickstrom et al. (2002) Cancer Res, 62: 5580-5589). Based on the findings of these authors, an assembly of several cell surface proteins and components including $\alpha5\beta1$, are responsible for interactions between endostatin and this integrin (Wickstrom et al. (2003) J Biol Chem, 278: 37895-37901). However, no anti-tumor data were presented to confirm the above mechanism. More recently, the same authors have shown that an 11 amino acid peptide derived from endostatin containing arginines and showing heparin binding, is responsible for antiangiogenic activity of endostatin (Wickstrom et al. (2004) J Biol Chem, 279: 20178-20185). We speculate that the phenomena observed by these investigators, reflects some of the properties associated with heparin binding characteristic of endostatin, and not its anti-tumor activity. Previously, we reported that disruption of heparin binding of endostatin (accomplished by the mutation of two discontinuous arginines on the protein surface) blocked cell motility (Kuo et al. (2001) J Cell Biol, 152: 1233-1246). Furthermore, our endostatin hP3 peptide (see Table 1), which contains the peptide reported by the authors, failed to inhibit tumor growth.

Materials and Methods:

Cell Culture and Reagents

Human BxPC-3 pancreatic adenocarcinoma and Lewis lung carcinoma (LLC) cells were grown and maintained as described earlier (Kisker et al. (2001) Cancer Res, 61:7669-7674; O'Reilly et al. (1994) Cell, 79: 315-328). For BxPC-3 tumor cell injection, cells were grown in 900-cm2 roller bottles. Human microvascular endothelial cells (HMVEC-d; Clonetics, Walkersville, Md.) were cultured in microvascular endothelial cell growth medium (EGM-2 MV; Clonetics) and maintained at 5% CO2 in a 37° C. humidified incubator. Recombinant human endostatin was a generous gift from EntreMed Corporation (Rockville, Md.) and recombinant human and murine FcEndostatin were prepared as described earlier (Bergers et al. (1999) Science, 284: 808-812). Human and murine endostatin peptides were synthesized by SynPep Corporation (Dublin, Calif.). Peptides were resuspended in PBS or 50 mM Tris, 150 mM NaCl, pH 7.5. PECAM, purified rat anti-mouse CD31, was obtained from BD Pharmingen (San Diego, Calif.) and human recombinant VEGF was obtained from the NIH (Bethesda, Md.).

Animal Studies

All animal procedures were performed in compliance with Boston Children's Hospital guidelines, and protocols were approved by the Institutional Animal Care and Use Committee. Male (24-27 g) immunocompetent C57B1/6J mice (Jackson Laboratories, Bar Harbor, Me.) and immunocompromised SCID mice (Massachusetts General Hospital, Boston, Mass.) were used. Mice were 7-9 weeks of age. They were acclimated, caged in groups of five in a barrier care facility, and fed with animal chow and water ad libitum. Animals were anesthetized via inhalation of isoflurane (Baxter, Deerfield, Ill.) before all surgical procedures and observed until fully recovered. Animals were euthanized by a lethal dose of CO2 asphyxiation.

Tumor Models

BxPC-3 and LLC cells were grown in cell culture as described above. The cell concentration was adjusted to $50\times10^6$ cells/ml. Mice were shaved and the dorsal skin was cleaned with ethanol before tumor cell injection. A suspension of $5\times10^6$ tumor cells in 0.1 ml RPMI-1640 (for BxPC-3) or DMEM (for LLC) was injected subcutaneously (s.c.) into the dorsa of mice at the proximal midline. BxPC-3 cells were implanted in SCID mice and LLC in C57B1/6J mice.

Animals with Lewis Lung carcinoma (600-800 $mm^3$ tumors) were euthanized, and the skin overlying the tumor was cleaned with Betadine and ethanol. Tumor tissue was excised under aseptic conditions. A suspension of tumor cells in 0.9% normal saline was made by passage of viable tumor tissue through a sieve and a series of sequentially smaller hypodermic needles of diameter 22- to 30-gauge. The final concentration was adjusted to $1\times10^7$ cells/ml, and the suspension was placed on ice. The injection of tumor cells was performed as described above.

The mice were weighed and tumors were measured every 3-5 days in two diameters with a dial-caliper. Volumes were determined using the formula $a2\times b\times0.52$ (where a is the shortest and b is the longest diameter). Data is represented as volume of treated tumor over control (T/C). At the completion of each experiment, the mice were euthanized with CO2 asphyxiation. Tumors were fixed in 10% buffered Formalin (Fisher Scientific, Fair Lawn, N.J.) and paraffin-embedded.

For treatment of tumor-bearing mice, tumor volumes were allowed to grow to approximately 100 $mm^3$, and mice were randomized. Treatment was performed by single bolus s.c. injections. Peptides were administered twice a day (every 12 hrs). Doses indicated for peptides were corrected for the purity of peptides (approximately 70%). For example, mice injected with 4 mg/kg/d peptide, were actually injected with 2.8 mg/kg/d after correction. The unpaired Student t-test was used for statistical analysis.

Immunohistochemistry

Tumors were fixed in 10% buffered Formalin overnight at 4° C. The next day, tumors were washed three times in PBS and paraffin-embedded. Sections (5 µm) were permeabilized with 40 µg/ml proteinase K (Roche Diagnostics Corp.) in 0.2 M Tris-HCl buffer (pH 7.6) for 25 minutes at 37° C. and washed with PBS. PECAM (1:250) was incubated at 4° C. overnight. Stainings were amplified using tyramide signal amplification direct and indirect kits (NEN Life Science Products Inc., Boston, Mass.). Sections were photographed at 400× magnification using a NIKON TE300 microscope. Vessel density (average of three fields) was determined by IPLab software. The unpaired Student t-test was used for statistical analysis.

Cell Migration Assay

The motility response of HMVEC-d cells was assayed using a modified Boyden chamber. Cells were plated in T75-cm2 flasks at $0.5\times10^6$ cells per flask and allowed to grow for 48 h (~70% confluent) prior to the migration assay. To facilitate cell adhesion, the upper membrane of a transwell (8 mm pore; Costar) was coated with fibronectin (10 mg/ml; Becton Dickinson, Bedford, Mass.) for 1 h at 37° C. Coated membranes were rinsed with PBS and allowed to air dry immediately before use. Cells were detached by trypsinization, treated with trypsinization neutralization solution (Clonetics), and resuspended at a final concentration of $1\times10^6$ cells/ml in serum-free endothelial basal medium (EBM; Clonetics) containing 0.1% BSA. Cells (200,000 in 0.2 ml) were then treated with 0.2 ml of EBM/BSA containing endostatin or peptides at the indicated concentrations. Cells were incubated for 20 min. at 37° C. with occasional shaking. Cells (50,000 in 100 µl) were added to the upper chamber of the transwell. EBM or EBM supplemented with VEGF (5 ng/ml) was added to the lower chamber and cells were allowed to migrate toward the bottom chamber for 4 h in a humidified incubator containing 5% CO2. Transwell filters were rinsed once with PBS and fixed and stained using a Diff-Quik staining kit (Baxter) following the manufacturer's protocol. Non-migrated cells were removed from the upper chamber with a cotton swab. Stained filters were cut out of the chamber and mounted onto slides using Permount (Fisher). The number of migrated cells was measured using microscopy (three fields from each membrane were captured using a 40× objective), and images were captured with a CCD camera using SPOT software. Total migration per membrane was quantified from the captured images using Scion Image software (National Institutes of Health). All experiments were run in triplicate. The unpaired Student t-test was used for statistical analysis.

Miles Vascular Permeability Assay (The Miles Assay)

SCID mice were injected subcutaneously (s.c.) with human endostatin (EntreMed; 100 mg/kg/day), murine Fc-Endostatin (20 mg/kg/d), peptides (either 14 mg/kg/d or 2.8 mg/kg/d), and with saline (200 µl) (n=12) for 5 days prior to performing the Miles assay (25). Briefly, Evan's blue dye (100 µl of a 1% solution in PBS) was injected intravenously (i.v.) into mice. After 10 minutes, 50 µl of human recombinant VEGF (1 ng/µl) or PBS were injected intradermally into the pre-shaved back skin. After 20 minutes, the animals were euthanized and an area of skin that included the blue spot resulting from leakage of the dye was removed. Evan's blue dye was extracted from the skin by incubation with formamide for 5 days at room temperature, and the absorbance of extracted dye was measured at 620 nm using a spectrophotometer. The unpaired Student t-test was used for statistical analysis.

Statistical Methods

Data are expressed as mean +S.D. Statistical significance was assessed using the Student t-test. P<0.05 was considered statistically significant.

EXAMPLE 2

Endostatin Peptides Prevents the Growth of Endometriotic Lesions

Endostatin Peptides Have No Effect on Estrus Cycling

Endometriosis-like lesions were induced using a technique modified from Cummings and Metcalf (Reprod Toxicol. (1995) 9:233) as previously described (Efstathiou et al. in Fertil Steril, in press). Briefly, 8 week-old female C57B1/6J mice (Jackson Labs, Bar Harbor, Me.) were caged in groups of five and acclimated for a week. The animals were fed with animal chow and received water ad libitum. They were anesthetized via inhalation of isoflurane (Baxter, Deerfield, Ill.) during all surgical procedures and observed until fully recovered. During the initial procedure mice additionally received 0.01 mg/kg buprenorphine in phosphate buffered saline (PBS) and 0.9% saline by subcutaneous (s.c.) injection for analgesia and rehydration, respectively. Mice underwent laparotomy by midventral incision. Both uterine horns were ligated with small surgical titanium clips (Horizon, Research Triangle Park, N.C.), removed and placed in a Petri dish containing warmed Dulbecco's Modified Eagle Medium F-12 (Gibco, Grand Island, N.Y.) supplemented with 100 U/ml penicillin and 100 µg/ml streptomycin (Gibco, Grand Island, N.Y.). The uterine horns were opened longitudinally and seven biopsies (2 mm in diameter) were taken using a dermal biopsy punch (Miltex, Bethpage, N.Y.), which were sutured to the peritoneal wall and to the mesentery (four and three each, respectively) with a 7-0 braided silk suture (Ethicon, Somerville, N.J.). The abdominal wall was closed with a 5-0 braided silk suture in a continuous fashion.

Figure 8:
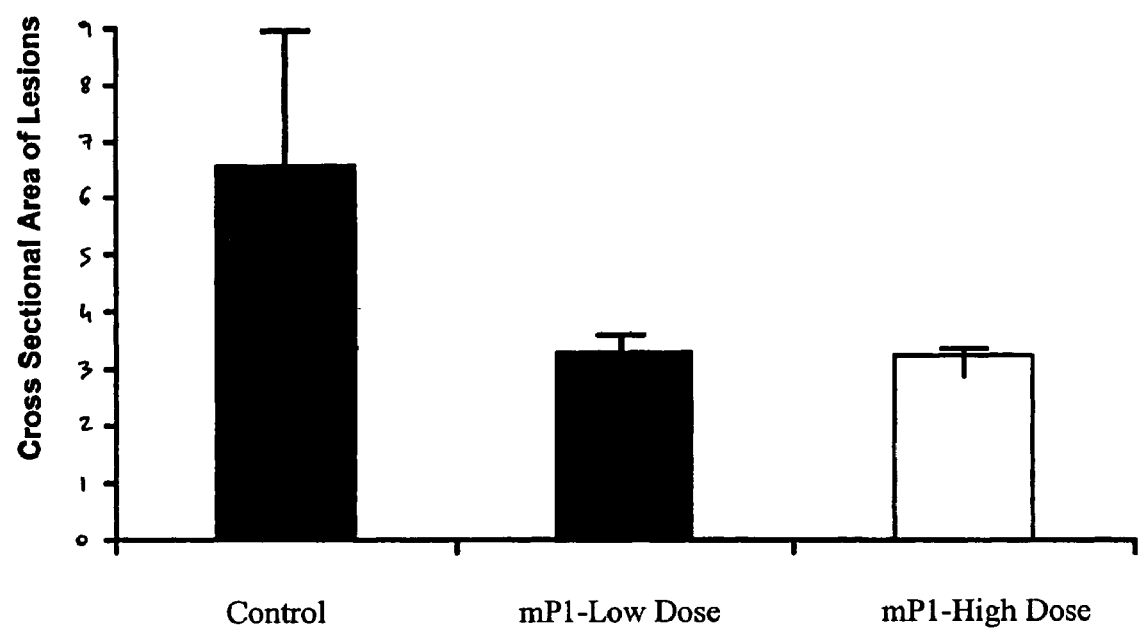
FIG. 8 is a graph showing the size of the endometriotic lesions in the groups of control mice, mice treated with a low dose of mP-1 (SEQ ID NO: 4) and mice treated with a high dose of mP-1.

In an initial experiment, six female C57BL/6 mice that had undergone endometriosis surgery received twice-daily s.c. injections (200 µl) of the murine N-terminal fragment of endostatin (mP-1). The peptide was dissolved in PBS, supplemented with 1 mM Zinc Chloride ($ZnCl_2$); in these experiments zinc was provided in a sufficient amount such that zinc was bound to each molecule. Three mice received mP-1 at a lower dose (2.5 mg/kg) and the other three mice received mP-1 at a higher dose (10 mg/kg) (FIG. 8). Control animals were injected with PBS plus 1 mM $ZnCl_2$. Treatment was initiated on postoperative day one and continued for four weeks when the experiment was terminated.

In a larger follow-up experiment, mice in the treatment group received the peptide at a dose of 2.5 mg/kg for four weeks. Peptide solutions (and PBS for the control group) were either supplemented with zinc (FIG. 9) or not supplemented with zinc (FIG. 10) as described above for the initial experiment (n=10/group). In addition to the group receiving mP-1, two additional groups were added (n=10/group). One group received mP-6, an endostatin peptide closer to the carboxy-terminal, and the other group received a mutant form of mP-1 in which the histines at amino acids 1 and 3 were changed to alanines (mP1-H1/3A).

After four weeks of treatment, the mice were sacrificed and the original ventral midline incision was re-opened. Lesions were identified at their implantation sites either by gross appearance or by the location of the suture. They were counted and two perpendicular diameters ($D_1$, $D_2$) of each lesion were measured with a calliper to the nearest tenth of a millimeter. Lesion volumes were determined using the formula volume=$D_1 \times D_2 \times \pi/4$ for a sphere. Then, lesions were excised and preserved in 10% phosphate-buffered formalin at 4° C. for histological analysis. At the same time, ovaries and residual uterus were also stored in formalin. After 10 hours, samples were transferred into a 3:1 PBS/Ethanol solution until tissue processing using standardized techniques. Afterwards, all samples were embedded in paraffin for histological sectioning.

Figure 10:
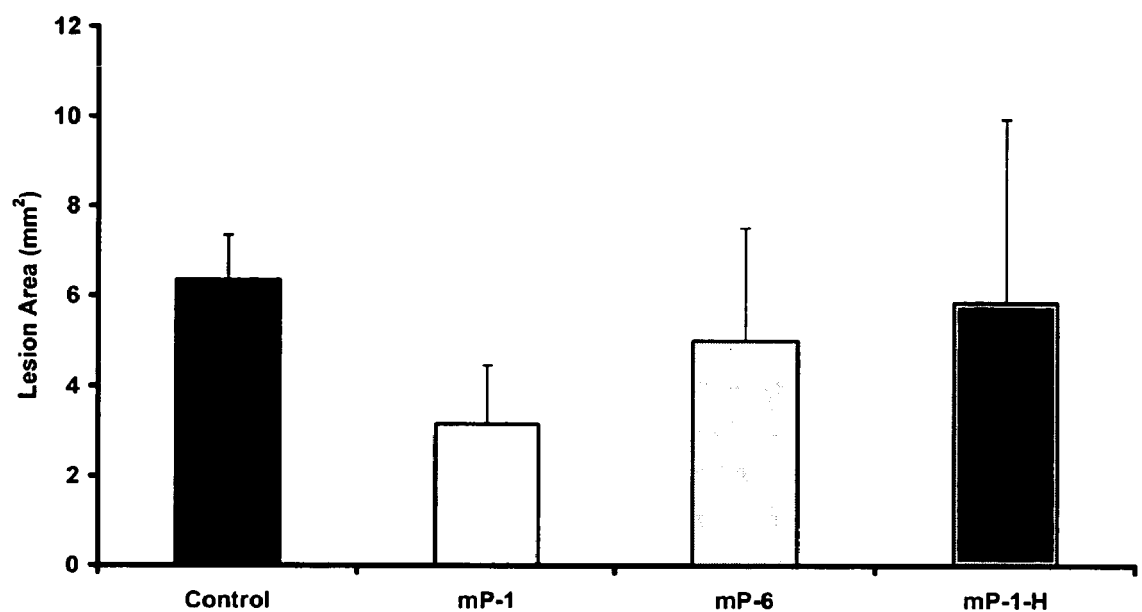
FIG. 10 is a graph showing the size of the endometriotic lesions in the groups of control mice, mice treated with mP-1, mice treated with mP-6, and mice treated with mP-1-H without zinc chloride supplementation.

In the initial experiment, control lesions had grown to the usual size as learned from earlier experiments (6.56 $mm^2$, ±2.46). As shown in FIG. 8, treatment with mP-1 inhibited the growth of endometriotic lesions by 51 and 55% in the low and high dose groups, respectively. In the larger follow-up experiment, treatment with 0.25 mg/kg mP-1 showed a reduction in lesion area by 38% compared to control animals (lesion area 3.9 mm$^2$±2.01 vs. 6.2 mm$^2$±2.3, respectively) when no zinc was added. At the same time, as shown in FIG. 10, lesion growth in the mP-6 group was also inhibited by 38% (lesion area 3.9 mm$^2$±1.09). No difference was seen in the growth of endometriotic lesions in mice treated with the mutant form of mP-1 relative to the control group (6.2 mm$^2$±1.38) (FIG. 10).

Figure 9:
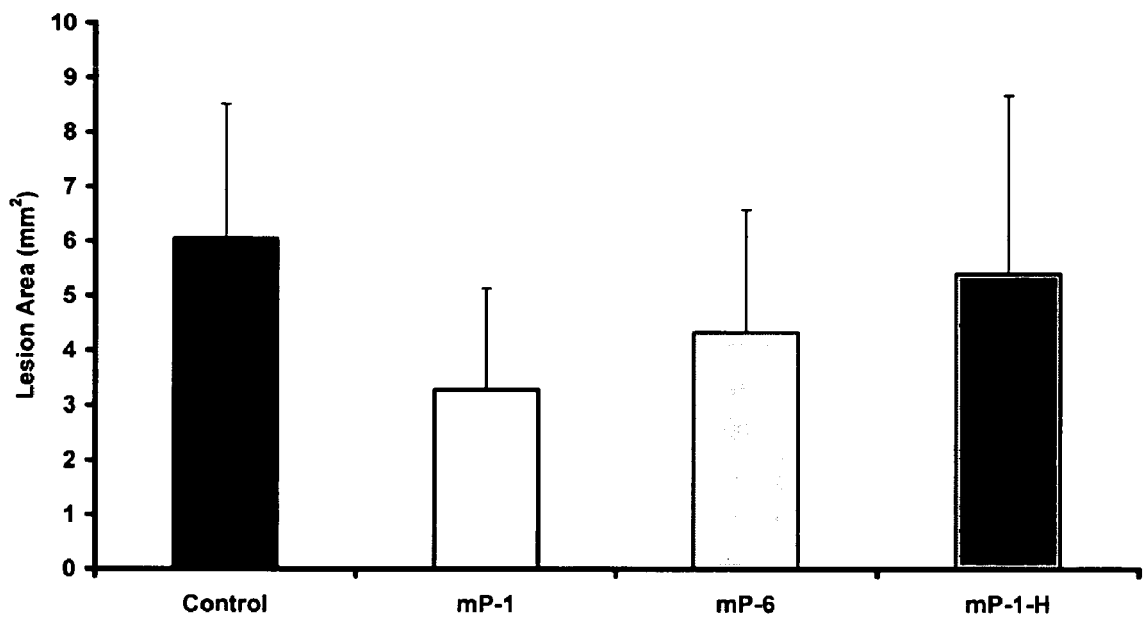
FIG. 9 is a graph showing the size of the endometriotic lesions in the groups of control mice, mice treated with a low dose of mP-1, mice treated with mP-6 (SEQ ID NO: 140) and mice treated with mP-1-H (SEQ ID NO: 150), supplemented with zinc chloride.

With ZnCl$_2$ added, growth of endometriotic lesions was significantly inhibited by 43% (mP-1) and 38% (mP-6) compared to PBS controls (lesion area 3.38 mm$^2$±2.20, 3.64 mm$^2$±1.70 vs. 5.90 mm$^2$±2.90, respectively) (FIG. 9). When no ZnCl$_2$ was added the inhibition with mP-1 was still significant compared to the PBS group (50% inhibition, 3.16 mm$^2$±1.30 vs. 6.35 mm$^2$±1.00, respectively). mP-6 did inhibit the growth of endometriotic lesions by 21%.

This experiment was undertaken to investigate if ZnCl$_2$ supplementation was necessary for peptide efficacy and to confirm data from the initial studies. Suprisingly, we found that when zinc was present in the peptide solutions, both mP1 and mP6 inhibited growth of endometriotic lesions, however, without zinc supplementation, mP6 showed less inhibition than mP1.

Anti-Angiogenic Peptides Have No Effect on Estrus Cycling

To investigate the effect of the angiogenesis inhibitors used above on estrus cycling, mice from the first two studies underwent daily vaginal smears in the middle of the endometriosis experiment. The stage of the estrus cycle was classified by evaluating the cells present at the cytological staining. Briefly, this was done as follows. In order to synchronize estrus cycling prior to surgery, mice were housed in groups of 5 for a week. After endometriosis surgery, with the intention to prevent the suspension of cycling, all mice were housed in individual cages. In the absence of a male, female mice housed in groups may become anestrus. Starting post surgical week two, estrus cycling was evaluated by cytological analysis of daily vaginal smears over one week's period. Exams were performed each day during the early morning hours. Autoclaved, wetted, blunt toothpicks were used to gently scrape the superficial cell layer of the animal's vagina. Cells were transferred to a drop of Evan's blue in 0.9% saline on a glass slide for staining, sealed under a glass cover slip and examined under a microscope (Carl Zeiss, Thornwood, N.Y.). Subsequently, each slide was analyzed under low magnification (×40 to ×100) by two independent investigators, who were masked for the form of treatment and previous data from every mouse.

In the initial experiment, daily vaginal cytology showed mice in both treatment groups and in the control group cycled normally. Even using 10 mg/kg, which is four times the dose used in tumor studies, did not have a negative influence. All animals went through the entire estrus cycle numerous times. An estrus cycle in a mouse usually takes between 1.5 and 5 days, explaining the intra- and inter-group variability in this experiment.

These findings could be reproduced in the larger experiment. Neither mP-1, not the other two peptides, mP-6 and mP-1-H led to an arrest of the estrus cycle in these mice.

Endostatin Peptides Do Not Reduce the Formation of Corpus Luteum

The corpus luteum (CL) is the remnant of the graafian follicle after ovulation consisting mainly of connective tissue, granulosa and theca interna cells. The presence of Corpora lutea in an ovary is indicative of recent ovulation. We therefore examined the ovaries of mP-1 and vehicle treated mice for CL formation. After 4 weeks of treatment of C57B1/6J mice with induced endometriosis with mP-1, ovaries were removed, fixed in formalin and paraffin embedded. Ovaries from twelve, randomly chosen mice (three mice of both groups from the first two experiments) were sectioned (4-6 μm), and four consecutive sections were put on one slide. Every other slide was then stained with hematoxylin and eosin (H/E). The highest number of Corpora lutea per ovary on each slide was recorded, all numbers added and the mean number calculated.

The results show that Corpora lutea were present in both treatment groups of the initial experiment and that mP-1 injections did not reduce the mean number of Corpora lutea in ovaries compared to control animals.

Thus, these results support our findings that the angiogenesis inhibitor mP-1 does not suppress ovarian function, while inhibiting the growth of endometriotic lesions in mice.

Endostatin Does Not Affect Female Mouse Fertility

Figure 11:
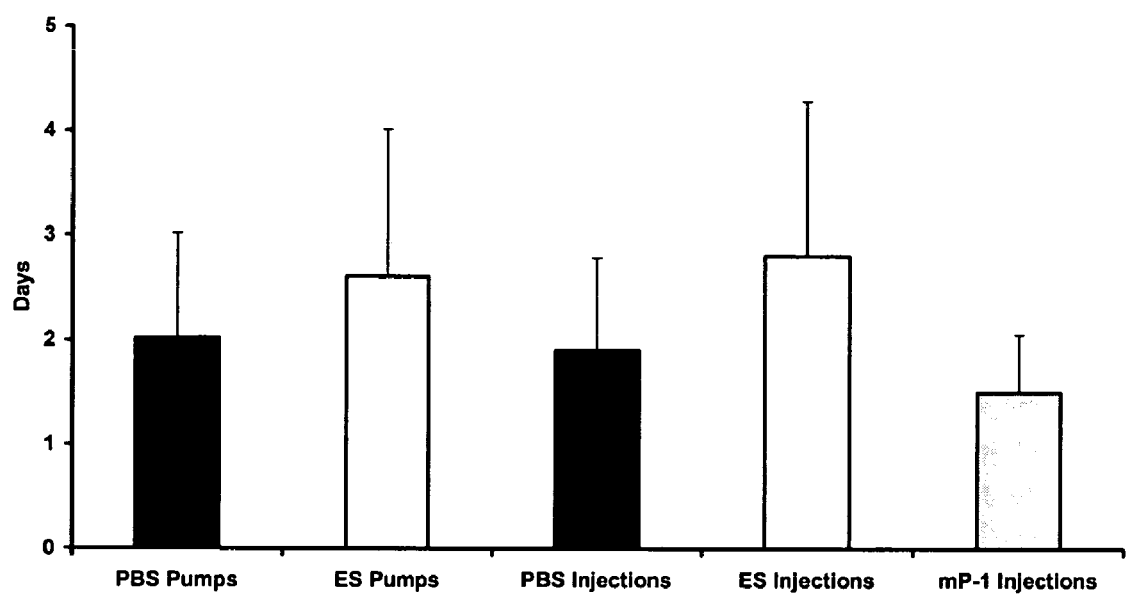
FIG. 11 is a graph showing that mating time is not prolonged by endostatin or mP-1 treatment.

Female SCID mice were injected with human pancreatic tumor cells subcutaneously. When tumors reached a volume of approximately 100 mm$^3$ endostatin or placebo treatment was initiated and continued until the end of the study. After three days, females were mated. Daily vaginal checks showed that endostatin did not delay the time for mating as indicated by the presence of a mucous plug. Mating time, defined as the time between male encounter and the presence of a mucous plug in the female's vagina in the PBS groups was 2.0±1 days for the pump and 1.9±0.9 days for the injection treated mice. When mice were treated with endostatin it took 2.6±1.4 days (pumps) and 2.8±1.5 days (injections) for the plug to appear, which was not statistically significantly longer (p=0.35 for pumps, 0.14 for injections). Successful mating took 1.5±0.6 days in mice treated with mP-1 injections, which was also not significantly different from the injection controls (p=0.67) (FIG. 11).

Pregnancy rates with live births were not reduced by treatment with endostatin or mP-1. In the control groups (PBS) they ranged between 39% and 100% in the pump mice and 60% and 100% in the injection mice in two separate experiments. The endostatin treated mice had pregnancy rates of 75% to 100% (pump mice) and 60% in the injection group. All mice receiving mP-1 became pregnant.

Treatment with either endostatin or mP-1 did not alter the duration of pregnancy. PBS pump mice were pregnant for a mean of 20+0 days in both experiments, their injection counterpart between 20±0 and 20.3±0.5 days. When treated with endostatin pumps the mean length of pregnancy ranged between 20.6±1.2 and 20.75±2 days and was exactly 20 days in the mP-1 group. The normal duration of pregnancy in a mouse ranges between 19-21 days.

Endostatin and mP-1 Did Not Have a Negative Effect on the Offspring

Figure 12:
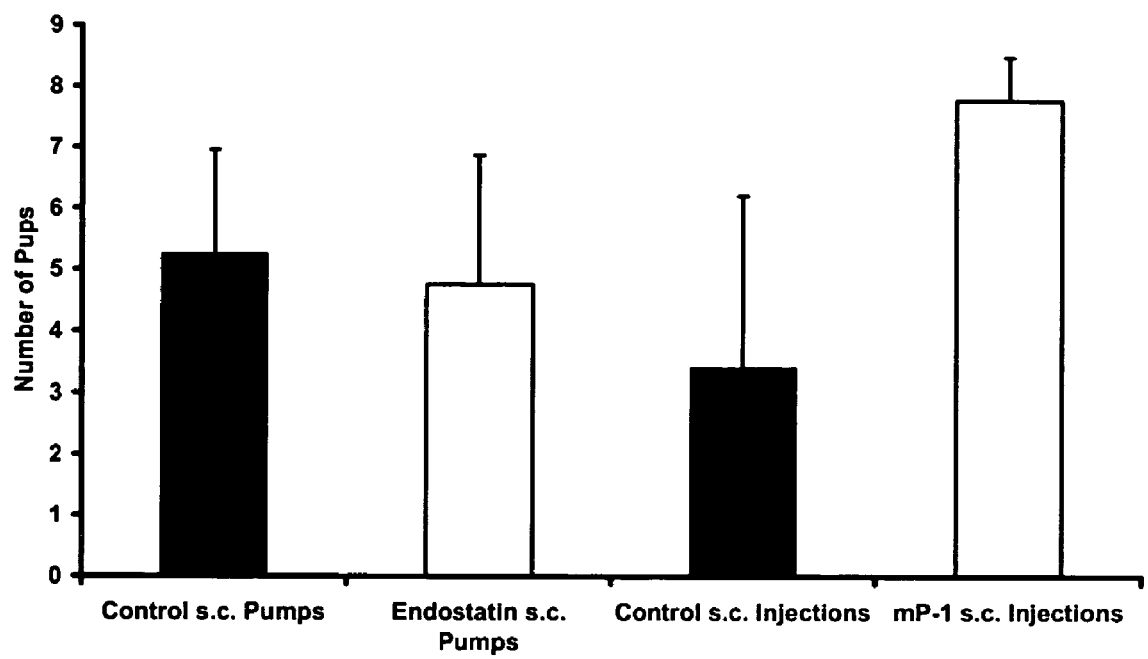
FIG. 12 is graph showing that litter size was not decreased by endostatin treatment in the pump group or by mP-1 in the injection group.

From studies with another anti-angiogenic drug it is know that they may cause teratogenicity. In this study we did not see any negative effect on the offspring of mice that were treated with endostatin or mP-1. All pubs were vital, healthy and had no crude signs of abnormalities. The litter size per delivery was not decreased by endostatin treatment in the pump group (PBS: 4.6±1.7; endostatin: 5±1.8; p=0.57). The same was true for the injection studies (PBS: 4.2±2.4; endostatin: 5±1; p=0.63), for mP-1 we even found a statistical increase in litter size (7.4±1.3; P=0.02) (FIG. 12). The mean weight of pubs on the day of delivery was not significantly affected by this treatment in the pump groups (PBS: 1.4 g±0.2; endostatin: 1.51 g±0.17; p=0.36) and in the injection groups (PBS: 1.48 g±0.2; mP-1: 1.29 g±0.1).

mP-1 Inhibits Migration of Human Endothelial Cells

Figure 13:
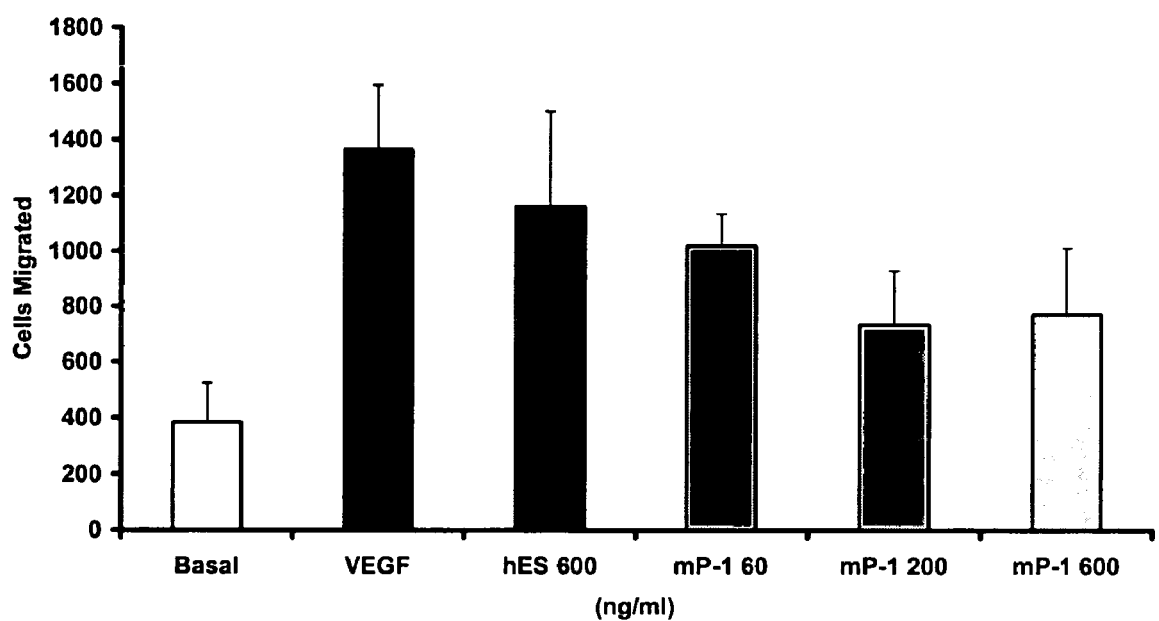
FIG. 13 is a graph showing that endostatin and mP-1 inhibit migration of human umbilical vein endothelial cells (HUVEC).

In order to prove that mP-1 that was used in the pregnancy experiment had intrinsic activity, we performed a migration assay with human umbilical vein endothelial cells (HUVEC). MP-1 was able to inhibit the VEGF stimulated migration of endothelial cells at various doses. As described previously (Tjin Tham Sjin and Javaherian), a U-shaped curve of efficacy was indicated (60 ng/ml mP-1 25% inhibition; 200 ng/ml 46% inhibition; 600 ng/ml 44% inhibition) confirming the data from the tumor studies (FIG. 13). This data suggests that mP-1 did have anti-endothelial efficacy while not showing toxic effects for fertility and pregnancy.

Materials and Methods:

Cell Culture and Reagents

Human BxPC-3 pancreatic carcinoma cells were grown and maintained as described earlier (Kisker et al. (2001) Cancer Res, 61:7669-7674; O'Reilly et al. (1994) Cell, 79: 315-328). Cells were grown in 175-cm$^2$ cell culture flasks. Primary human umbilical vein endothelial cells (HUVEC; Cambrex/Biowhittaker, San Diego, Calif.) were maintained according to the supplier's directions. For experiments, cells were grown to subconfluence and used between passages four to seven.

Lyophilized recombinant human endostatin (generous gift from EntreMed Corporation, Rockville, Md.) was reconstituted in sterile micro pure double distilled water to a stock concentration of 128 mg/ml and diluted in sterile phosphate buffered saline (PBS) immediately before further use.

The 27 amino acid murine N-terminal endostatin peptide (mP-1) (Tjin Tham Sjin and Javaherian) was synthesized by Synpep Corporation (Dublin, Calif.). The lyophilized peptide was resuspended in 1M $ZnCl_2$ in PBS, aliquoted and frozen at −80° C. until use.

Animal Studies

All animal work was performed in the animal facility at Children's Hospital, Boston, Mass., in accordance with federal, local, and institutional guidelines. 8 week-old female and male immune-compromised mice (SCID, Massachusetts General Hospital, Boston, Mass.) were caged in groups of five, separated by gender, and acclimated for a week in a barrier care facility. Mice were fed with autoclaved animal chow and water ad libitum.

All surgical procedures and ultrasound imaging were performed under inhalative anesthesia with isoflurane (Baxter, Deerfield, Ill.) and mice were observed until fully recovered. Animals were euthanized by a lethal dose of isoflurane followed by cervical dislocation.

Tumor Model

We have shown previously that human endostatin can inhibit tumor growth of xenotransplanted pancreatic cancer cells (Kisker et al., (2001) Cancer Res, 61:7669-7674). We used this model as a biomarker of endostatin potency. Human BxPC-3 cells were grown in cells culture as described above. After washing with sterile PBS, cells were trypsinized and briefly re-suspended in RPMI 1640 medium containing 10% fetal calf serum (FCS) and 1% glutamine penicillin streptomycin (GPS) solution. After centrifuging, the cell concentration was adjusted to $50 \times 10^6$ cells/ml in additive-free RPMI 1640 medium and kept on ice. Female SCID mice were shaved on the dorsal side and the naked skin was cleaned with ethanol prior to injection. A suspension of $5 \times 10^6$ cells/ml in 100 µl was then injected subcutaneously into the dorsa of these mice at about one centimetre left of the midline.

Mice were weighed and tumors were measured every 7 days in two diameters using a dial-caliper. Tumor volumes were calculated using the formula $a^2 \times b \times 0.52$, while a being the shorter and b being the longer diameter. When tumors had reached a volume of approximately 100 mm$^2$ mice were divided into four groups.

During the first experiment, one group received endostatin (20 mg/kg; n=8) or vehicle (n=8) via subcutaneous osmotic pumps (Durect Corp., Cupertino, Calif.). Pumps were inserted via a small incision and placed into a subcutaneous pocket on the right lateral aspect of the animals' dorsa. The pumps were changed every week for a total of four weeks.

The other group received daily subcutaneous injections of endostatin (100 mg/kg, n=5) or vehicle (n=5) for the same period. As tumor volumes in the injection groups were slightly smaller compared to the pump groups, treatment was started one day later.

During a second study we repeated the experiment with endostatin in subcutaneous pumps. The other group in this series received the murine N-terminal fragment of endostatin (mP-1) at a dose of 2.5 mg/kg twice daily or PBS (n=5 each).

Mating

Three days after initiation of treatment female mice were added to a cage containing a male SCID mouse in a 1:1 ratio. All males had been housed separately three days prior to encountering the females and female bedding had been added to the male cages to enhance the males' libido.

For the following seven days every female was checked for a vaginal mucous plug as a sign of mating. These exams were performed during the early morning hours to optimize the results. Once a mucous plug had been noticed, mating was considered 'successful', and the female was not further examined in order to minimize iatrogenic stress.

Over the course of pregnancy the following parameters were assessed: 'Mating Time' describing the time between male encounter and the occurrence of a mucous plug; 'Pregnancy Rate', measured by ultrasound 15 days after the mucous plug was observed. The number of viable fetus was counted during this procedure; 'Length of Pregnancy', as measured from the time of successful mating to delivery; 'Number of Total and Viable Litter', counted on the day of birth; 'Weight of Individual Pup', by weighing the entire litter on the day of birth and calculating the mean weight.

Ultrasound Imaging

Using the day of successful mating as the initiation point possible pregnancy dates were calculated (usually 19-21 days). In order to rule out loss of offspring due to problems during delivery or postnatal cannibalism we counted the number of vital fetuses during calculated pregnancy day 15. Under inhalative anesthesia we used a 15 MHz linear transducer (Sequoia Systems, Siemens Medical Solutions USA Inc., Malvern, Pa.) to count the number of fetuses in B-mode by identifying both cardial and skeletal structures. Doppler ultrasound imaging of the fetuses' cardiovascular system was performed and mice were counted as vital when blood flow could be displayed.

Migration Assay

Cell migration assays were performed using modified Boyden chambers (6.5-mm diameter, 10-µm thickness, 8-µm pores, Transwell-Costar Corp., Cambridge, Mass.) coated with 10 µg/ml fibronectin in PBS overnight at 4° C. and rinsed with PBS. Subconfluent cells were trypsinized (0.01% trypsin/5 mM EDTA), neutralized with trypsin neutralization solution (Cascade Biologics Inc., Portland, Oreg.), washed, and resuspended in endothelial basal medium (EBM; Clonetics) with 0.1% BSA in the presence or absence of human endostatin (40, 200, 1000 ng/ml). In a second experiment we added either 600 ng/ml human endostatin or mP-1 at various doses (60, 200, 600 ng/ml). Cells were maintained in suspension for 30 min, added to the top of each migration chamber and allowed to migrate for 4 h in the presence or absence of VEGF (5 ng/ml) in lower chamber. Adherent cells were fixed and stained using the Hema-3 Stain System (Fisher Diagnostics, Middletown, Va.), following manufacturer's instructions. Non-migratory cells were removed with a cotton swab, and the number of migratory cells per membrane was captured using bright field microscopy connected to a Spot digital camera (Diagnostic Instruments, Sterling Heights, Mich.). Migrated cells from the captured image were counted using NIH image software. Each determination represents the average of three individual wells, and error bars represent the standard deviation. Migration was normalized to percent migration, with migration to VEGF alone representing 100% migration. Each experiment was repeated a minimum of three times.

Incorporation by Reference

The contents of all cited references (including literature references, GenBank Accession numbers, issued patents, published patent applications as cited throughout this application) are hereby expressly incorporated by reference.

Equivalents

Those skilled in the art will recognize, or be able to ascertain using no more than routine experimentation, many equivalents of the specific embodiments of the invention described herein. Such equivalents are intended to be encompassed by the following claims.

The invention claimed is:

1. A method for treating endometriosis in a subject comprising administering to a subject in need thereof a therapeutically effective amount of a peptide, consisting of 10 to 35 amino acids of the N-terminal region of a human endostatin protein including the first histidine of the endostatin protein, or variant thereof, wherein the peptide does not consist of SEQ ID NO: 48.

2. The method of claim 1, wherein the peptide consists of 21 to 30 amino acids.

3. The method of claim 1, wherein the peptide is selected from the group consisting of SEQ ID NOs: 2, 6, 38, 40, 42, 44, 46, 50, 52, 54, 56, 58, 60, 62, 64, 125, 126, 130, and 131.

4. The method of claim 1, wherein the peptide contains a substitution, deletion or addition of one amino acid relative to the naturally occurring sequence.

5. The method of claim 1, wherein the peptide contains a substitution, deletion or addition of two amino acids relative to the naturally occurring sequence.

6. The method of claim 1, wherein the peptide contains a deletion or addition of three amino acids relative to the naturally occurring sequence.

7. The method of claim 1, further comprising administering to the subject an effective amount of zinc.

8. The method of claim 1, further comprising administering to the subject a second peptide.

9. The method of claim 1, wherein the peptide is SEQ ID NO: 2.

10. The method of claim 1, wherein the peptide consists of 10 to 35 amino acids of the N-terminal region of a human endostatin protein including the first histidine of the endostatin protein, wherein the peptide does not consist of SEQ TD NO: 48.

11. The method of claim 1, wherein the peptide consists of 12 amino acids of SEQ ID NO: 2 or 6 including the first histidine.

12. The method of claim 1, wherein the peptide is SEQ ID NO: 6.

13. The method of claim 1, wherein the peptide consists of an amino acid sequence that is at least 95% identical to SEQ ID NO: 2, 6, 38, 40, 42, 44, 46, 50, 52, 54, 56, 58, 60, 62, 64, 125 or 126.

14. The method of claim 1, wherein the peptide is linked to a heterologous peptide.

15. The method of claim 3, wherein the peptide is linked to a heterologous peptide.

16. The method of claim 13, wherein the peptide is linked to a heterologous peptide.

17. A method for treating endometriosis in a subject comprising administering to a subject in need thereof a therapeutically effective amount of a peptide, consisting of 10 to 35 amino acids of the N-terminal region of an endostatin protein including the first histidine of the endostatin protein, or variant thereof, wherein the peptide does not consist of SEQ ID NO: 48, 102 or 108.

18. The method of claim 17, wherein the peptide consists of 10 to 35 amino acids of the N-terminal region of an endostatin protein including the first histidine of the endostatin protein.

19. The method of claim 17, wherein the peptide consists of 21 to 30 amino acids.

20. The method of claim 17, wherein the peptide consists of an amino acid sequence that is at least 95% identical to SEQ ID NO: 4, 96, 98, 100, 104, 106, 110, 112, 114, 116, 118, 120, 122, 124, 128 or 129.

21. The method of claim 20, wherein the peptide is selected from the group consisting of SEQ ID NOs: 4, 96, 98, 100, 104, 106, 110, 112, 114, 116, 118, 120, 122, 124, 128 and 129.

22. The method of claim 21, wherein the peptide consists of SEQ ID NO: 4.

23. The method of claim 20, wherein the peptide consists of 12 amino acids of SEQ ID NO: 4.

24. The method of claim 17, wherein the peptide is linked to a heterologous peptide.

25. The method of claim 20, wherein the peptide is linked to a heterologous peptide.

26. The method of claim 21, wherein the peptide is linked to a heterologous peptide.

27. The method of claim 1, wherein the subject is human.

28. The method of claim 3, wherein the subject is human.

29. The method of claim 13, wherein the subject is human.

30. The method of claim 17, wherein the subject is human.

31. The method of claim 20, wherein the subject is human.

32. The method of claim 21, wherein the subject is human.

* * * * *

UNITED STATES PATENT AND TRADEMARK OFFICE
CERTIFICATE OF CORRECTION

PATENT NO. : 7,645,735 B2
APPLICATION NO. : 11/364887
DATED : January 12, 2010
INVENTOR(S) : Judah Folkman et al.

It is certified that error appears in the above-identified patent and that said Letters Patent is hereby corrected as shown below:

In the Claims:

In Claim 10, column 92, ln 43,

After "tin protein, wherein the peptide does not consist of SEQ" delete "TD" and replace with -- ID --

Signed and Sealed this

Twenty-third Day of November, 2010

David J. Kappos
*Director of the United States Patent and Trademark Office*

```
                            SEQUENCE LISTING

<160> NUMBER OF SEQ ID NOS: 155

<210> SEQ ID NO 1
<211> LENGTH: 81
<212> TYPE: DNA
<213> ORGANISM: Homo sapiens

<400> SEQUENCE: 1
cacagccacc gcgacttcca gccggtgctc cacctggttg cgctcaacag ccccctgtca      60
ggcggcatgc ggggcatccg c                                                81

<210> SEQ ID NO 2
<211> LENGTH: 27
<212> TYPE: PRT
<213> ORGANISM: Homo sapiens

<400> SEQUENCE: 2

His Ser His Arg Asp Phe Gln Pro Val Leu His Leu Val Ala Leu Asn
  1               5                  10                  15

Ser Pro Leu Ser Gly Gly Met Arg Gly Ile Arg
             20                  25

<210> SEQ ID NO 3
<211> LENGTH: 81
<212> TYPE: DNA
<213> ORGANISM: Mus musculus

<400> SEQUENCE: 3
catactcatc aggactttca gccagtgctc cacctggtgg cactgaacac cccctgtct       60 ggaggcatgc gtggtatccg t                                                81

<210> SEQ ID NO 4
<211> LENGTH: 27
<212> TYPE: PRT
<213> ORGANISM: Mus musculus

<400> SEQUENCE: 4

His Thr His Gln Asp Phe Gln Pro Val Leu His Leu Val Ala Leu Asn
  1               5                  10                  15

Thr Pro Leu Ser Gly Gly Met Arg Gly Ile Arg
             20                  25

<210> SEQ ID NO 5
<211> LENGTH: 75
```

```
<212> TYPE: DNA
<213> ORGANISM: Homo sapiens

<400> SEQUENCE: 5
catactcatc aggactttca gccagtgctc cacctggtgg cactgaacac cccctgtct    60 ggaggcatgc gtggt                                                   75

<210> SEQ ID NO 6
<211> LENGTH: 25
<212> TYPE: PRT
<213> ORGANISM: Homo sapiens

<400> SEQUENCE: 6

His Ser His Arg Asp Phe Gln Pro Val Leu His Leu Val Ala Leu Asn
 1               5                  10                  15

Ser Pro Leu Ser Gly Gly Met Arg Gly
             20                  25

<210> SEQ ID NO 7
<211> LENGTH: 78
<212> TYPE: DNA
<213> ORGANISM: Homo sapiens

<400> SEQUENCE: 7
agccaccgcg acttccagcc ggtgctccac ctggttgcgc tcaacagccc cctgtcaggc    60
ggcatgcggg gcatccgc                                                 78

<210> SEQ ID NO 8
<211> LENGTH: 26
<212> TYPE: PRT
<213> ORGANISM: Homo sapiens

<400> SEQUENCE: 8

Ser His Arg Asp Phe Gln Pro Val Leu His Leu Val Ala Leu Asn Ser
 1               5                  10                  15

Pro Leu Ser Gly Gly Met Arg Gly Ile Arg
             20                  25

<210> SEQ ID NO 9
<211> LENGTH: 75
<212> TYPE: DNA
<213> ORGANISM: Homo sapiens

<400> SEQUENCE: 9
caccgcgact tccagccggt gctccacctg gttgcgctca acagcccct gtcaggcggc    60 atgcggggca tccgc                                                   75

<210> SEQ ID NO 10
<211> LENGTH: 25
<212> TYPE: PRT
<213> ORGANISM: Homo sapiens

<400> SEQUENCE: 10

His Arg Asp Phe Gln Pro Val Leu His Leu Val Ala Leu Asn Ser Pro
 1               5                  10                  15

Leu Ser Gly Gly Met Arg Gly Ile Arg
             20                  25

<210> SEQ ID NO 11
<211> LENGTH: 72
<212> TYPE: DNA
```

```
<213> ORGANISM: Homo sapiens

<400> SEQUENCE: 11
cgcgacttcc agccggtgct ccacctggtt gcgctcaaca gcccctgtc  aggcggcatg    60 cggggcatcc gc                                                       72

<210> SEQ ID NO 12
<211> LENGTH: 24
<212> TYPE: PRT
<213> ORGANISM: Homo sapiens

<400> SEQUENCE: 12

Arg Asp Phe Gln Pro Val Leu His Leu Val Ala Leu Asn Ser Pro Leu
 1               5                  10                  15

Ser Gly Gly Met Arg Gly Ile Arg
            20

<210> SEQ ID NO 13
<211> LENGTH: 69
<212> TYPE: DNA
<213> ORGANISM: Homo sapiens

<400> SEQUENCE: 13
gacttccagc cggtgctcca cctggttgcg ctcaacagcc cctgtcagg cggcatgcgg    60 ggcatccgc                                                           69

<210> SEQ ID NO 14
<211> LENGTH: 23
<212> TYPE: PRT
<213> ORGANISM: Homo sapiens

<400> SEQUENCE: 14

Asp Phe Gln Pro Val Leu His Leu Val Ala Leu Asn Ser Pro Leu Ser
 1               5                  10                  15

Gly Gly Met Arg Gly Ile Arg
            20

<210> SEQ ID NO 15
<211> LENGTH: 66
<212> TYPE: DNA
<213> ORGANISM: Homo sapiens

<400> SEQUENCE: 15
ttccagccgg tgctccacct ggttgcgctc aacagccccc tgtcaggcgg catgcggggc    60
atccgc                                                              66

<210> SEQ ID NO 16
<211> LENGTH: 22
<212> TYPE: PRT
<213> ORGANISM: Homo sapiens

<400> SEQUENCE: 16

Phe Gln Pro Val Leu His Leu Val Ala Leu Asn Ser Pro Leu Ser Gly
 1               5                  10                  15

Gly Met Arg Gly Ile Arg
            20

<210> SEQ ID NO 17
<211> LENGTH: 63
<212> TYPE: DNA
<213> ORGANISM: Homo sapiens
```

-continued

```
<400> SEQUENCE: 17
cagccggtgc tccacctggt tgcgctcaac agcccctgt caggcggcat gcggggcatc      60
cgc                                                                   63

<210> SEQ ID NO 18
<211> LENGTH: 21
<212> TYPE: PRT
<213> ORGANISM: Homo sapiens

<400> SEQUENCE: 18

Gln Pro Val Leu His Leu Val Ala Leu Asn Ser Pro Leu Ser Gly Gly
 1               5                  10                  15

Met Arg Gly Ile Arg
            20

<210> SEQ ID NO 19
<211> LENGTH: 60
<212> TYPE: DNA
<213> ORGANISM: Homo sapiens

<400> SEQUENCE: 19
ccggtgctcc acctggttgc gctcaacagc ccctgtcag gcggcatgcg ggcatccgc       60

<210> SEQ ID NO 20
<211> LENGTH: 20
<212> TYPE: PRT
<213> ORGANISM: Homo sapiens

<400> SEQUENCE: 20

Pro Val Leu His Leu Val Ala Leu Asn Ser Pro Leu Ser Gly Gly Met
 1               5                  10                  15

Arg Gly Ile Arg
            20

<210> SEQ ID NO 21
<211> LENGTH: 57
<212> TYPE: DNA
<213> ORGANISM: Homo sapiens

<400> SEQUENCE: 21
gtgctccacc tggttgcgct caacagcccc ctgtcaggcg gcatgcgggg catccgc       57

<210> SEQ ID NO 22
<211> LENGTH: 19
<212> TYPE: PRT
<213> ORGANISM: Homo sapiens

<400> SEQUENCE: 22

Val Leu His Leu Val Ala Leu Asn Ser Pro Leu Ser Gly Gly Met Arg
 1               5                  10                  15

Gly Ile Arg

<210> SEQ ID NO 23
<211> LENGTH: 54
<212> TYPE: DNA
<213> ORGANISM: Homo sapiens

<400> SEQUENCE: 23
ctccacctgg ttgcgctcaa cagcccctg tcaggcggca tgcggggcat ccgc            54
```

```
<210> SEQ ID NO 24
<211> LENGTH: 18
<212> TYPE: PRT
<213> ORGANISM: Homo sapiens

<400> SEQUENCE: 24

Leu His Leu Val Ala Leu Asn Ser Pro Leu Ser Gly Gly Met Arg Gly
 1               5                  10                  15

Ile Arg

<210> SEQ ID NO 25
<211> LENGTH: 51
<212> TYPE: DNA
<213> ORGANISM: Homo sapiens

<400> SEQUENCE: 25
cacctggttg cgctcaacag cccccctgtca ggcggcatgc ggggcatccg c          51

<210> SEQ ID NO 26
<211> LENGTH: 17
<212> TYPE: PRT
<213> ORGANISM: Homo sapiens

<400> SEQUENCE: 26

His Leu Val Ala Leu Asn Ser Pro Leu Ser Gly Gly Met Arg Gly Ile
 1               5                  10                  15

Arg

<210> SEQ ID NO 27
<211> LENGTH: 48
<212> TYPE: DNA
<213> ORGANISM: Homo sapiens

<400> SEQUENCE: 27
ctggttgcgc tcaacagccc cctgtcaggc ggcatgcggg gcatccgc               48

<210> SEQ ID NO 28
<211> LENGTH: 4
<212> TYPE: PRT
<213> ORGANISM: Homo sapiens

<400> SEQUENCE: 28

His Ser His Arg
 1

<210> SEQ ID NO 29
<211> LENGTH: 45
<212> TYPE: DNA
<213> ORGANISM: Homo sapiens

<400> SEQUENCE: 29
gttgcgctca acagcccccct gtcaggcggc atgcggggca tccgc                 45

<210> SEQ ID NO 30
<211> LENGTH: 15
<212> TYPE: PRT
<213> ORGANISM: Homo sapiens

<400> SEQUENCE: 30

Val Ala Leu Asn Ser Pro Leu Ser Gly Gly Met Arg Gly Ile Arg
 1               5                  10                  15

<210> SEQ ID NO 31
```

```
<211> LENGTH: 42
<212> TYPE: DNA
<213> ORGANISM: Homo sapiens

<400> SEQUENCE: 31
gcgctcaaca gcccctgtc aggcggcatg cggggcatcc gc                         42

<210> SEQ ID NO 32
<211> LENGTH: 14
<212> TYPE: PRT
<213> ORGANISM: Homo sapiens

<400> SEQUENCE: 32

Ala Leu Asn Ser Pro Leu Ser Gly Gly Met Arg Gly Ile Arg
  1               5                  10

<210> SEQ ID NO 33
<211> LENGTH: 39
<212> TYPE: DNA
<213> ORGANISM: Homo sapiens

<400> SEQUENCE: 33
ctcaacagcc ccctgtcagg cggcatgcgg ggcatccgc                            39

<210> SEQ ID NO 34
<211> LENGTH: 13
<212> TYPE: PRT
<213> ORGANISM: Homo sapiens

<400> SEQUENCE: 34

Leu Asn Ser Pro Leu Ser Gly Gly Met Arg Gly Ile Arg
  1               5                  10

<210> SEQ ID NO 35
<211> LENGTH: 36
<212> TYPE: DNA
<213> ORGANISM: Homo sapiens

<400> SEQUENCE: 35
aacagccccc tgtcaggcgg catgcggggc atccgc                               36

<210> SEQ ID NO 36
<211> LENGTH: 12
<212> TYPE: PRT
<213> ORGANISM: Homo sapiens

<400> SEQUENCE: 36

Asn Ser Pro Leu Ser Gly Gly Met Arg Gly Ile Arg
  1               5                  10

<210> SEQ ID NO 37
<211> LENGTH: 78
<212> TYPE: DNA
<213> ORGANISM: Homo sapiens

<400> SEQUENCE: 37
cacagccacc gcgacttcca gccggtgctc cacctggttg cgctcaacag ccccctgtca     60
ggcggcatgc ggggcatc                                                   78

<210> SEQ ID NO 38
<211> LENGTH: 26
<212> TYPE: PRT
<213> ORGANISM: Homo sapiens
```

-continued

<400> SEQUENCE: 38

His Ser His Arg Asp Phe Gln Pro Val Leu His Leu Val Ala Leu Asn
1               5                   10                  15

Ser Pro Leu Ser Gly Gly Met Arg Gly Ile
            20                  25

<210> SEQ ID NO 39
<211> LENGTH: 72
<212> TYPE: DNA
<213> ORGANISM: Homo sapiens

<400> SEQUENCE: 39
cacagccacc gcgacttcca gccggtgctc cacctggttg cgctcaacag cccctgtca     60 ggcggcatgc gg                                                        72

<210> SEQ ID NO 40
<211> LENGTH: 24
<212> TYPE: PRT
<213> ORGANISM: Homo sapiens

<400> SEQUENCE: 40

His Ser His Arg Asp Phe Gln Pro Val Leu His Leu Val Ala Leu Asn
1               5                   10                  15

Ser Pro Leu Ser Gly Gly Met Arg
            20

<210> SEQ ID NO 41
<211> LENGTH: 69
<212> TYPE: DNA
<213> ORGANISM: Homo sapiens

<400> SEQUENCE: 41
cacagccacc gcgacttcca gccggtgctc cacctggttg cgctcaacag cccctgtca     60 ggcggcatg                                                            69

<210> SEQ ID NO 42
<211> LENGTH: 23
<212> TYPE: PRT
<213> ORGANISM: Homo sapiens

<400> SEQUENCE: 42

His Ser His Arg Asp Phe Gln Pro Val Leu His Leu Val Ala Leu Asn
1               5                   10                  15

Ser Pro Leu Ser Gly Gly Met
            20

<210> SEQ ID NO 43
<211> LENGTH: 66
<212> TYPE: DNA
<213> ORGANISM: Homo sapiens

<400> SEQUENCE: 43
cacagccacc gcgacttcca gccggtgctc cacctggttg cgctcaacag cccctgtca     60 ggcggc                                                               66

<210> SEQ ID NO 44
<211> LENGTH: 22
<212> TYPE: PRT
<213> ORGANISM: Homo sapiens

<400> SEQUENCE: 44

His Ser His Arg Asp Phe Gln Pro Val Leu His Leu Val Ala Leu Asn
1               5                   10                  15

Ser Pro Leu Ser Gly Gly
            20

<210> SEQ ID NO 45
<211> LENGTH: 63
<212> TYPE: DNA
<213> ORGANISM: Homo sapiens

<400> SEQUENCE: 45
cacagccacc gcgacttcca gccggtgctc cacctggttg cgctcaacag cccctgtca    60 ggc                                                                 63

<210> SEQ ID NO 46
<211> LENGTH: 21
<212> TYPE: PRT
<213> ORGANISM: Homo sapiens

<400> SEQUENCE: 46

His Ser His Arg Asp Phe Gln Pro Val Leu His Leu Val Ala Leu Asn
1               5                   10                  15

Ser Pro Leu Ser Gly
            20

<210> SEQ ID NO 47
<211> LENGTH: 60
<212> TYPE: DNA
<213> ORGANISM: Homo sapiens

<400> SEQUENCE: 47
cacagccacc gcgacttcca gccggtgctc cacctggttg cgctcaacag cccctgtca    60

<210> SEQ ID NO 48
<211> LENGTH: 20
<212> TYPE: PRT
<213> ORGANISM: Homo sapiens

<400> SEQUENCE: 48

His Ser His Arg Asp Phe Gln Pro Val Leu His Leu Val Ala Leu Asn
1               5                   10                  15

Ser Pro Leu Ser
            20

<210> SEQ ID NO 49
<211> LENGTH: 57
<212> TYPE: DNA
<213> ORGANISM: Homo sapiens

<400> SEQUENCE: 49
cacagccacc gcgacttcca gccggtgctc cacctggttg cgctcaacag cccctg       57

<210> SEQ ID NO 50
<211> LENGTH: 19
<212> TYPE: PRT
<213> ORGANISM: Homo sapiens

<400> SEQUENCE: 50

His Ser His Arg Asp Phe Gln Pro Val Leu His Leu Val Ala Leu Asn
1               5                   10                  15

Ser Pro Leu

```
<210> SEQ ID NO 51
<211> LENGTH: 54
<212> TYPE: DNA
<213> ORGANISM: Homo sapiens

<400> SEQUENCE: 51
cacagccacc gcgacttcca gccggtgctc cacctggttg cgctcaacag cccc         54

<210> SEQ ID NO 52
<211> LENGTH: 18
<212> TYPE: PRT
<213> ORGANISM: Homo sapiens

<400> SEQUENCE: 52

His Ser His Arg Asp Phe Gln Pro Val Leu His Leu Val Ala Leu Asn
 1               5                  10                  15

Ser Pro

<210> SEQ ID NO 53
<211> LENGTH: 51
<212> TYPE: DNA
<213> ORGANISM: Homo sapiens

<400> SEQUENCE: 53
cacagccacc gcgacttcca gccggtgctc cacctggttg cgctcaacag c            51

<210> SEQ ID NO 54
<211> LENGTH: 17
<212> TYPE: PRT
<213> ORGANISM: Homo sapiens

<400> SEQUENCE: 54

His Ser His Arg Asp Phe Gln Pro Val Leu His Leu Val Ala Leu Asn
 1               5                  10                  15

Ser

<210> SEQ ID NO 55
<211> LENGTH: 48
<212> TYPE: DNA
<213> ORGANISM: Homo sapiens

<400> SEQUENCE: 55
cacagccacc gcgacttcca gccggtgctc cacctggttg cgctcaac               48

<210> SEQ ID NO 56
<211> LENGTH: 16
<212> TYPE: PRT
<213> ORGANISM: Homo sapiens

<400> SEQUENCE: 56

His Ser His Arg Asp Phe Gln Pro Val Leu His Leu Val Ala Leu Asn
 1               5                  10                  15

<210> SEQ ID NO 57
<211> LENGTH: 45
<212> TYPE: DNA
<213> ORGANISM: Homo sapiens

<400> SEQUENCE: 57
cacagccacc gcgacttcca gccggtgctc cacctggttg cgctc                  45
```

<210> SEQ ID NO 58
<211> LENGTH: 15
<212> TYPE: PRT
<213> ORGANISM: Homo sapiens

<400> SEQUENCE: 58

His Ser His Arg Asp Phe Gln Pro Val Leu His Leu Val Ala Leu
1               5                   10                  15

<210> SEQ ID NO 59
<211> LENGTH: 42
<212> TYPE: DNA
<213> ORGANISM: Homo sapiens

<400> SEQUENCE: 59
cacagccacc gcgacttcca gccggtgctc cacctggttg cg                          42

<210> SEQ ID NO 60
<211> LENGTH: 14
<212> TYPE: PRT
<213> ORGANISM: Homo sapiens

<400> SEQUENCE: 60

His Ser His Arg Asp Phe Gln Pro Val Leu His Leu Val Ala
1               5                   10

<210> SEQ ID NO 61
<211> LENGTH: 39
<212> TYPE: DNA
<213> ORGANISM: Homo sapiens

<400> SEQUENCE: 61
cacagccacc gcgacttcca gccggtgctc cacctggtt                              39

<210> SEQ ID NO 62
<211> LENGTH: 13
<212> TYPE: PRT
<213> ORGANISM: Homo sapiens

<400> SEQUENCE: 62

His Ser His Arg Asp Phe Gln Pro Val Leu His Leu Val
1               5                   10

<210> SEQ ID NO 63
<211> LENGTH: 36
<212> TYPE: DNA
<213> ORGANISM: Homo sapiens

<400> SEQUENCE: 63
cacagccacc gcgacttcca gccggtgctc cacctg                                 36

<210> SEQ ID NO 64
<211> LENGTH: 12
<212> TYPE: PRT
<213> ORGANISM: Homo sapiens

<400> SEQUENCE: 64

His Ser His Arg Asp Phe Gln Pro Val Leu His Leu
1               5                   10

<210> SEQ ID NO 65
<211> LENGTH: 78
<212> TYPE: DNA
<213> ORGANISM: Homo sapiens -continued

```
<400> SEQUENCE: 65
actcatcagg actttcagcc agtgctccac ctggtggcac tgaacacccc cctgtctgga    60
ggcatgcgtg gtatccgt                                                  78

<210> SEQ ID NO 66
<211> LENGTH: 26
<212> TYPE: PRT
<213> ORGANISM: Homo sapiens

<400> SEQUENCE: 66

Thr His Gln Asp Phe Gln Pro Val Leu His Leu Val Ala Leu Asn Thr
 1               5                  10                  15

Pro Leu Ser Gly Gly Met Arg Gly Ile Arg
            20                  25

<210> SEQ ID NO 67
<211> LENGTH: 75
<212> TYPE: DNA
<213> ORGANISM: Homo sapiens

<400> SEQUENCE: 67
catcaggact ttcagccagt gctccacctg gtggcactga acacccccct gtctggaggc    60
atgcgtggta tccgt                                                     75

<210> SEQ ID NO 68
<211> LENGTH: 25
<212> TYPE: PRT
<213> ORGANISM: Homo sapiens

<400> SEQUENCE: 68

His Gln Asp Phe Gln Pro Val Leu His Leu Val Ala Leu Asn Thr Pro
 1               5                  10                  15

Leu Ser Gly Gly Met Arg Gly Ile Arg
            20                  25

<210> SEQ ID NO 69
<211> LENGTH: 72
<212> TYPE: DNA
<213> ORGANISM: Homo sapiens

<400> SEQUENCE: 69
caggactttc agccagtgct ccacctggtg gcactgaaca cccccctgtc tggaggcatg    60
cgtggtatcc gt                                                        72

<210> SEQ ID NO 70
<211> LENGTH: 24
<212> TYPE: PRT
<213> ORGANISM: Homo sapiens

<400> SEQUENCE: 70

Gln Asp Phe Gln Pro Val Leu His Leu Val Ala Leu Asn Thr Pro Leu
 1               5                  10                  15

Ser Gly Gly Met Arg Gly Ile Arg
            20

<210> SEQ ID NO 71
<211> LENGTH: 69
<212> TYPE: DNA
<213> ORGANISM: Homo sapiens

<400> SEQUENCE: 71
```

```
gactttcagc cagtgctcca cctggtggca ctgaacaccc ccctgtctgg aggcatgcgt    60
ggtatccgt                                                            69
```

<210> SEQ ID NO 72
<211> LENGTH: 23
<212> TYPE: PRT
<213> ORGANISM: Homo sapiens

<400> SEQUENCE: 72

```
Asp Phe Gln Pro Val Leu His Leu Val Ala Leu Asn Thr Pro Leu Ser
 1               5                  10                  15

Gly Gly Met Arg Gly Ile Arg
            20
```

<210> SEQ ID NO 73
<211> LENGTH: 66
<212> TYPE: DNA
<213> ORGANISM: Homo sapiens

<400> SEQUENCE: 73

```
tttcagccag tgctccacct ggtggcactg aacaccccccc tgtctggagg catgcgtggt   60
atccgt                                                               66
```

<210> SEQ ID NO 74
<211> LENGTH: 22
<212> TYPE: PRT
<213> ORGANISM: Homo sapiens

<400> SEQUENCE: 74

```
Phe Gln Pro Val Leu His Leu Val Ala Leu Asn Thr Pro Leu Ser Gly
 1               5                  10                  15

Gly Met Arg Gly Ile Arg
            20
```

<210> SEQ ID NO 75
<211> LENGTH: 63
<212> TYPE: DNA
<213> ORGANISM: Homo sapiens

<400> SEQUENCE: 75

```
cagccagtgc tccacctggt ggcactgaac accccctgt ctggaggcat gcgtggtatc    60
cgt                                                                  63
```

<210> SEQ ID NO 76
<211> LENGTH: 21
<212> TYPE: PRT
<213> ORGANISM: Homo sapiens

<400> SEQUENCE: 76

```
Gln Pro Val Leu His Leu Val Ala Leu Asn Thr Pro Leu Ser Gly Gly
 1               5                  10                  15

Met Arg Gly Ile Arg
            20
```

<210> SEQ ID NO 77
<211> LENGTH: 60
<212> TYPE: DNA
<213> ORGANISM: Homo sapiens

<400> SEQUENCE: 77

```
ccagtgctcc acctggtggc actgaacacc cccctgtctg gaggcatgcg tggtatccgt    60
```

<210> SEQ ID NO 78
<211> LENGTH: 20
<212> TYPE: PRT
<213> ORGANISM: Homo sapiens

<400> SEQUENCE: 78

Pro Val Leu His Leu Val Ala Leu Asn Thr Pro Leu Ser Gly Gly Met
 1               5                  10                  15

Arg Gly Ile Arg
            20

<210> SEQ ID NO 79
<211> LENGTH: 57
<212> TYPE: DNA
<213> ORGANISM: Homo sapiens

<400> SEQUENCE: 79

```
gtgctccacc tggtggcact gaacaccccc ctgtctggag gcatgcgtgg tatccgt    57
```

<210> SEQ ID NO 80
<211> LENGTH: 19
<212> TYPE: PRT
<213> ORGANISM: Homo sapiens

<400> SEQUENCE: 80

Val Leu His Leu Val Ala Leu Asn Thr Pro Leu Ser Gly Gly Met Arg
 1               5                  10                  15

Gly Ile Arg

<210> SEQ ID NO 81
<211> LENGTH: 54
<212> TYPE: DNA
<213> ORGANISM: Homo sapiens

<400> SEQUENCE: 81

```
ctccacctgg tggcactgaa caccccctg tctggaggca tgcgtggtat ccgt    54
```

<210> SEQ ID NO 82
<211> LENGTH: 18
<212> TYPE: PRT
<213> ORGANISM: Homo sapiens

<400> SEQUENCE: 82

Leu His Leu Val Ala Leu Asn Thr Pro Leu Ser Gly Gly Met Arg Gly
 1               5                  10                  15

Ile Arg

<210> SEQ ID NO 83
<211> LENGTH: 51
<212> TYPE: DNA
<213> ORGANISM: Homo sapiens

<400> SEQUENCE: 83

```
cacctggtgg cactgaacac cccctgtct ggaggcatgc gtggtatccg t    51
```

<210> SEQ ID NO 84
<211> LENGTH: 17
<212> TYPE: PRT
<213> ORGANISM: Homo sapiens

<400> SEQUENCE: 84

His Leu Val Ala Leu Asn Thr Pro Leu Ser Gly Gly Met Arg Gly Ile
 1               5                   10                  15
Arg

<210> SEQ ID NO 85
<211> LENGTH: 48
<212> TYPE: DNA
<213> ORGANISM: Homo sapiens

<400> SEQUENCE: 85
ctggtggcac tgaacacccc cctgtctgga ggcatgcgtg gtatccgt                        48

<210> SEQ ID NO 86
<211> LENGTH: 16
<212> TYPE: PRT
<213> ORGANISM: Homo sapiens

<400> SEQUENCE: 86

Leu Val Ala Leu Asn Thr Pro Leu Ser Gly Gly Met Arg Gly Ile Arg
 1               5                   10                  15

<210> SEQ ID NO 87
<211> LENGTH: 45
<212> TYPE: DNA
<213> ORGANISM: Homo sapiens

<400> SEQUENCE: 87
gtggcactga acacccccct gtctggaggc atgcgtggta tccgt                           45

<210> SEQ ID NO 88
<211> LENGTH: 15
<212> TYPE: PRT
<213> ORGANISM: Homo sapiens

<400> SEQUENCE: 88

Val Ala Leu Asn Thr Pro Leu Ser Gly Gly Met Arg Gly Ile Arg
 1               5                   10                  15

<210> SEQ ID NO 89
<211> LENGTH: 42
<212> TYPE: DNA
<213> ORGANISM: Homo sapiens

<400> SEQUENCE: 89
gcactgaaca ccccctgtc tggaggcatg cgtggtatcc gt                               42

<210> SEQ ID NO 90
<211> LENGTH: 14
<212> TYPE: PRT
<213> ORGANISM: Homo sapiens

<400> SEQUENCE: 90

Ala Leu Asn Thr Pro Leu Ser Gly Gly Met Arg Gly Ile Arg
 1               5                   10

<210> SEQ ID NO 91
<211> LENGTH: 39
<212> TYPE: DNA
<213> ORGANISM: Homo sapiens

<400> SEQUENCE: 91
ctgaacaccc ccctgtctgg aggcatgcgt ggtatccgt                                  39

```
<210> SEQ ID NO 92
<211> LENGTH: 13
<212> TYPE: PRT
<213> ORGANISM: Homo sapiens

<400> SEQUENCE: 92

Leu Asn Thr Pro Leu Ser Gly Gly Met Arg Gly Ile Arg
  1               5                  10

<210> SEQ ID NO 93
<211> LENGTH: 36
<212> TYPE: DNA
<213> ORGANISM: Homo sapiens

<400> SEQUENCE: 93 aacaccccccc tgtctggagg catgcgtggt atccgt                              36

<210> SEQ ID NO 94
<211> LENGTH: 12
<212> TYPE: PRT
<213> ORGANISM: Homo sapiens

<400> SEQUENCE: 94

Asn Thr Pro Leu Ser Gly Gly Met Arg Gly Ile Arg
  1               5                  10

<210> SEQ ID NO 95
<211> LENGTH: 78
<212> TYPE: DNA
<213> ORGANISM: Homo sapiens

<400> SEQUENCE: 95
catactcatc aggactttca gccagtgctc cacctggtgg cactgaacac ccccctgtct     60
ggaggcatgc gtggtatc                                                  78

<210> SEQ ID NO 96
<211> LENGTH: 26
<212> TYPE: PRT
<213> ORGANISM: Homo sapiens

<400> SEQUENCE: 96

His Thr His Gln Asp Phe Gln Pro Val Leu His Leu Val Ala Leu Asn
  1               5                  10                  15

Thr Pro Leu Ser Gly Gly Met Arg Gly Ile
             20                  25

<210> SEQ ID NO 97
<211> LENGTH: 75
<212> TYPE: DNA
<213> ORGANISM: Homo sapiens

<400> SEQUENCE: 97
catactcatc aggactttca gccagtgctc cacctggtgg cactgaacac ccccctgtct     60
ggaggcatgc gtggt                                                     75

<210> SEQ ID NO 98
<211> LENGTH: 25
<212> TYPE: PRT
<213> ORGANISM: Homo sapiens

<400> SEQUENCE: 98

His Thr His Gln Asp Phe Gln Pro Val Leu His Leu Val Ala Leu Asn
```

```
                1               5                  10                 15
Thr Pro Leu Ser Gly Gly Met Arg Gly
                20                 25

<210> SEQ ID NO 99
<211> LENGTH: 72
<212> TYPE: DNA
<213> ORGANISM: Homo sapiens

<400> SEQUENCE: 99
catactcatc aggactttca gccagtgctc cacctggtgg cactgaacac cccctgtct      60 ggaggcatgc gt                                                         72

<210> SEQ ID NO 100
<211> LENGTH: 24
<212> TYPE: PRT
<213> ORGANISM: Homo sapiens

<400> SEQUENCE: 100

His Thr His Gln Asp Phe Gln Pro Val Leu His Leu Val Ala Leu Asn
 1               5                  10                 15
Thr Pro Leu Ser Gly Gly Met Arg
                20

<210> SEQ ID NO 101
<211> LENGTH: 69
<212> TYPE: DNA
<213> ORGANISM: Homo sapiens

<400> SEQUENCE: 101
catactcatc aggactttca gccagtgctc cacctggtgg cactgaacac cccctgtct      60 ggaggcatg                                                             69

<210> SEQ ID NO 102
<211> LENGTH: 23
<212> TYPE: PRT
<213> ORGANISM: Homo sapiens

<400> SEQUENCE: 102

His Thr His Gln Asp Phe Gln Pro Val Leu His Leu Val Ala Leu Asn
 1               5                  10                 15
Thr Pro Leu Ser Gly Gly Met
                20

<210> SEQ ID NO 103
<211> LENGTH: 66
<212> TYPE: DNA
<213> ORGANISM: Homo sapiens

<400> SEQUENCE: 103
catactcatc aggactttca gccagtgctc cacctggtgg cactgaacac cccctgtct      60 ggaggc                                                                66

<210> SEQ ID NO 104
<211> LENGTH: 22
<212> TYPE: PRT
<213> ORGANISM: Homo sapiens

<400> SEQUENCE: 104

His Thr His Gln Asp Phe Gln Pro Val Leu His Leu Val Ala Leu Asn
 1               5                  10                 15
```

Thr Pro Leu Ser Gly Gly
            20

<210> SEQ ID NO 105
<211> LENGTH: 63
<212> TYPE: DNA
<213> ORGANISM: Homo sapiens

<400> SEQUENCE: 105
catactcatc aggactttca gccagtgctc cacctggtgg cactgaacac cccccctgtct    60 gga                                                                   63

<210> SEQ ID NO 106
<211> LENGTH: 21
<212> TYPE: PRT
<213> ORGANISM: Homo sapiens

<400> SEQUENCE: 106

His Thr His Gln Asp Phe Gln Pro Val Leu His Leu Val Ala Leu Asn
  1               5                  10                  15

Thr Pro Leu Ser Gly
            20

<210> SEQ ID NO 107
<211> LENGTH: 60
<212> TYPE: DNA
<213> ORGANISM: Mus musculus

<400> SEQUENCE: 107
catactcatc aggactttca gccagtgctc cacctggtgg cactgaacac cccccctgtct    60

<210> SEQ ID NO 108
<211> LENGTH: 20
<212> TYPE: PRT
<213> ORGANISM: Mus musculus

<400> SEQUENCE: 108

His Thr His Gln Asp Phe Gln Pro Val Leu His Leu Val Ala Leu Asn
  1               5                  10                  15

Thr Pro Leu Ser
            20

<210> SEQ ID NO 109
<211> LENGTH: 57
<212> TYPE: DNA
<213> ORGANISM: Homo sapiens

<400> SEQUENCE: 109
catactcatc aggactttca gccagtgctc cacctggtgg cactgaacac ccccctg        57

<210> SEQ ID NO 110
<211> LENGTH: 19
<212> TYPE: PRT
<213> ORGANISM: Homo sapiens

<400> SEQUENCE: 110

His Thr His Gln Asp Phe Gln Pro Val Leu His Leu Val Ala Leu Asn
  1               5                  10                  15

Thr Pro Leu

<210> SEQ ID NO 111

<211> LENGTH: 54
<212> TYPE: DNA
<213> ORGANISM: Homo sapiens

<400> SEQUENCE: 111
catactcatc aggactttca gccagtgctc cacctggtgg cactgaacac cccc    54

<210> SEQ ID NO 112
<211> LENGTH: 18
<212> TYPE: PRT
<213> ORGANISM: Homo sapiens

<400> SEQUENCE: 112

His Thr His Gln Asp Phe Gln Pro Val Leu His Leu Val Ala Leu Asn
 1               5                  10                  15

Thr Pro

<210> SEQ ID NO 113
<211> LENGTH: 51
<212> TYPE: DNA
<213> ORGANISM: Homo sapiens

<400> SEQUENCE: 113
catactcatc aggactttca gccagtgctc cacctggtgg cactgaacac c    51

<210> SEQ ID NO 114
<211> LENGTH: 17
<212> TYPE: PRT
<213> ORGANISM: Homo sapiens

<400> SEQUENCE: 114

His Thr His Gln Asp Phe Gln Pro Val Leu His Leu Val Ala Leu Asn
 1               5                  10                  15

Thr

<210> SEQ ID NO 115
<211> LENGTH: 48
<212> TYPE: DNA
<213> ORGANISM: Homo sapiens

<400> SEQUENCE: 115
catactcatc aggactttca gccagtgctc cacctggtgg cactgaac    48

<210> SEQ ID NO 116
<211> LENGTH: 16
<212> TYPE: PRT
<213> ORGANISM: Homo sapiens

<400> SEQUENCE: 116

His Thr His Gln Asp Phe Gln Pro Val Leu His Leu Val Ala Leu Asn
 1               5                  10                  15

<210> SEQ ID NO 117
<211> LENGTH: 45
<212> TYPE: DNA
<213> ORGANISM: Mus musculus

<400> SEQUENCE: 117
catactcatc aggactttca gccagtgctc cacctggtgg cactg    45

<210> SEQ ID NO 118
<211> LENGTH: 15
<212> TYPE: PRT

<213> ORGANISM: Mus musculus

<400> SEQUENCE: 118

His Thr His Gln Asp Phe Gln Pro Val Leu His Leu Val Ala Leu
1               5                   10                  15

<210> SEQ ID NO 119
<211> LENGTH: 42
<212> TYPE: DNA
<213> ORGANISM: Homo sapiens

<400> SEQUENCE: 119
catactcatc aggactttca gccagtgctc cacctggtgg ca         42

<210> SEQ ID NO 120
<211> LENGTH: 14
<212> TYPE: PRT
<213> ORGANISM: Homo sapiens

<400> SEQUENCE: 120

His Thr His Gln Asp Phe Gln Pro Val Leu His Leu Val Ala
1               5                   10

<210> SEQ ID NO 121
<211> LENGTH: 39
<212> TYPE: DNA
<213> ORGANISM: Homo sapiens

<400> SEQUENCE: 121
catactcatc aggactttca gccagtgctc cacctggtg           39

<210> SEQ ID NO 122
<211> LENGTH: 13
<212> TYPE: PRT
<213> ORGANISM: Homo sapiens

<400> SEQUENCE: 122

His Thr His Gln Asp Phe Gln Pro Val Leu His Leu Val
1               5                   10

<210> SEQ ID NO 123
<211> LENGTH: 36
<212> TYPE: DNA
<213> ORGANISM: Homo sapiens

<400> SEQUENCE: 123
catactcatc aggactttca gccagtgctc cacctg              36

<210> SEQ ID NO 124
<211> LENGTH: 12
<212> TYPE: PRT
<213> ORGANISM: Homo sapiens

<400> SEQUENCE: 124

His Thr His Gln Asp Phe Gln Pro Val Leu His Leu
1               5                   10

<210> SEQ ID NO 125
<211> LENGTH: 21
<212> TYPE: PRT
<213> ORGANISM: Homo sapiens

<400> SEQUENCE: 125

His Ser His Arg Asp Phe Val Ala Leu Asn Ser Pro Leu Ser Gly Gly

-continued

```
                1               5                  10                  15
Met Arg Gly Ile Arg
            20

<210> SEQ ID NO 126
<211> LENGTH: 21
<212> TYPE: PRT
<213> ORGANISM: Homo sapiens

<400> SEQUENCE: 126

His Ser His Arg Asp Phe Gln Pro Val Leu His Leu Leu Ser Gly Gly
 1               5                  10                  15

Met Arg Gly Ile Arg
            20

<210> SEQ ID NO 127
<211> LENGTH: 21
<212> TYPE: PRT
<213> ORGANISM: Homo sapiens

<400> SEQUENCE: 127

Gln Pro Val Leu His Leu Val Ala Leu Asn Thr Pro Leu Ser Gly Gly
 1               5                  10                  15

Met Arg Gly Ile Arg
            20

<210> SEQ ID NO 128
<211> LENGTH: 21
<212> TYPE: PRT
<213> ORGANISM: Homo sapiens

<400> SEQUENCE: 128

His Thr His Gln Asp Phe Val Ala Leu Asn Thr Pro Leu Ser Gly Gly
 1               5                  10                  15

Met Arg Gly Ile Arg
            20

<210> SEQ ID NO 129
<211> LENGTH: 21
<212> TYPE: PRT
<213> ORGANISM: Homo sapiens

<400> SEQUENCE: 129

His Thr His Gln Asp Phe Gln Pro Val Leu His Leu Leu Ser Gly Gly
 1               5                  10                  15

Met Arg Gly Ile Arg
            20

<210> SEQ ID NO 130
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Variable amino acid
<220> FEATURE:
<221> NAME/KEY: MOD_RES
<222> LOCATION: (4)
<223> OTHER INFORMATION: Variable amino acid
<220> FEATURE:
<221> NAME/KEY: MOD_RES
```

-continued

```
<222> LOCATION: (17)
<223> OTHER INFORMATION: Variable amino acid

<400> SEQUENCE: 130

His Xaa His Xaa Asp Phe Gln Pro Val Leu His Leu Val Ala Leu Asn
 1               5                  10                  15

Xaa Pro Leu Ser Gly Gly Met Arg Gly Ile Arg
            20                  25

<210> SEQ ID NO 131
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Variable amino acid
<220> FEATURE:
<221> NAME/KEY: MOD_RES
<222> LOCATION: (4)
<223> OTHER INFORMATION: Variable amino acid
<220> FEATURE:
<221> NAME/KEY: MOD_RES
<222> LOCATION: (17)
<223> OTHER INFORMATION: Variable amino acid

<400> SEQUENCE: 131

His Xaa His Xaa Asp Phe Gln Pro Val Leu His Leu Val Ala Leu Asn
 1               5                  10                  15

Xaa Pro Leu Ser Gly
            20

<210> SEQ ID NO 132
<211> LENGTH: 699
<212> TYPE: DNA
<213> ORGANISM: Homo sapiens

<400> SEQUENCE: 132
gagcccaaat cttgtgacaa aactcacaca tgcccaccgt gcccagcacc tgaactcctg      60
gggggaccgt cagtcttcct cttccccccca aaacccaagg acaccctcat gatctcccgg    120
acccctgagg tcacatgcgt ggtggtggac gtgagccacg aagaccctga ggtcaagttc     180
aactggtacg tggacggcgt ggaggtgcat aatgccaaga caaagccgcg ggaggagcag     240
tacaacagca cgtaccgtgt ggtcagcgtc ctcaccgtcc tgcaccagga ctggctgaat     300
ggcaaggagt acaagtgcaa ggtctccaac aaagccctcc cagcccccat cgagaaaacc     360
atctccaaag ccaaagggca gccccgagaa ccacaggtgt acaccctgcc cccatcccgg     420
gatgagctga ccaagaacca ggtcagcctg acctgcctgg tcaaaggctt ctatcccagc     480
gacatcgccg tggagtggga gagcaatggg cagccggaga caactacaa gaccacgcct      540 cccgtgctgg actccgacgg ctccttcttc ctctacagca agctcaccgt ggacaagagc     600
aggtggcagc aggggaacgt cttctcatgc tccgtgatgc atgaggctct gcacaaccac     660
tacacgcaga agagcctctc cctgtctccg ggtaaatga                            699

<210> SEQ ID NO 133
<211> LENGTH: 232
<212> TYPE: PRT
<213> ORGANISM: Homo sapiens

<400> SEQUENCE: 133
```

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
        210                 215                 220

Ser Leu Ser Leu Ser Pro Gly Lys
225                 230

<210> SEQ ID NO 134
<211> LENGTH: 48
<212> TYPE: DNA
<213> ORGANISM: Homo sapiens

<400> SEQUENCE: 134
tctagaggtg gtctagtgcc gcgcggcagc ggttccccg ggttgcag                48

<210> SEQ ID NO 135
<211> LENGTH: 16
<212> TYPE: PRT
<213> ORGANISM: Homo sapiens

<400> SEQUENCE: 135

Ser Arg Gly Gly Leu Val Pro Arg Gly Ser Gly Pro Gly Leu Gln
1               5                   10                  15

<210> SEQ ID NO 136
<211> LENGTH: 25
<212> TYPE: PRT
<213> ORGANISM: Mus musculus

<400> SEQUENCE: 136

Met Arg Gly Ile Arg Gly Ala Asp Phe Gln Ala Phe Gln Gln Ala Arg
1               5                   10                  15

Ala Val Gly Leu Ser Gly Thr Phe Arg

```
                20                  25

<210> SEQ ID NO 137
<211> LENGTH: 25
<212> TYPE: PRT
<213> ORGANISM: Mus musculus

<400> SEQUENCE: 137

Thr Phe Arg Ala Phe Leu Ser Ser Arg Leu Gln Asp Leu Tyr Ser Ile
 1               5                  10                  15

Val Arg Arg Ala Asp Arg Gly Ser Val
                20                  25

<210> SEQ ID NO 138
<211> LENGTH: 25
<212> TYPE: PRT
<213> ORGANISM: Mus musculus

<400> SEQUENCE: 138

Gly Ser Val Pro Ile Val Asn Leu Lys Asp Glu Val Leu Ser Pro Ser
 1               5                  10                  15

Trp Asp Ser Leu Phe Ser Gly Ser Gln
                20                  25

<210> SEQ ID NO 139
<211> LENGTH: 25
<212> TYPE: PRT
<213> ORGANISM: Mus musculus

<400> SEQUENCE: 139

Gly Ser Gln Gly Gln Val Gln Pro Gly Ala Arg Ile Phe Ser Phe Asp
 1               5                  10                  15

Gly Arg Asp Val Leu Arg His Pro Ala
                20                  25

<210> SEQ ID NO 140
<211> LENGTH: 24
<212> TYPE: PRT
<213> ORGANISM: Mus musculus

<400> SEQUENCE: 140

His Pro Ala Trp Pro Gln Lys Ser Val Trp His Gly Ser Asp Pro Ser
 1               5                  10                  15

Gly Arg Arg Leu Met Glu Ser Tyr
                20

<210> SEQ ID NO 141
<211> LENGTH: 25
<212> TYPE: PRT
<213> ORGANISM: Mus musculus

<400> SEQUENCE: 141

Glu Thr Trp Arg Thr Glu Thr Gly Ala Thr Gly Gln Ala Ser Ser
 1               5                  10                  15

Leu Leu Ser Gly Arg Leu Leu Glu Gln
                20                  25

<210> SEQ ID NO 142
<211> LENGTH: 26
<212> TYPE: PRT
<213> ORGANISM: Mus musculus

<400> SEQUENCE: 142
```

```
Lys Ala Ala Ser Ala His Asn Ser Tyr Ile Val Leu Ala Ile Glu Asn
 1               5                  10                  15

Ser Phe Met Thr Ser Phe Ser Lys Lys Lys
                20                  25

<210> SEQ ID NO 143
<211> LENGTH: 25
<212> TYPE: PRT
<213> ORGANISM: Homo sapiens

<400> SEQUENCE: 143

Met Arg Gly Ile Arg Gly Ala Asp Phe Gln Ala Phe Gln Gln Ala Arg
 1               5                  10                  15

Ala Val Gly Leu Ala Gly Thr Phe Arg
                20                  25

<210> SEQ ID NO 144
<211> LENGTH: 25
<212> TYPE: PRT
<213> ORGANISM: Homo sapiens

<400> SEQUENCE: 144

Thr Phe Arg Ala Phe Leu Ser Ser Arg Leu Gln Asp Leu Tyr Ser Ile
 1               5                  10                  15

Val Arg Arg Ala Asp Arg Ala Ala Val
                20                  25

<210> SEQ ID NO 145
<211> LENGTH: 25
<212> TYPE: PRT
<213> ORGANISM: Homo sapiens

<400> SEQUENCE: 145

Ala Ala Val Pro Ile Val Asn Leu Lys Asp Glu Leu Leu Phe Pro Ser
 1               5                  10                  15

Trp Glu Ala Leu Phe Ser Gly Ser Glu
                20                  25

<210> SEQ ID NO 146
<211> LENGTH: 25
<212> TYPE: PRT
<213> ORGANISM: Homo sapiens

<400> SEQUENCE: 146

Gly Ser Glu Gly Pro Leu Lys Pro Gly Ala Arg Ile Phe Ser Phe Asp
 1               5                  10                  15

Gly Lys Asp Val Leu Arg His Pro Thr
                20                  25

<210> SEQ ID NO 147
<211> LENGTH: 24
<212> TYPE: PRT
<213> ORGANISM: Homo sapiens

<400> SEQUENCE: 147

His Pro Thr Trp Pro Gln Lys Ser Val Trp His Gly Ser Asp Pro Asn
 1               5                  10                  15

Gly Arg Arg Leu Thr Glu Ser Tyr
                20

<210> SEQ ID NO 148
```

```
<211> LENGTH: 25
<212> TYPE: PRT
<213> ORGANISM: Homo sapiens

<400> SEQUENCE: 148

Glu Thr Trp Arg Thr Glu Ala Pro Ser Ala Thr Gly Gln Ala Ser Ser
 1               5                  10                  15

Leu Leu Gly Gly Arg Leu Leu Gly Gln
             20                  25

<210> SEQ ID NO 149
<211> LENGTH: 28
<212> TYPE: PRT
<213> ORGANISM: Homo sapiens

<400> SEQUENCE: 149

Leu Gly Gln Ser Ala Ala Ser Ala His His Ala Tyr Ile Val Leu Ala
 1               5                  10                  15

Ile Glu Asn Ser Phe Met Thr Ala Ser Lys Lys Lys
             20                  25

<210> SEQ ID NO 150
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Ala Thr Ala Gln Asp Phe Gln Pro Val Leu His Leu Val Ala Leu Asn
 1               5                  10                  15

Thr Pro Leu Ser Gly Gly Met Arg Gly Ile Arg
             20                  25

<210> SEQ ID NO 151
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Lys Asp Glu Leu
 1

<210> SEQ ID NO 152
<211> LENGTH: 552
<212> TYPE: DNA
<213> ORGANISM: Homo sapiens

<400> SEQUENCE: 152
cacagccacc gcgacttcca gccggtgctc cacctggttg cgctcaacag cccccctgtca      60 ggcggcatgc ggggcatccg cggggccgac ttccagtgct ccagcaggc gcgggccgtg     120 gggctggcgg gcaccttccg cgccttcctg tcctcgcgcc tgcaggacct gtacagcatc     180
gtgcgccgtg ccgaccgcgc agccgtgccc atcgtcaacc tcaaggacga gctgctgttt     240
cccagctggg aggctctgtt ctcaggctct gagggtccgc tgaagcccgg ggcacgcatc     300
ttctccttta cggcaaggac gtcctgacc accccacct ggccccagaa gagcgtgtgg     360
catggctcgg accccaacgg gcgcaggctg accgagagct actgtgagac gtggcggacg     420
```

```
gaggctccct cggccacggg ccaggcctac tcgctgctgg ggggcaggct cctggggcag    480
agtgccgcga gctgccatca cgcctacatc gtgctatgca ttgagaacag cttcatgact    540
gcctccaagt ag                                                        552
```

```
<210> SEQ ID NO 153
<211> LENGTH: 183
<212> TYPE: PRT
<213> ORGANISM: Homo sapiens

<400> SEQUENCE: 153
```

```
His Ser His Arg Asp Phe Gln Pro Val Leu His Leu Val Ala Leu Asn
1               5                   10                  15

Ser Pro Leu Ser Gly Gly Met Arg Gly Ile Arg Gly Ala Asp Phe Gln
            20                  25                  30

Cys Phe Gln Gln Ala Arg Ala Val Gly Leu Ala Gly Thr Phe Arg Ala
        35                  40                  45

Phe Leu Ser Ser Arg Leu Gln Asp Leu Tyr Ser Ile Val Arg Arg Ala
    50                  55                  60

Asp Arg Ala Ala Val Pro Ile Val Asn Leu Lys Asp Glu Leu Leu Phe
65                  70                  75                  80

Pro Ser Trp Glu Ala Leu Phe Ser Gly Ser Glu Gly Pro Leu Lys Pro
                85                  90                  95

Gly Ala Arg Ile Phe Ser Phe Asn Gly Lys Asp Val Leu Thr His Pro
            100                 105                 110

Thr Trp Pro Gln Lys Ser Val Trp His Gly Ser Asp Pro Asn Gly Arg
        115                 120                 125

Arg Leu Thr Glu Ser Tyr Cys Glu Thr Trp Arg Thr Glu Ala Pro Ser
    130                 135                 140

Ala Thr Gly Gln Ala Tyr Ser Leu Leu Gly Gly Arg Leu Leu Gly Gln
145                 150                 155                 160

Ser Ala Ala Ser Cys His His Ala Tyr Ile Val Leu Cys Ile Glu Asn
                165                 170                 175

Ser Phe Met Thr Ala Ser Lys
            180
```

```
<210> SEQ ID NO 154
<211> LENGTH: 552
<212> TYPE: DNA
<213> ORGANISM: Mus musculus

<400> SEQUENCE: 154
catactcatc aggactttca gccagtgctc cacctggtgg cactgaacac ccccctgtct    60
ggaggcatgc gtggtatccg tggagcagat ttccagtgct tccagcaagc ccgagccgtg   120
gggctgtcgg gcaccttccg ggctttcctg tcctctaggc tgcaggatct ctatagcatc   180
gtgcgccgtg ctgaccgggg gtctgtgccc atcgtcaacc tgaaggacga ggtgctatct   240
cccagctggg actccctgtt ttctggctcc cagggtcaac tgcaacccgg ggcccgcatc   300
ttttcttttg acggcagaga tgtcctgaga cacccagcct ggccgcagaa gagcgtatgg   360
cacggctcgg accccagtgg gcggaggctg atggagagtt actgtgagac atggcgaact   420
gaaactactg gggctacagg tcaggcctcc tccctgctgt caggcaggct cctgaacag    480 aaagctgcga gctgccacaa cagctacatc gtcctgtgca ttgagaatag cttcatgacc   540
tctttctcca aa                                                       552
```

-continued

```
<210> SEQ ID NO 155
<211> LENGTH: 184
<212> TYPE: PRT
<213> ORGANISM: Mus musculus

<400> SEQUENCE: 155

His Thr His Gln Asp Phe Gln Pro Val Leu His Leu Val Ala Leu Asn
 1               5                  10                  15
Thr Pro Leu Ser Gly Gly Met Arg Gly Ile Arg Gly Ala Asp Phe Gln
             20                  25                  30
Cys Phe Gln Gln Ala Arg Ala Val Gly Leu Ser Gly Thr Phe Arg Ala
         35                  40                  45
Phe Leu Ser Ser Arg Leu Gln Asp Leu Tyr Ser Ile Val Arg Arg Ala
     50                  55                  60
Asp Arg Gly Ser Val Pro Ile Val Asn Leu Lys Asp Glu Val Leu Ser
 65                  70                  75                  80
Pro Ser Trp Asp Ser Leu Phe Ser Gly Ser Gln Gly Gln Leu Gln Pro
                 85                  90                  95
Gly Ala Arg Ile Phe Ser Phe Asp Gly Arg Asp Val Leu Arg His Pro
            100                 105                 110
Ala Trp Pro Gln Lys Ser Val Trp His Gly Ser Asp Pro Ser Gly Arg
        115                 120                 125
Arg Leu Met Glu Ser Tyr Cys Glu Thr Trp Arg Thr Glu Thr Thr Gly
    130                 135                 140
Ala Thr Gly Gln Ala Ser Ser Leu Leu Ser Gly Arg Leu Leu Glu Gln
145                 150                 155                 160
Lys Ala Ala Ser Cys His Asn Ser Tyr Ile Val Leu Cys Ile Glu Asn
                165                 170                 175
Ser Phe Met Thr Ser Phe Ser Lys
            180
```